(12) United States Patent
Kowalski et al.

(10) Patent No.: US 11,005,043 B2
(45) Date of Patent: *May 11, 2021

(54) ORGANIC SEMICONDUCTING POLYMER

(71) Applicant: Raynergy Tek Incorporation, Hsinchu (TW)

(72) Inventors: Sebastian Kowalski, Southampton (GB); Nicolas Blouin, Darmstadt (DE); Agnieszka Pron, Eastleigh (GB); Michal Krompiec, Southampton (GB)

(73) Assignee: RAYNERGY TEK INCORPORATION, Hsinchu (TW)

(*) Notice: Subject to any disclaimer, the term of this patent is extended or adjusted under 35 U.S.C. 154(b) by 0 days.

This patent is subject to a terminal disclaimer.

(21) Appl. No.: 16/637,950

(22) PCT Filed: Aug. 10, 2018

(86) PCT No.: PCT/EP2018/071763
§ 371 (c)(1),
(2) Date: Feb. 10, 2020

(87) PCT Pub. No.: WO2019/030382
PCT Pub. Date: Feb. 14, 2019

(65) Prior Publication Data
US 2020/0203614 A1    Jun. 25, 2020

(30) Foreign Application Priority Data
Aug. 11, 2017 (EP) .................... 17185962

(51) Int. Cl.
H01L 51/00 (2006.01)
C08G 61/12 (2006.01)
H01L 51/42 (2006.01)

(52) U.S. Cl.
CPC ........ H01L 51/0036 (2013.01); C08G 61/126 (2013.01); H01L 51/0043 (2013.01); *C08G 2261/124* (2013.01); *C08G 2261/149* (2013.01); *C08G 2261/1412* (2013.01); *C08G 2261/3223* (2013.01); *C08G 2261/3243* (2013.01); *C08G 2261/3246* (2013.01); *C08G 2261/414* (2013.01); *C08G 2261/514* (2013.01); *C08G 2261/91* (2013.01); *C08G 2261/94* (2013.01); *H01L 51/4253* (2013.01)

(58) Field of Classification Search
CPC ............ H01L 51/0036; H01L 51/0047; H01L 51/0035; H01L 51/0043; H01L 51/4253; C08G 61/126; C08G 2261/124; C08G 2261/1412; C08G 2261/149; C08G 2261/3223; C08G 2261/3243; C08G 2261/3246; C08G 2261/414; C08G 2261/514; C08G 2261/91; C08G 2261/94; C08G 2261/122; C08G 2261/1428; C08G 2261/146; C08G 2261/512; Y02E 10/549; C07D 417/14; C09D 165/00
USPC ............................ 252/500; 136/263; 257/40
See application file for complete search history.

(56) References Cited

U.S. PATENT DOCUMENTS

| 8,723,028 B2 | 5/2014 | Zhu et al. |
| 10,411,190 B2* | 9/2019 | Morse .................. C07D 333/22 |
| 2005/0082525 A1* | 4/2005 | Heeney ................ C08G 61/126 257/40 |
| 2009/0256139 A1* | 10/2009 | Wu ...................... H01L 51/0512 257/40 |
| 2013/0247990 A1 | 9/2013 | Facchetti et al. |
| 2018/0198068 A1* | 7/2018 | Morse .................. C09K 11/06 |

FOREIGN PATENT DOCUMENTS

WO    14157497 A1    10/2014

OTHER PUBLICATIONS

Daize Mo et al: "Chlorination of Low-Band-Gap Polymers: Toward High-Performance Polymer Solar Cells", Chemistry of Materials, vol. 29, No. 7, Mar. 8, 2017 (Mar. 8, 2017), pp. 2819-2830, XP055511815, ISSN: 0897-4756.
International Search Report PCT/EP2018/071763 dated Oct. 12, 2018 (pp. 1-3).

* cited by examiner

*Primary Examiner* — Douglas J McGinty
(74) *Attorney, Agent, or Firm* — WPAT, PC

(57) ABSTRACT

The invention relates to novel organic semiconducting polymers, to methods for their preparation and educts or intermediates used therein, to compositions containing them, to the use of the polymers and compositions as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these polymers or compositions.

10 Claims, No Drawings

ORGANIC SEMICONDUCTING POLYMER

TECHNICAL FIELD

The invention relates to novel organic semiconducting polymers, to methods for their preparation and educts or intermediates used therein, to compositions containing them, to the use of the polymers and compositions as organic semiconductors in, or for the preparation of, organic electronic (OE) devices, especially organic photovoltaic (OPV) devices, perovskite-based solar cell (PSC) devices, organic photodetectors (OPD), organic field effect transistors (OFET) and organic light emitting diodes (OLED), and to OE, OPV, PSC, OPD, OFET and OLED devices comprising these polymers or compositions.

BACKGROUND

In recent years, there has been development of organic semiconducting (OSC) materials in order to produce more versatile, lower cost electronic devices. Such materials find application in a wide range of devices or apparatus, including organic field effect transistors (OFETs), organic light emitting diodes (OLEDs), organic photodetectors (OPDs), organic photovoltaic (OPV) cells, sensors, memory elements and logic circuits to name just a few. The OSC materials are typically present in the electronic device in the form of a thin layer.

The OSC materials are receiving ever-growing attention mostly due to their lucrative commercial prospects in organic electronics manufactured by cost effective solution processing technology at low temperature. It is generally believed that OSCs have a number of advantage over their inorganic counterparts, such as the potential of fabricating lightweight flexible backplanes, the opportunity to make large area displays using low-cost, high speed solution based fabrication techniques, and their optical and electronic properties being fine-tuneable via rational chemical structure modifications.

The main disadvantages of the OSC materials currently known in prior art are their relatively low device performance and their modest thermal, photo and electrical stability. Over the past two decades a wide range of new π-conjugated polymers have been made available, and have shown improved performance in OE devices like OFETs such as high charge carrier mobility, reaching or even surpassing that of amorphous silicon. In the meantime, power conversion efficiencies of OPV cells fabricated using low bandgap π-conjugated polymers as active electron donor materials have exceeded 10%.

The performance of OFET devices is principally based upon the charge carrier mobility of the semiconducting material and the current on/off ratio, so the ideal semiconductor should have a low conductivity in the off state, combined with a high charge carrier mobility ($>1\times10^{-3}$ $cm^2V^{-1}$ $s^{-1}$). In addition, it is important that the semiconducting material is relatively stable to oxidation i.e. it has a high ionisation potential, as oxidative doping leads to reduced device performance, for example increased off current and threshold voltage shift. Further requirements for the semiconducting material to have include good processability, especially for large-scale production of thin-film layers and desired patterns, and high stability, thin-film uniformity and integrity of the organic semiconductor layer.

In OPV cells, π-conjugated polymers and organic small molecules have found use as OSC in the photoactive layer, as they allow devices to be manufactured by solution-processing techniques such as spin casting, dip coating or ink jet printing. Solution processing can be carried out cheaper and on a larger scale, compared to the evaporative techniques used to make inorganic thin film devices. In photoactive layers containing a blend of an n-type OSC and a p-type OSC, typically a π-conjugated polymer, forming a bulk-heterojunction (BHJ), the π-conjugated polymer serves as the main absorber of the solar energy. Therefore a low band gap is a basic requirement for the polymer to absorb the maximum of the solar spectrum. Thus, for use in OPV cells and OPDs, the OSC should have a low bandgap, which enables improved light harvesting by the photoactive layer and can lead to higher power conversion efficiency.

A commonly used strategy to achieve low bandgap OSC polymers for OPV and OPD applications is to utilize a π-conjugated D-A polymer consisting of both electron rich donor units D and electron deficient acceptor units A in the polymer backbone. Conjugated D-A polymers have also been found to demonstrate high charge carrier mobilities in OTFTs. It is generally accepted that the alternating D-A structure facilitates stronger intermolecular interactions, leading to smaller π-π-stacking distance and efficient intermolecular charge transfer due to static attractions between the donor and the acceptor monomer units.

To date, a large number of conjugated π-structures have been synthesized which can be used as monomers for preparing conjugated D-A polymers. However, the D-A polymers hitherto available do still leave room for further improvement, and the ideal polymer which combines high efficiency with facile and scalable synthesis has yet to be found.

Thus, there is still a need for OSC polymers which are suitable for use in OE devices like OTFTs, OPDs and OPV cells, and which show one or more of the above-mentioned desired properties.

It was an aim of the present invention to provide conjugated D-A polymers for use in OE devices like OFETs, OPDs and OPV devices, which are easy to synthesize, especially by methods suitable for mass production, which show especially good processibility, high stability, good solubility in organic solvents, high charge carrier mobility, and a low bandgap. Another aim of the invention was to extend the pool of OSC materials having electron acceptor property. Other aims of the present invention are immediately evident to the expert from the following detailed description.

The inventors of the present invention have found that one or more of the above aims can be achieved by providing a polymer as disclosed and claimed hereinafter, which is formed from a substituted benzodithiophene (BDT) unit and a benzothiadiazole-dithienylene unit, or a derivative thereof wherein the S atom is replaced by another hetero atom, hereinafter referred to as "$T^1$-BTZ-$T^2$ unit". The $T^1$-BTZ-$T^2$ unit is characterized by a "double" asymmetric nature with two centres of asymmetry, a first one because the BTZ is only monosubstituted by F or Cl, and a second one because the BTZ group is sandwiched by two thiophene rings $T^1$ and $T^2$ only one of which is substituted while the other is unsubstituted. The $T^1$-BTZ-$T^2$ unit is further characterized in that the F or Cl atom on the BTZ group is in ortho-position to the unsubstituted thiophene ring. The asymmetric structure of the $T^1$-BTZ-$T^2$ unit creates intrinsic randomness in the polymer backbone.

It was surprisingly found that, when using a polymer according to the invention as donor component in the photoactive layer of a BHJ OPV cell, the specific substitution pattern of the asymmetrically substituted $T^1$-BTZ-$T^2$ unit plays an important role regarding the morphology of the bulk heterojunction, and leads to unexpected advantageous effects when being used as semiconductor in electronic or optoelectronic devices.

D. Mo et al., *Chem. Mater.* 2017, 29, 2819 disclose the following polymers

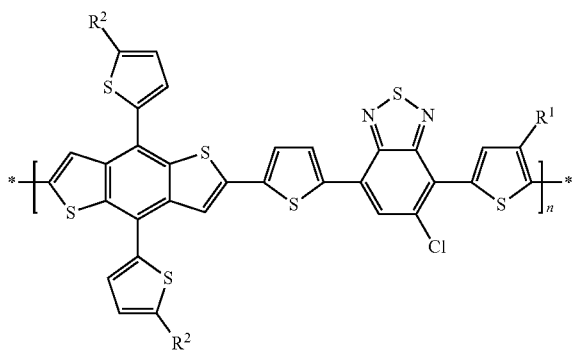

wherein $R^1$ is ether dodecyl or 2-ethylhexyl, and $R^2$ is either 2-hexyldecyl or 2-butyloctyl, and their use as donor material in the photoactive layer of an organic solar cell.

In contrast to the polymer of the present invention, the polymer disclosed by Mo et al. contains a $T^1$-BTZ-$T^2$ unit having a different substitution pattern, wherein the chloro atom on the BTZ group is in ortho-position to the substituted thiophene ring.

It could be demonstrated by comparison experiments that the polymer according to the present invention with its different substitution pattern, when used in the photoactive layer of an OPV cell, leads to significant improvements, for example an increase in fill factor and power conversion efficiency (PCE), compared to the polymers as disclosed by Mo et al.

WO 2012/054910 A1 discloses polymers of the following formula

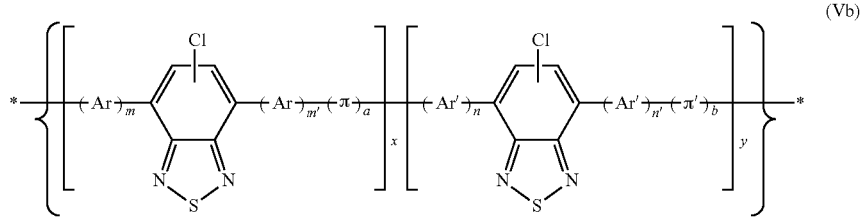

wherein Ar and Ar' are optionally substituted heteroaryl groups, and π and π' are optionally substituted polycyclic aryl or heteroaryl groups, and their use in electronic devices like photovoltaic cells or transistors. However, it does not disclose or suggest polymers comprising a T-BTZ-T unit with asymmetric structure as disclosed and claimed hereinafter, or the advantageous effects thereby achieved.

SUMMARY

The invention relates to a conjugated polymer of formula I wherein the individual radicals, independently of each other and on each occurrence identically or differently, have the following meanings U S, Se or $NR^0$, preferably S, X F, Cl or CN, preferably F or Cl, very preferably Cl, $R^1$, $R^2$ H, F, $R^x$, —$OR^x$, —$SR^x$, —C(=O)$R^x$ or —C(=O)—$OR^x$, —S(=O)$_2R^x$, $R^3$, $R^4$ H, F, Cl, ON, $R^x$, —$OR^x$, —$SR^x$, —C(=O)$R^x$, —C(=O)—$OR^x$ or —S(=O)$_2R^x$, $R^5$ straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or CN, $R^x$ straight-chain, branched or cyclic alkyl with 1 to 30, preferably 1 to 20, C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F or CN, or aryl, heteroaryl, arylalkyl or heteroarylalkyl, wherein each of the aforementioned cyclic groups has 5 to 20 ring atoms, is mono- or polycyclic, does optionally contain fused rings, and is unsubstituted or substituted by one or more identical or different groups L, L F, Cl, —$NO_2$, —CN, —NC, —NCO, —NCS, —OCN, —SCN, $R^0$, $OR^0$, $SR^0$, —C(=O)$X^0$, —C(=O)$R^0$, —C(=O)—$OR^0$, —O—C(=O)—$R^0$, —$NH_2$, —$NHR^0$, —$NR^0R^{00}$, —C(=O)$NHR^0$, —C(=O)$NR^0R^{00}$, —$SO_3R^0$, —$SO_2R^0$, —OH, —$NO_2$, —$CF_3$, —$SF_5$, or optionally substituted silyl, or carbyl or hydrocarbyl with 1 to 40, preferably 1 to 30 C atoms that is optionally substituted and optionally comprises one or more hetero atoms, $Y^1$, $Y^2$ H, F, Cl or CN, $R^0$, $R^{00}$ H or straight-chain or branched alkyl with 1 to 30, preferably 1 to 20, C atoms that is optionally fluorinated,

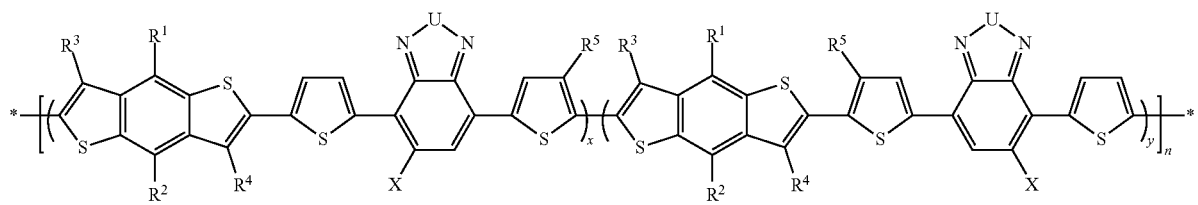

I

X⁰ halogen, preferably F or Cl,
x, y real numbers representing mole fractions, wherein $0<x<1$ and $0<y<1$, preferably $0.05 \leq x \leq 0.95$ and $0.05 \leq y \leq 0.95$, and x+y=1,
n an integer >1, preferably ≥10.

The invention further relates to the use of a conjugated polymer of formula I as semiconductor, preferably as electron donor or p-type semiconductor, preferably in a semiconducting material, an electronic or optoelectronic device, or a component of an electronic or optoelectronic device.

The invention further relates to a composition comprising one or more conjugated polymers of formula I, and further comprising one or more compounds having one or more of a semiconducting, hole or electron transport, hole or electron blocking, insulating, binding, electrically conducting, photoconducting, photoactive or light emitting property.

The invention further relates to a composition comprising one or more conjugated polymers of formula I, and further comprising a binder, preferably an electrically inert binder, very preferably an electrically inert polymeric binder.

The invention further relates to a composition comprising a conjugated polymer of formula I, and further comprising one or more electron acceptors or n-type semiconductors, preferably selected from organic small molecules.

The invention further relates to a bulk heterojunction (BHJ) formed from a composition comprising a conjugated polymer of formula I as electron donor or p-type semiconductor, and one or more compounds which are electron acceptor or n-type semiconductors.

The invention further relates to the use of a conjugated polymer or a composition as described above and below as semiconducting, charge transporting, electrically conducting, photoconducting, photoactive or light emitting material.

The invention further relates to the use of a conjugated polymer or a composition as described above and below in an electronic or optoelectronic device, or in a component of such a device or in an assembly comprising such a device.

The invention further relates to a semiconducting, charge transporting, electrically conducting, photoconducting, photoactive or light emitting material, comprising a conjugated polymer or a composition as described above and below.

The invention further relates to an electronic or optoelectronic device, or a component thereof, or an assembly comprising it, which comprises a conjugated polymer or a composition as described above and below.

The invention further relates to an electronic or optoelectronic device, or a component thereof, or an assembly comprising it, which comprises a semiconducting, charge transporting, electrically conducting, photoconducting or light emitting material as described above and below.

The invention further relates to a formulation comprising a conjugated polymer or a composition as described above and below, and further comprising one or more solvents, preferably selected from organic solvents.

The invention further relates to the use of a formulation as described above and below for the preparation of an electronic or optoelectronic device or a component thereof.

The invention further relates to an electronic or optoelectronic device or a component thereof, which is obtained through the use of a formulation as described above and below.

The electronic or optoelectronic device includes, without limitation, organic field effect transistors (OFET), organic thin film transistors (OTFT), organic light emitting diodes (OLED), organic light emitting transistors (OLET), organic light emitting electrochemical cell (OLEC), organic photovoltaic devices (OPV), organic photodetectors (OPD), organic solar cells, dye-sensitized solar cells (DSSC), organic photoelectrochemical cells (OPEC), perovskite-based solar cells (PSCs), laser diodes, Schottky diodes, photoconductors, photodetectors and thermoelectric devices.

Preferred devices are OFETs, OTFTs, OPVs, PSCs, OPDs and OLEDs, in particular OPDs and BHJ OPVs or inverted BHJ OPVs.

The component of the electronic or optoelectronic device includes, without limitation, charge injection layers, charge transport layers, interlayers, planarising layers, antistatic films, printed polarizers, polymer electrolyte membranes (PEM), conducting substrates and conducting patterns.

The assembly comprising an electronic or optoelectronic device includes, without limitation, integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

In addition the conjugated polymer or composition as described above and below can be used as electrode material in batteries, or in components or devices for detecting and discriminating DNA sequences.

Terms and Definitions

As used herein, the term "polymer" will be understood to mean a molecule of high relative molecular mass, the structure of which essentially comprises multiple repetitions of units derived, actually or conceptually, from molecules of low relative molecular mass (*Pure Appl. Chem.*, 1996, 68, 2291). The term "oligomer" will be understood to mean a molecule of intermediate relative molecular mass, the structure of which essentially comprises a small plurality of units derived, actually or conceptually, from molecules of lower relative molecular mass (*Pure Appl. Chem.*, 1996, 68, 2291). In a preferred meaning as used herein present invention a polymer will be understood to mean a compound having >1, i.e. at least 2 repeat units, preferably ≥5 repeat units, very preferably ≥10 repeat units, and an oligomer will be understood to mean a compound with >1 and <10, preferably >1 and <5, repeat units.

Further, as used herein, the term "polymer" will be understood to mean a molecule that encompasses a backbone (also referred to as "main chain") of one or more distinct types of repeat units (the smallest constitutional unit of the molecule) and is inclusive of the commonly known terms "oligomer", "copolymer", "homopolymer", "random polymer" and the like. Further, it will be understood that the term polymer is inclusive of, in addition to the polymer itself, residues from initiators, catalysts and other elements attendant to the synthesis of such a polymer, where such residues are understood as not being covalently incorporated thereto. Further, such residues and other elements, while normally removed during post polymerization purification processes, are typically mixed or co-mingled with the polymer such that they generally remain with the polymer when it is transferred between vessels or between solvents or dispersion media.

As used herein, in a formula showing a polymer or a repeat unit, like for example a polymer of formula I or P or their subformulae, an asterisk (*) will be understood to mean a chemical linkage to an adjacent unit or to a terminal group in the polymer backbone. In a ring, like for example a benzene or thiophene ring, an asterisk (*) will be understood to mean a C atom that is fused to an adjacent ring.

As used herein, the terms "repeat unit", "repeating unit" and "monomeric unit" are used interchangeably and will be understood to mean the constitutional repeating unit (CRU), which is the smallest constitutional unit the repetition of which constitutes a regular macromolecule, a regular oligomer molecule, a regular block or a regular chain (*Pure Appl. Chem.*, 1996, 68, 2291). As further used herein, the term "unit" will be understood to mean a structural unit which can be a repeating unit on its own, or can together with other units form a constitutional repeating unit.

As used herein, a "terminal group" will be understood to mean a group that terminates a polymer backbone. The expression "in terminal position in the backbone" will be understood to mean a divalent unit or repeat unit that is linked at one side to such a terminal group and at the other side to another repeat unit. Such terminal groups include endcap groups, or reactive groups that are attached to a monomer forming the polymer backbone which did not participate in the polymerization reaction, like for example a group having the meaning of $R^{31}$ or $R^{32}$ as defined below.

As used herein, the term "endcap group" will be understood to mean a group that is attached to, or replacing, a terminal group of the polymer backbone. The endcap group can be introduced into the polymer by an endcapping process. Endcapping can be carried out for example by reacting the terminal groups of the polymer backbone with a monofunctional compound ("endcapper") like for example an alkyl- or arylhalide, an alkyl- or arylstannane or an alkyl- or arylboronate. The endcapper can be added for example after the polymerization reaction. Alternatively the endcapper can be added in situ to the reaction mixture before or during the polymerization reaction. In situ addition of an endcapper can also be used to terminate the polymerization reaction and thus control the molecular weight of the forming polymer. Typical endcap groups are for example H, phenyl and lower alkyl.

As used herein, the term "small molecule" will be understood to mean a monomeric compound which typically does not contain a reactive group by which it can be reacted to form a polymer, and which is designated to be used in monomeric form. In contrast thereto, the term "monomer" unless stated otherwise will be understood to mean a monomeric compound that carries one or more reactive functional groups by which it can be reacted to form a polymer.

As used herein, the terms "donor" or "donating" and "acceptor" or "accepting" will be understood to mean an electron donor or electron acceptor, respectively. "Electron donor" will be understood to mean a chemical entity that donates electrons to another compound or another group of atoms of a compound. "Electron acceptor" will be understood to mean a chemical entity that accepts electrons transferred to it from another compound or another group of atoms of a compound. See also International Union of Pure and Applied Chemistry, Compendium of Chemical Technology, Gold Book, Version 2.3.2, 19. August 2012, pages 477 and 480.

As used herein, the term "n-type" or "n-type semiconductor" will be understood to mean an extrinsic semiconductor in which the conduction electron density is in excess of the mobile hole density, and the term "p-type" or "p-type semiconductor" will be understood to mean an extrinsic semiconductor in which mobile hole density is in excess of the conduction electron density (see also, J. Thewlis, *Concise Dictionary of Physics*, Pergamon Press, Oxford, 1973).

As used herein, the term "leaving group" will be understood to mean an atom or group (which may be charged or uncharged) that becomes detached from an atom in what is considered to be the residual or main part of the molecule taking part in a specified reaction (see also *Pure Appl. Chem.*, 1994, 66, 1134).

As used herein, the term "conjugated" will be understood to mean a compound (for example a polymer) that contains mainly C atoms with $sp^2$-hybridisation (or optionally also sp-hybridisation), and wherein these C atoms may also be replaced by hetero atoms. In the simplest case this is for example a compound with alternating C—C single and double (or triple) bonds, but is also inclusive of compounds with aromatic units like for example 1,4-phenylene. The term "mainly" in this connection will be understood to mean that a compound with naturally (spontaneously) occurring defects, or with defects included by design, which may lead to interruption of the conjugation, is still regarded as a conjugated compound.

As used herein, unless stated otherwise the molecular weight is given as the number average molecular weight $M_n$ or weight average molecular weight Mw, which is determined by gel permeation chromatography (GPC) against polystyrene standards in eluent solvents such as tetrahydrofuran, trichloromethane (TCM, chloroform), chlorobenzene or 1,2,4-trichloro-benzene. Unless stated otherwise, chlorobenzene is used as solvent. The degree of polymerization, also referred to as total number of repeat units, n, will be understood to mean the number average degree of polymerization given as $n=M_n/M_U$, wherein $M_n$ is the number average molecular weight and $M_U$ is the molecular weight of the single repeat unit, see J. M. G. Cowie, *Polymers: Chemistry & Physics of Modern Materials*, Blackie, Glasgow, 1991.

As used herein, the term "carbyl group" will be understood to mean any monovalent or multivalent organic moiety which comprises at least one carbon atom either without any non-carbon atoms (like for example —C≡C—), or optionally combined with at least one non-carbon atom such as B, N, O, S, P, Si, Se, As, Te or Ge (for example carbonyl etc.).

As used herein, the term "hydrocarbyl group" will be understood to mean a carbyl group that does additionally contain one or more H atoms and optionally contains one or more hetero atoms like for example B, N, O, S, P, Si, Se, As, Te or Ge.

As used herein, the term "hetero atom" will be understood to mean an atom in an organic compound that is not a H- or C-atom, and preferably will be understood to mean B, N, O, S, P, Si, Se, As, Te or Ge.

A carbyl or hydrocarbyl group comprising a chain of 3 or more C atoms may be straight-chain, branched and/or cyclic, and may include spiro-connected and/or fused rings.

Preferred carbyl and hydrocarbyl groups include alkyl, alkoxy, thioalkyl, alkylcarbonyl, alkoxycarbonyl, alkylcarbonyloxy and alkoxycarbonyloxy, each of which is optionally substituted and has 1 to 40, preferably 1 to 25, very preferably 1 to 18 C atoms, furthermore optionally substituted aryl or aryloxy having 6 to 40, preferably 6 to 25 C atoms, furthermore alkylaryloxy, arylcarbonyl, aryloxycarbonyl, arylcarbonyloxy and aryloxycarbonyloxy, each of which is optionally substituted and has 6 to 40, preferably 7 to 40 C atoms, wherein all these groups do optionally contain one or more hetero atoms, preferably selected from B, N, O, S, P, Si, Se, As, Te and Ge.

Further preferred carbyl and hydrocarbyl group include for example: a $C_1$-$C_{40}$ alkyl group, a $C_1$-$C_{40}$ fluoroalkyl group, a $C_1$-$C_{40}$ alkoxy or oxaalkyl group, a $C_2$-$C_{40}$ alkenyl group, a $C_2$-$C_{40}$ alkynyl group, a $C_3$-$C_{40}$ allyl group, a $C_4$-$C_{40}$ alkyldienyl group, a $C_4$-$C_{40}$ polyenyl group, a $C_2$-$C_{40}$ ketone group, a $C_2$-$C_{40}$ ester group, a $C_6$-$C_{18}$ aryl group, a $C_6$-$C_{40}$ alkylaryl group, a $C_6$-$C_{40}$ arylalkyl group, a $C_4$-$C_{40}$ cycloalkyl group, a $C_4$-$C_{40}$ cycloalkenyl group, and the like. Preferred among the foregoing groups are a $C_1$-$C_{20}$ alkyl group, a $C_1$-$C_{20}$ fluoroalkyl group, a $C_2$-$C_{20}$ alkenyl group, a $C_2$-$C_{20}$ alkynyl group, a $C_3$-$C_{20}$ allyl group, a $C_4$-$C_{20}$ alkyldienyl group, a $C_2$-$C_{20}$ ketone group, a $C_2$-$C_{20}$ ester group, a $C_6$-$C_{12}$ aryl group, and a $C_4$-$C_{20}$ polyenyl group, respectively.

Also included are combinations of groups having carbon atoms and groups having hetero atoms, like e.g. an alkynyl group, preferably ethynyl, that is substituted with a silyl group, preferably a trialkylsilyl group.

The carbyl or hydrocarbyl group may be an acyclic group or a cyclic group.

Where the carbyl or hydrocarbyl group is an acyclic group, it may be straight-chain or branched. Where the carbyl or hydrocarbyl group is a cyclic group, it may be a non-aromatic carbocyclic or heterocyclic group, or an aryl or heteroaryl group.

A non-aromatic carbocyclic group as referred to above and below is saturated or unsaturated and preferably has 4 to 30 ring C atoms. A non-aromatic heterocyclic group as referred to above and below preferably has 4 to 30 ring C atoms, wherein one or more of the C ring atoms are optionally replaced by a hetero atom, preferably selected from N, O, S, Si and Se, or by a —S(O)— or —S(O)$_2$— group. The non-aromatic carbo- and heterocyclic groups are mono- or polycyclic, may also contain fused rings, preferably contain 1, 2, 3 or 4 fused or unfused rings, and are optionally substituted with one or more groups L, wherein L is selected from F, Cl, —CN, —NC, —NCO, —NCS, —OCN, —SCN, —R$^0$, —OR$^0$, —SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O) NR$^0$R$^{00}$, —SO$_3$R, —SO$_2$R, —OH, —NO$_2$, —CF$_3$, —SF$_5$, or optionally substituted silyl, or carbyl or hydrocarbyl with 1 to 30, preferably 1 to 20 C atoms that is optionally substituted and optionally comprises one or more hetero atoms, wherein X$^0$ is halogen, preferably F or Cl, and R$^0$, R$^{00}$ denote H or straight-chain or branched alkyl with 1 to 24, preferably 1 to 12 C atoms that is optionally fluorinated, preferably L is a $C_{1-24}$ alkyl chain selected from formulae SUB1-6 as defined below that is optionally fluorinated.

Preferably L is selected from F, —CN, —R$^0$, —OR$^0$, —SR$^0$, —C(=O)—R$^0$, —C(=O)—OR$^0$, —O—C(=O)—R$^0$, —O—C(=O)—OR$^0$, —C(=O)—NHR$^0$ and —C(=O)—NR$^0$R$^{00}$.

Further preferably L is selected from F or alkyl, alkoxy, oxaalkyl, thioalkyl, fluoroalkyl, fluoroalkoxy, alkylcarbonyl, alkoxycarbonyl, with 1 to 12 C atoms, or alkenyl or alkynyl with 2 to 12 C atoms or a $C_{1-24}$ alkyl chain selected from formulae SUB1-6 as defined below that is optionally fluorinated.

Preferred non-aromatic carbocyclic or heterocyclic groups are tetrahydrofuran, indane, pyran, pyrrolidine, piperidine, cyclopentane, cyclohexane, cycloheptane, cyclopentanone, cyclohexanone, dihydro-furan-2-one, tetrahydro-pyran-2-one and oxepan-2-one.

An aryl group as referred to above and below preferably has 4 to 30 ring C atoms, is mono- or polycyclic and may also contain fused rings, preferably contains 1, 2, 3 or 4 fused or unfused rings, and is optionally substituted with one or more groups L as defined above.

A heteroaryl group as referred to above and below preferably has 4 to 30 ring C atoms, wherein one or more of the C ring atoms are replaced by a hetero atom, preferably selected from N, O, S, Si and Se, is mono- or polycyclic and may also contain fused rings, preferably contains 1, 2, 3 or 4 fused or unfused rings, and is optionally substituted with one or more groups L as defined above.

An arylalkyl or heteroarylalkyl group as referred to above and below preferably denotes —(CH$_2$)$_a$-aryl or —(CH$_2$)$_a$-heteroaryl, wherein a is an integer from 1 to 6, preferably 1, and "aryl" and "heteroaryl" have the meanings given above and below. A preferred arylalkyl group is benzyl which is optionally substituted by L.

As used herein, "arylene" will be understood to mean a divalent aryl group, and "heteroarylene" will be understood to mean a divalent heteroaryl group, including all preferred meanings of aryl and heteroaryl as given above and below.

Preferred aryl and heteroaryl groups are phenyl in which, in addition, one or more CH groups may be replaced by N, naphthalene, thiophene, selenophene, thienothiophene, dithienothiophene, fluorene and oxazole, all of which can be unsubstituted, mono- or polysubstituted with L as defined above. Very preferred aryl and heteroaryl groups are selected from pyrrole, preferably N-pyrrole, furan, pyridine, preferably 2- or 3-pyridine, pyrimidine, pyridazine, pyrazine, triazole, tetrazole, pyrazole, imidazole, isothiazole, thiazole, thiadiazole, isoxazole, oxazole, oxadiazole, thiophene, preferably 2-thiophene or 2,5-dithiophene-2',5'-diyl, selenophene, preferably 2-selenophene, thieno[3,2-b]thiophene, thieno[2,3-b]thiophene, furo[3,2-b]furan, furo[2,3-b]furan, seleno[3,2-b]selenophene, seleno[2,3-b]selenophene, thieno [3,2-b]selenophene, thieno[3,2-b]furan, indole, isoindole, benzo[b]furan, benzo[b]thiophene, benzo[1,2-b;4,5-b']dithiophene, benzo[2,1-b;3,4-b']dithiophene, quinole, 2-methylquinole, isoquinole, quinoxaline, quinazoline, benzotriazole, benzimidazole, benzothiazole, benzisothiazole, benzisoxazole, benzoxadiazole, benzoxazole, benzothiadiazole, 4H-cyclopenta[2,1-b;3,4-b']dithiophene, 7H-3,4-dithia-7-sila-cyclopenta[a]pentalene, all of which can be unsubstituted, mono- or polysubstituted with L as defined above. Further examples of aryl and heteroaryl groups are those selected from the groups shown hereinafter.

An alkyl group or an alkoxy group, i.e., where the terminal CH$_2$ group is replaced by —O—, can be straight-chain or branched. It is preferably straight-chain, has 2, 3, 4, 5, 6, 7, 8, 12 or 16 carbon atoms and accordingly is preferably ethyl, propyl, butyl, pentyl, hexyl, heptyl, octyl, dodecyl or hexadecyl, ethoxy, propoxy, butoxy, pentoxy, hexoxy, heptoxy, octoxy, dodecoxy or hexadecoxy, furthermore methyl, nonyl, decyl, undecyl, tridecyl, tetradecyl, pentadecyl, nonoxy, decoxy, undecoxy, tridecoxy or tetradecoxy, for example.

An alkenyl group, i.e., wherein one or more CH$_2$ groups are replaced by —CH=CH— can be straight-chain or branched. It is preferably straight-chain, has 2 to 10 C atoms and accordingly is preferably vinyl, prop-1-, or prop-2-enyl, but-1-, 2- or but-3-enyl, pent-1-, 2-, 3- or pent-4-enyl, hex-1-, 2-, 3-, 4- or hex-5-enyl, hept-1-, 2-, 3-, 4-, 5- or hept-6-enyl, oct-1-, 2-, 3-, 4-, 5-, 6- or oct-7-enyl, non-1-, 2-, 3-, 4-, 5-, 6-, 7- or non-8-enyl, dec-1-, 2-, 3-, 4-, 5-, 6-, 7-, 8- or dec-9-enyl.

Especially preferred alkenyl groups are $C_2$-$C_7$-1E-alkenyl, $C_4$-$C_7$-3E-alkenyl, $C_5$-$C_7$-4-alkenyl, $C_6$-$C_7$-5-alkenyl and $C_7$-6-alkenyl, in particular $C_2$-$C_7$-1E-alkenyl, $C_4$-$C_7$-3E-alkenyl and $C_5$-$C_7$-4-alkenyl. Examples for particularly preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, 4Z-heptenyl, 5-hexenyl, 6-heptenyl and the like. Groups having up to 5 C atoms are generally preferred.

An oxaalkyl group, i.e., where one CH₂ group is replaced by —O—, is preferably straight-chain 2-oxapropyl (=methoxymethyl), 2-(=ethoxymethyl) or 3-oxabutyl (=2-methoxyethyl), 2-, 3-, or 4-oxapentyl, 2-, 3-, 4-, or 5-oxahexyl, 2-, 3-, 4-, 5-, or 6-oxaheptyl, 2-, 3-, 4-, 5-, 6- or 7-oxaoctyl, 2-, 3-, 4-, 5-, 6-, 7- or 8-oxanonyl or 2-, 3-, 4-, 5-, 6-, 7-, 8- or 9-oxadecyl, for example.

In an alkyl group wherein one CH₂ group is replaced by —O— and one CH₂ group is replaced by —C(O)—, these radicals are preferably neighboured. Accordingly these radicals together form a carbonyloxy group —C(O)—O— or an oxycarbonyl group —O—C(O)—. Preferably this group is straight-chain and has 2 to 6 C atoms. It is accordingly preferably acetyloxy, propionyloxy, butyryloxy, pentanoyloxy, hexanoyloxy, acetyloxymethyl, propionyloxymethyl, butyryloxymethyl, pentanoyloxymethyl, 2-acetyloxyethyl, 2-propionyloxyethyl, 2-butyryloxyethyl, 3-acetyloxypropyl, 3-propionyloxypropyl, 4-acetyloxybutyl, methoxycarbonyl, ethoxycarbonyl, propoxycarbonyl, butoxycarbonyl, pentoxycarbonyl, methoxycarbonylmethyl, ethoxycarbonylmethyl, propoxycarbonylmethyl, butoxycarbonylmethyl, 2-(methoxycarbonyl)ethyl, 2-(ethoxycarbonyl)ethyl, 2-(propoxycarbonyl)ethyl, 3-(methoxycarbonyl)propyl, 3-(ethoxycarbonyl)propyl, 4-(methoxycarbonyl)-butyl.

An alkyl group wherein two or more CH₂ groups are replaced by —O— and/or —C(O)O— can be straight-chain or branched. It is preferably straight-chain and has 3 to 12 C atoms. Accordingly, it is preferably bis-carboxy-methyl, 2,2-bis-carboxy-ethyl, 3,3-bis-carboxy-propyl, 4,4-bis-carboxy-butyl, 5,5-bis-carboxy-pentyl, 6,6-bis-carboxy-hexyl, 7,7-bis-carboxy-heptyl, 8,8-bis-carboxy-octyl, 9,9-bis-carboxy-nonyl, 10,10-bis-carboxy-decyl, bis-(methoxycarbonyl)-methyl, 2,2-bis-(methoxycarbonyl)-ethyl, 3,3-bis-(methoxycarbonyl)-propyl, 4,4-bis-(methoxycarbonyl)-butyl, 5,5-bis-(methoxycarbonyl)-pentyl, 6,6-bis-(methoxycarbonyl)-hexyl, 7,7-bis-(methoxycarbonyl)-heptyl, 8,8-bis-(methoxycarbonyl)-octyl, bis-(ethoxycarbonyl)-methyl, 2,2-bis-(ethoxycarbonyl)-ethyl, 3,3-bis-(ethoxycarbonyl)-propyl, 4,4-bis-(ethoxycarbonyl)-butyl, 5,5-bis-(ethoxycarbonyl)-hexyl.

A thioalkyl group, i.e., where one CH₂ group is replaced by —S—, is preferably straight-chain thiomethyl (—SCH₃), 1-thioethyl (—SCH₂CH₃), 1-thiopropyl (=—SCH₂CH₂CH₃), 1-(thiobutyl), 1-(thiopentyl), 1-(thiohexyl), 1-(thioheptyl), 1-(thiooctyl), 1-(thiononyl), 1-(thiodecyl), 1-(thioundecyl) or 1-(thiododecyl), wherein preferably the CH₂ group adjacent to the sp² hybridised vinyl carbon atom is replaced.

A fluoroalkyl group can either be perfluoroalkyl $C_iF_{2i+1}$, wherein i is an integer from 1 to 15, in particular $CF_3$, $C_2F_5$, $C_3F_7$, $C_4F_9$, $C_5F_{11}$, $C_6F_{13}$, $C_7F_{15}$ or $C_8F_{17}$, very preferably $C_6F_{13}$, or partially fluorinated alkyl, preferably with 1 to 15 C atoms, in particular 1,1-difluoroalkyl, all of the aforementioned being straight-chain or branched.

Preferably "fluoroalkyl" means a partially fluorinated (i.e. not perfluorinated) alkyl group.

Alkyl, alkoxy, alkenyl, oxaalkyl, thioalkyl, carbonyl and carbonyloxy groups can be achiral or chiral groups. Particularly preferred chiral groups are 2-butyl (=1-methylpropyl), 2-methylbutyl, 2-methylpentyl, 3-methylpentyl, 2-ethylhexyl, 2-butyloctyl, 2-hexyldecyl, 2-octyldodecyl, 2-propylpentyl, in particular 2-methylbutyl, 2-methylbutoxy, 2-methylpentoxy, 3-methylpentoxy, 2-ethyl-hexoxy, 2-butyloctoxy, 2-hexyldecoxy, 2-octyldodecoxy, 1-methylhexoxy, 2-octyloxy, 2-oxa-3-methylbutyl, 3-oxa-4-methyl-pentyl, 4-methylhexyl, 2-hexyl, 2-octyl, 2-nonyl, 2-decyl, 2-dodecyl, 6-methoxy-octoxy, 6-methyloctoxy, 6-methyloctanoyloxy, 5-methylheptyloxy-carbonyl, 2-methylbutyryloxy, 3-methylvaleroyloxy, 4-methyl hexanoyloxy, 2-chloro-propionyloxy, 2-chloro-3-methylbutyryloxy, 2-chloro-4-methyl-valeryl-oxy, 2-chloro-3-methylvaleryloxy, 2-methyl-3-oxapentyl, 2-methyl-3-oxa-hexyl, 1-methoxypropyl-2-oxy, 1-ethoxypropyl-2-oxy, 1-propoxypropyl-2-oxy, 1-butoxypropyl-2-oxy, 2-fluorooctyloxy, 2-fluorodecyloxy, 1,1,1-trifluoro-2-octyloxy, 1,1,1-trifluoro-2-octyl, 2-fluoromethyloctyloxy for example. Very preferred are 2-ethylhexyl, 2-butyloctyl, 2-hexyldecyl, 2-octyldodecyl, 2-hexyl, 2-octyl, 2-octyloxy, 1,1,1-trifluoro-2-hexyl, 1,1,1-trifluoro-2-octyl and 1,1,1-trifluoro-2-octyloxy.

Preferred achiral branched groups are isopropyl, isobutyl (=methylpropyl), isopentyl (=3-methylbutyl), tert. butyl, isopropoxy, 2-methyl-propoxy and 3-methylbutoxy.

In a preferred embodiment, the substituents on an aryl or heteroaryl group as described above and below are independently of each other selected from primary, secondary or tertiary alkyl, alkoxy, oxaalkyl, thioalkyl, alkylcarbonyl or alkoxycarbonyl with 1 to 30 C atoms, wherein one or more H atoms are optionally replaced by F, or aryl, aryloxy, heteroaryl or heteroaryloxy that is optionally alkylated, alkoxylated, alkylthiolated or esterified and has 4 to 30 ring atoms. Further preferred substituents are selected from the group consisting of the following formulae

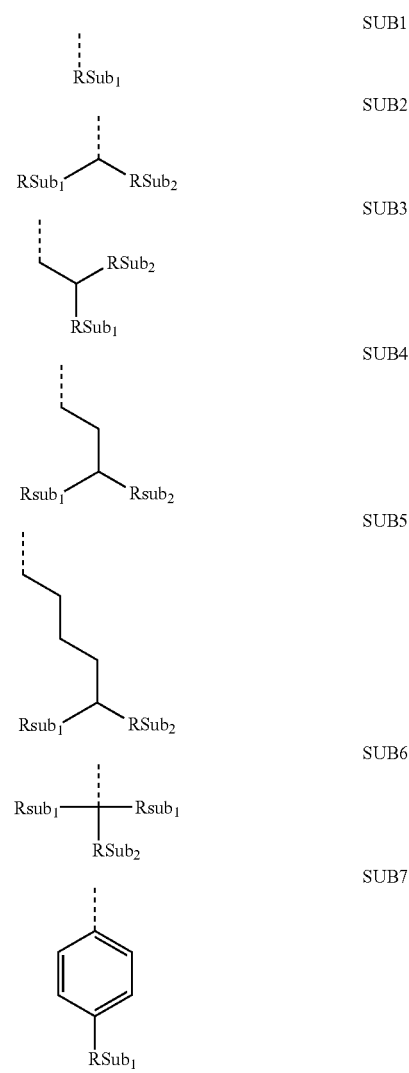

SUB8

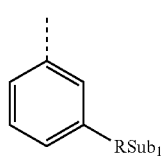

SUB9

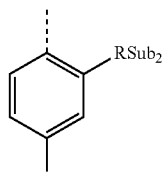

SUB10

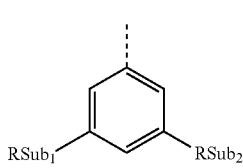

SUB11

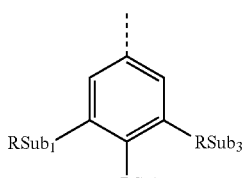

SUB12

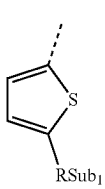

SUB13

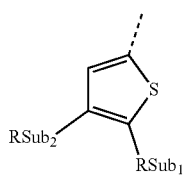

SUB14

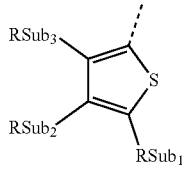

wherein $RSub_{1-3}$ denotes L as defined above and below and where at least one, preferably all groups $RSub_{1-3}$ are selected from alkyl, alkoxy, oxaalkyl, thioalkyl, alkylcarbonyl or alkoxycarbonyl with 1 to 24 C atoms, preferably 1 to 20 C atoms, that is optionally fluorinated, and wherein the dashed line denotes the link to the ring to which these groups are attached. Very preferred among these substituents are those wherein all $RSub_{1-3}$ subgroups are identical.

As used herein, if an aryl(oxy) or heteroaryl(oxy) group is "alkylated or alkoxylated", this means that it is substituted with one or more alkyl or alkoxy groups having from 1 to 20 C-atoms and being straight-chain or branched and wherein one or more H atoms are optionally substituted by an F atom.

Above and below, $Y^1$ and $Y^2$ are independently of each other H, F, Cl or CN.

As used herein, —CO—, —C(=O)— and —C(O)— will be understood to mean a carbonyl group, i.e. a group having the structure

As used herein $C=CR^1R^2$ will be understood to mean a group having the structure

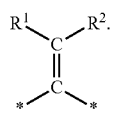

As used herein, "halogen" includes F, Cl, Br or I, preferably F, Cl or Br. A halogen atom that represents a substituent on a ring or chain is preferably F or Cl, very preferably F. A halogen atom that represents a reactive group in a monomer or an intermediate is preferably Br or I.

DETAILED DESCRIPTION

The polymers of the present invention are easy to synthesize and exhibit advantageous properties. They show good processibility for the device manufacture process, high solubility in organic solvents, and are especially suitable for large scale production using solution processing methods. In addition, they show a low bandgap, high charge carrier mobility, high external quantum efficiency in BHJ solar cells, good morphology when used in p/n-type blends e.g. with fullerenes, high oxidative stability, a long lifetime in electronic devices, and are promising materials for organic electronic OE devices, especially for OFETs and OPV cells with high power conversion efficiency.

The polymers of the present invention are suitable as p-type semiconductors for the preparation of blends of p-type and n-type semiconductors which are suitable for use in BHJ OPV devices.

Besides, the polymer of the present invention shows the following advantageous properties:

i) Compared to the polymers disclosed in prior art, the polymer of the present invention due to its specific substitution pattern on the T-BTZ-T core leads to different solubility and morphology profile, which has a positive impact on OPV performance and device fabrication.

ii) The change of the position of the halogen substituent influences the morphology without changing energetic properties of the polymer.

The inventors of the present invention have found that the double asymmetric nature of the $T^1$-BTZ-$T^2$ unit, wherein a monohalogenated BTZ group is flanked by a substituted and an unsubstituted thiophene ring $T^1$ and $T^2$, does not only create intrinsic randomness in the final polymer backbone, but does also have a significant effect on the morphology of the bulk heterojunction and the optoelectronic performance of the polymer, when being used together with an acceptor in the photoactive layer of an BHJ OPV cell.

The inventors of the present invention also found that the characteristic substitution pattern in the $T^1$-BTZ-$T^2$ unit, wherein the halogen atom on the BTZ group is in ortho-position to the adjacent unsubstituted thiophene ring leads to unexpected improvements when the polymer is used as donor the photoactive layer of a BHJ OPV cell, like a significant increase of the fill factor (FF) and power conversion efficiency (PCE). In contrast thereto, the polymer as disclosed in D. Mo et al., *Chem. Mater.* 2017, 29, 2819, which has a different substitution pattern, wherein the halogen atom on the BTZ group is in ortho-position to the adjacent substituted thiophene ring, shows lower FF and PCE values. These improvements were totally surprising and could not be expected from prior art.

In the polymer of formula I and its subformulae the total number of repeating units n is preferably from 2 to 10,000. Preferably n is ≥5, very preferably ≥10, most preferably ≥50, and preferably ≤500, very preferably ≤1,000, most preferably ≤2,000, including any combination of the aforementioned lower and upper limits of n.

Preferably the polymer of formula I is selected from the following subformulae

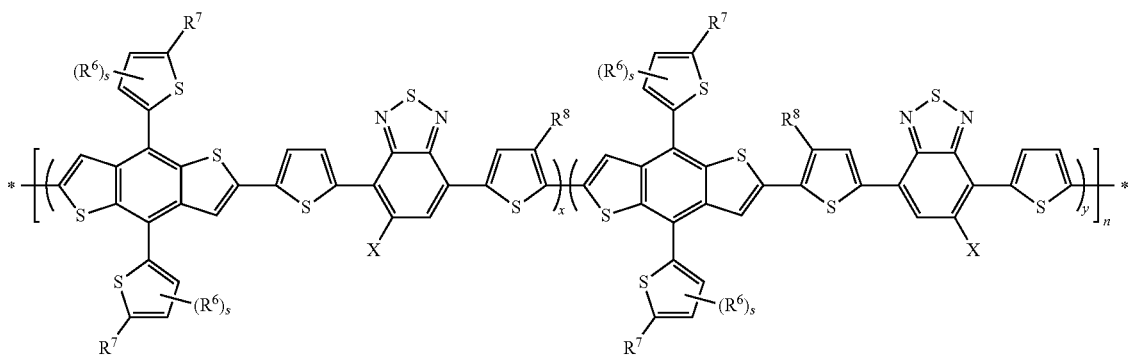

I1

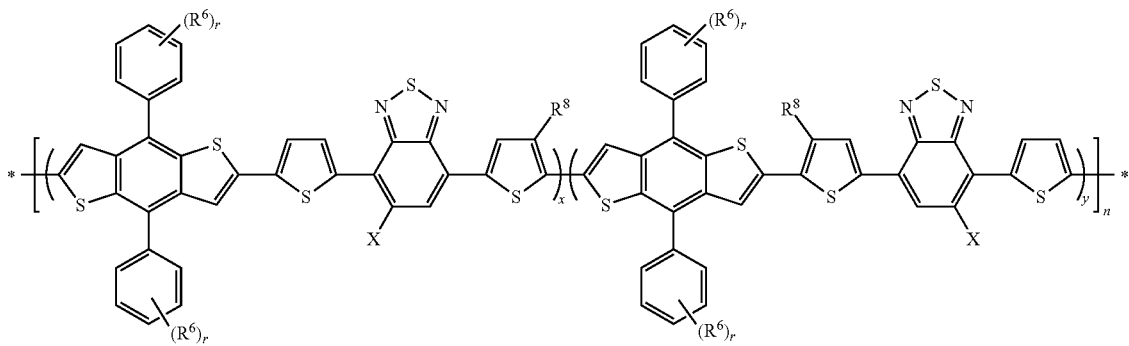

I2

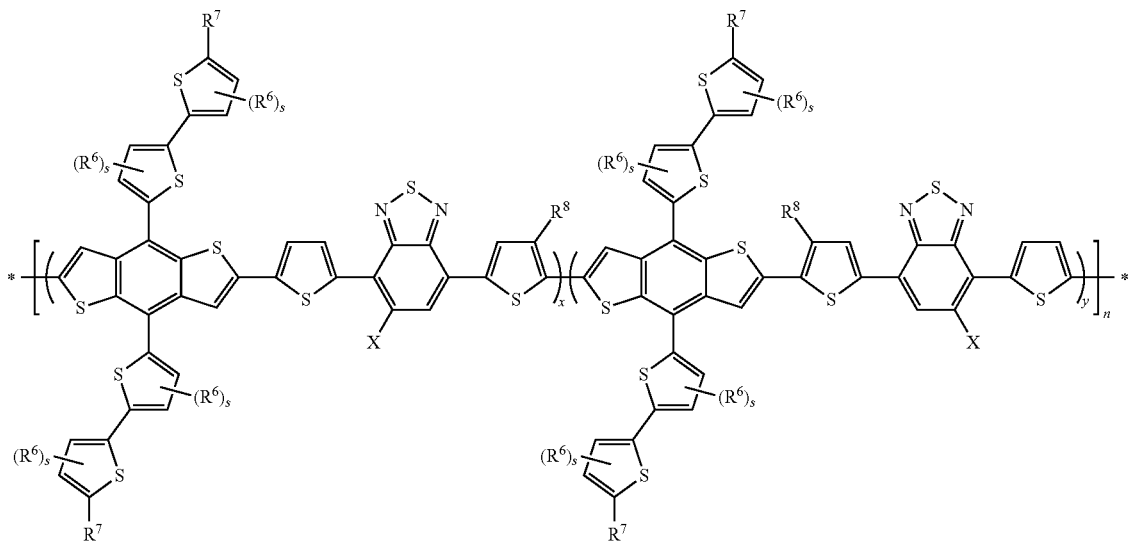

I3

-continued

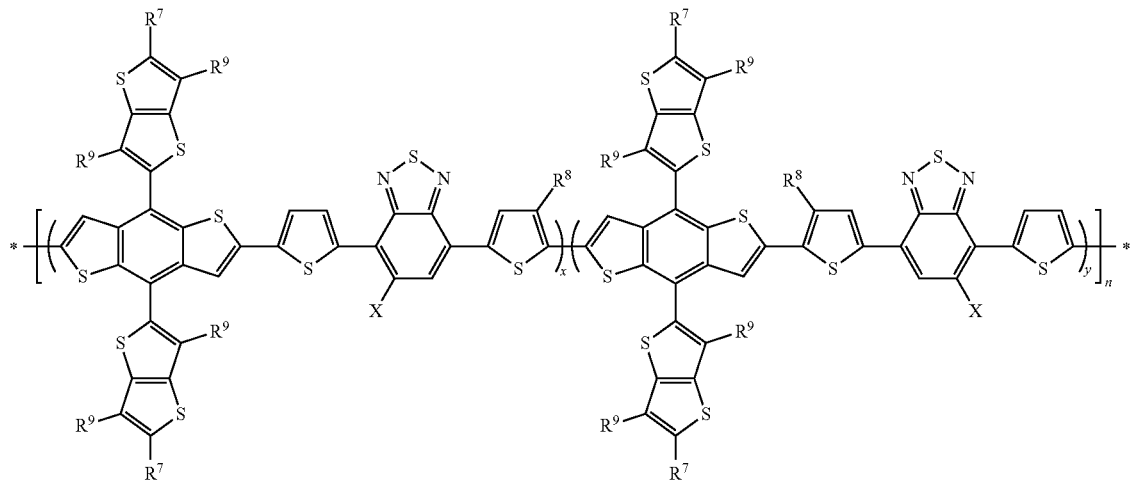

I4

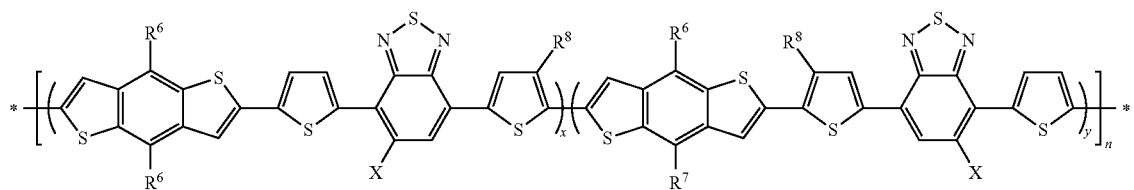

I5

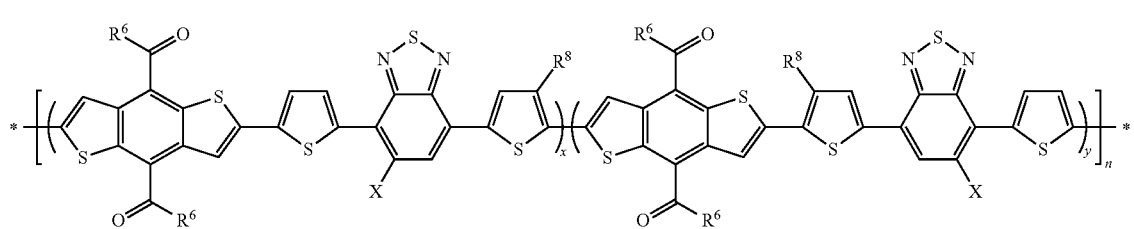

I6 wherein X, x, y and n are as defined in formula I, $R^6$, $R^7$ and $R^8$, independently of each other and on each occurrence identically or differently, denote alkyl, alkoxy or thioalkyl all of which are straight-chain having 1 to 24 C atoms or branched having 3 to 24 C atoms, and are optionally fluorinated, and are very preferably selected from formulae SUB1-SUB6 as defined above, $R^9$ is H or has one of the meanings given for $R^6$, r is 0, 1, 2 or 3, preferably 1, and s is 0, 1 or 2, preferably 0 or 1.

Especially preferred is a polymer of formula I1.

Very preferably the polymer of formula I is selected from the following subformulae

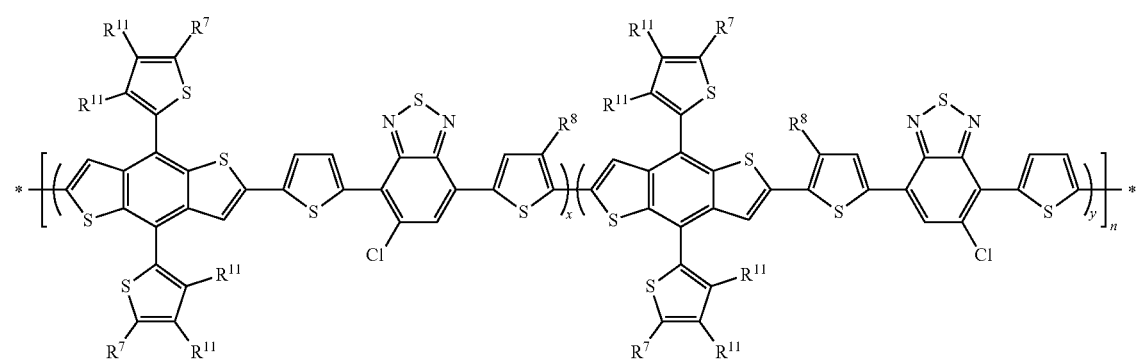

I1-1

I1-2
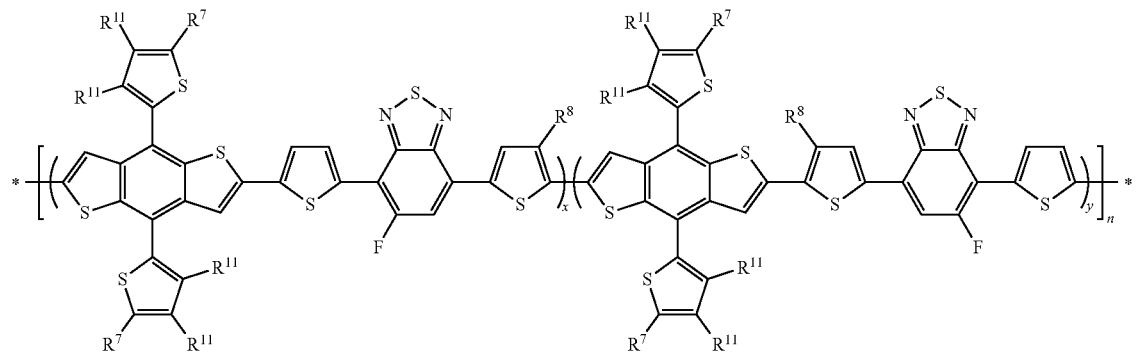
I2-1
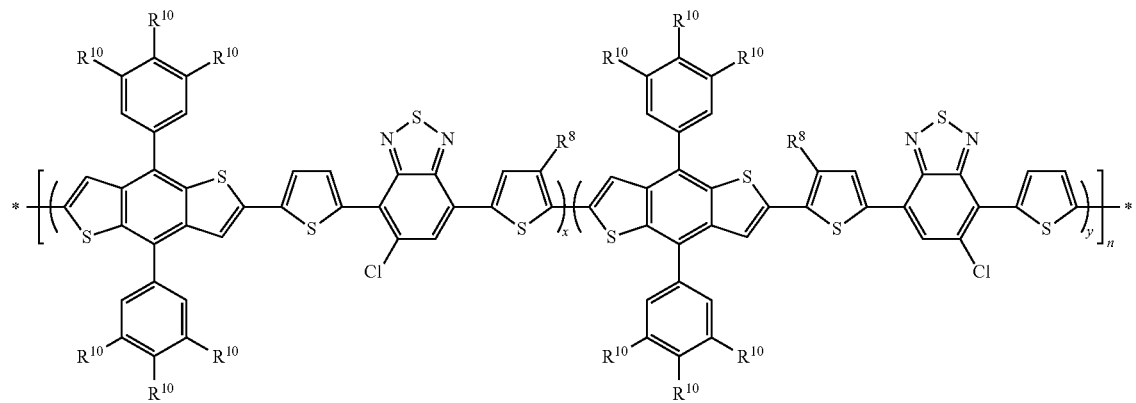
I2-2
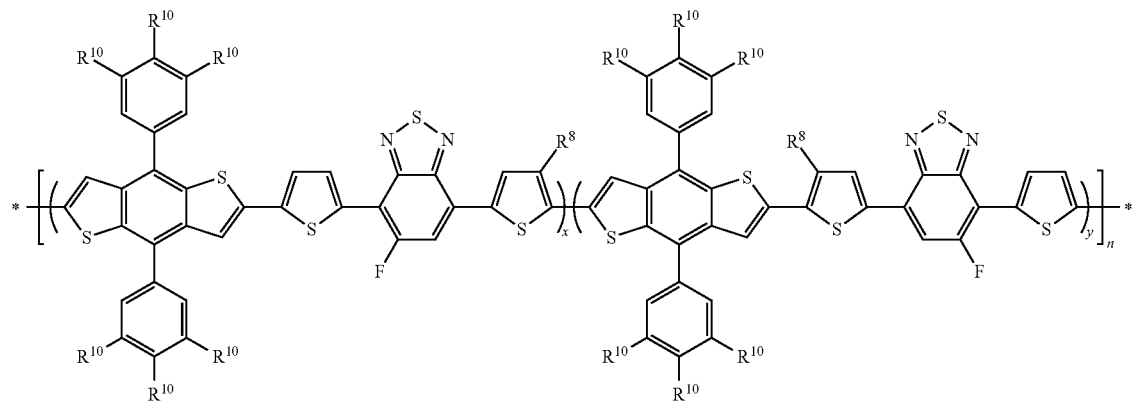

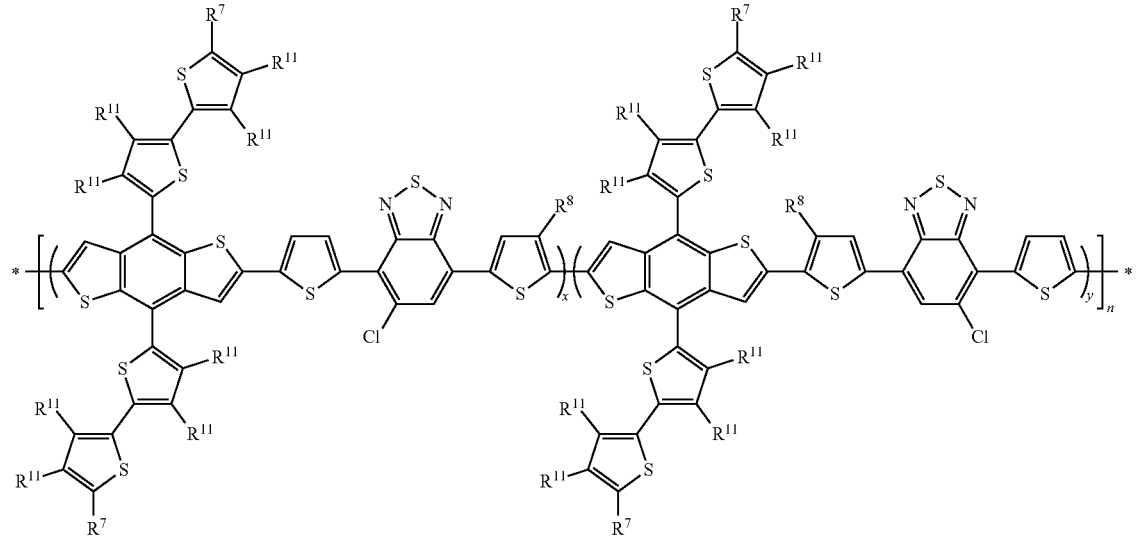
I3-1
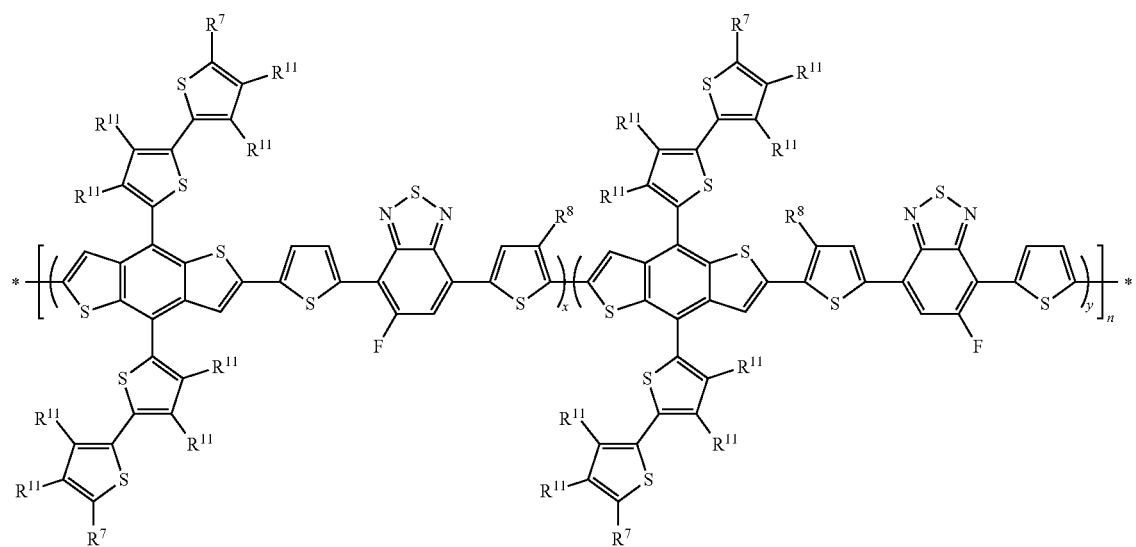
I3-2
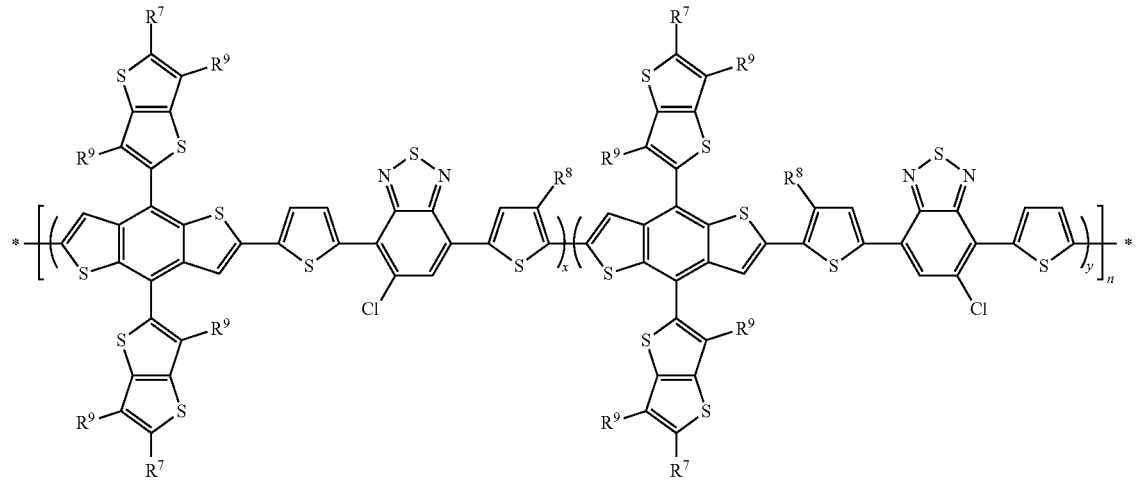
I4-1

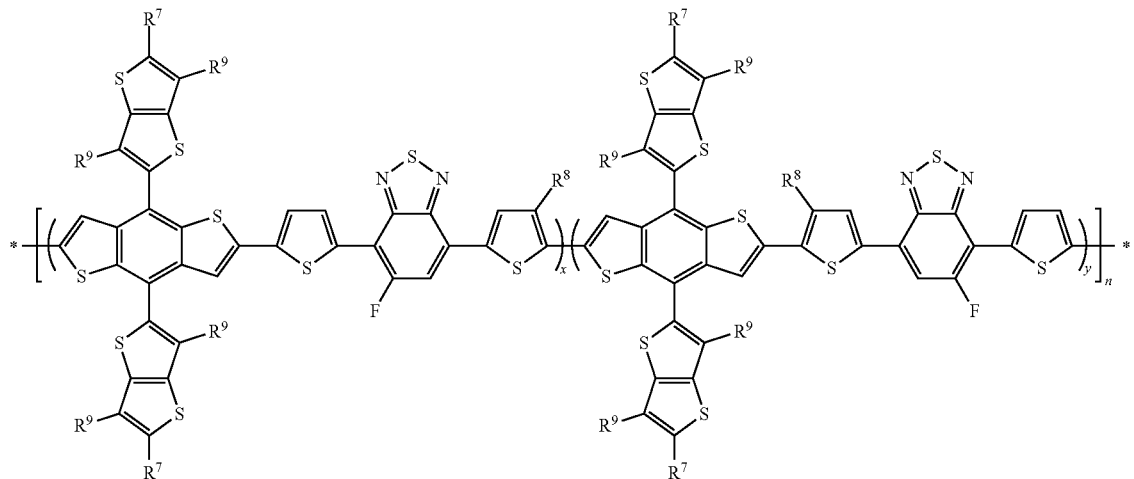

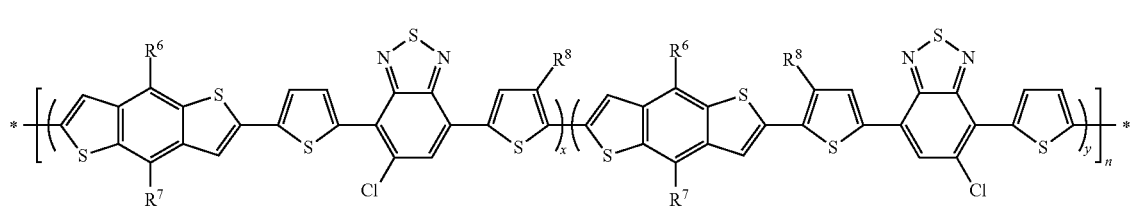

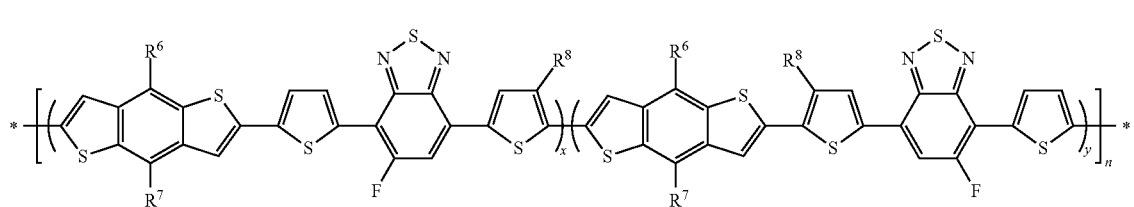

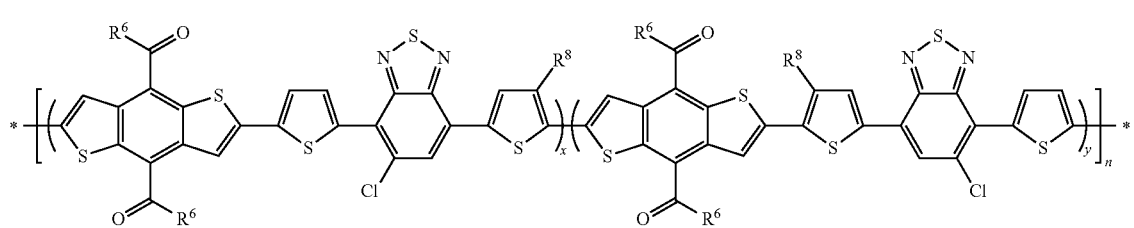

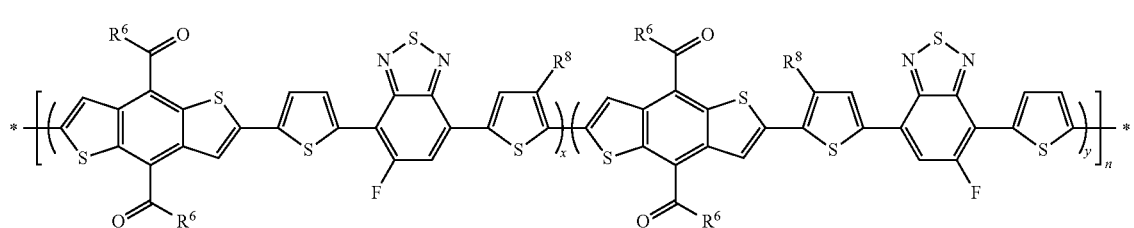

wherein x, y, n, $R^6$, $R^7$, $R^8$, $R^9$, r and s are as defined in formulae I1 to I6, and $R^{10}$ and $R^{11}$ have one of the meanings given for $R^6$ or denote H.

Especially preferred is a polymer of formula I1-1 or I1-2, most preferred a polymer of formula I1-1.

In formula I2-1 and I2-2 preferably at least one of $R^{10}$ is different from H.

In formula I3-1 and I3-2 preferably all of $R^{11}$ are H.

More preferably the polymer of formula I is selected from the following subformulae

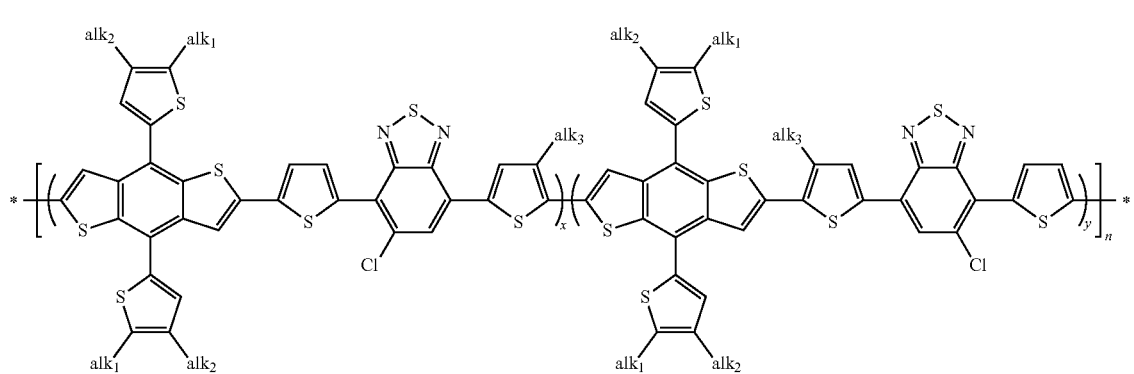
I1-1a
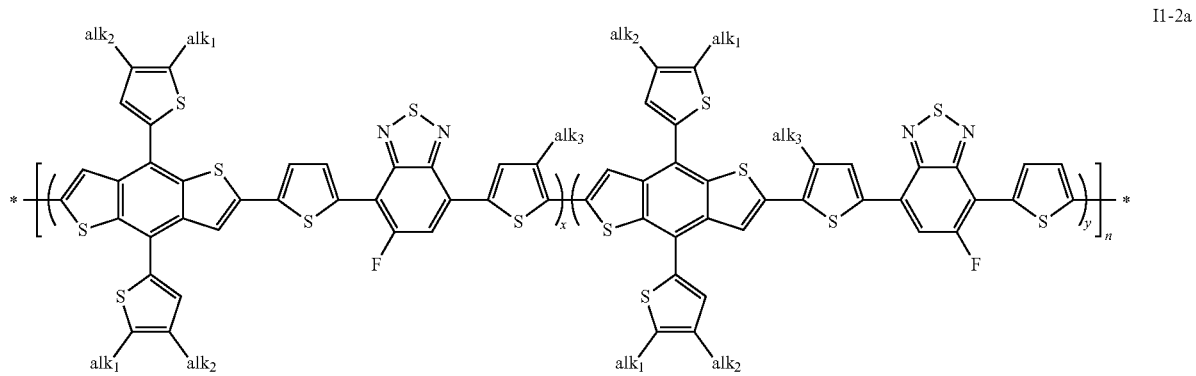
I1-2a
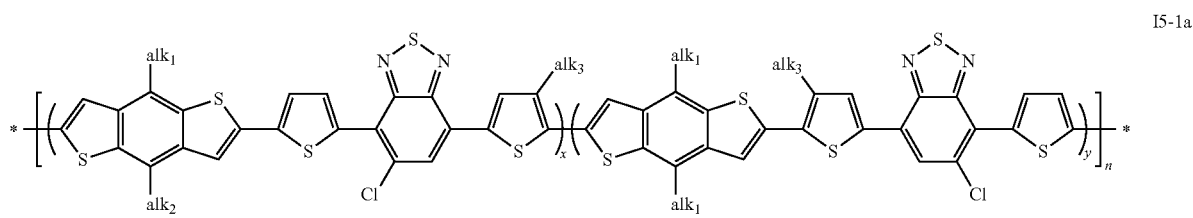
I5-1a
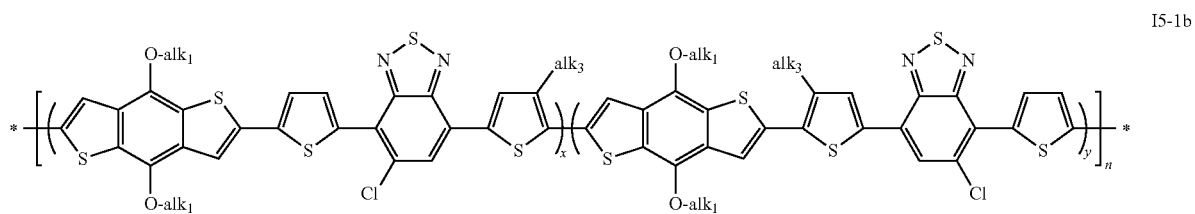
I5-1b
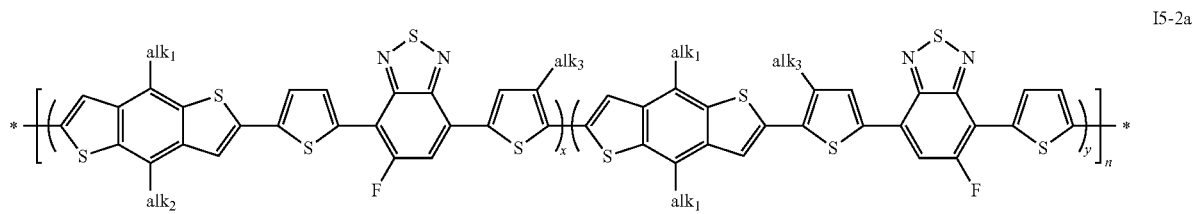
I5-2a
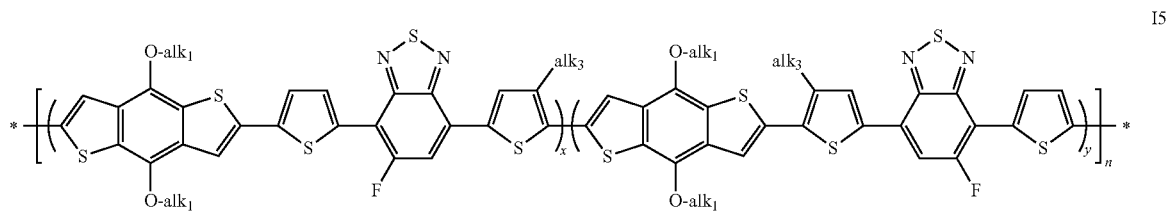
I5-2b -continued

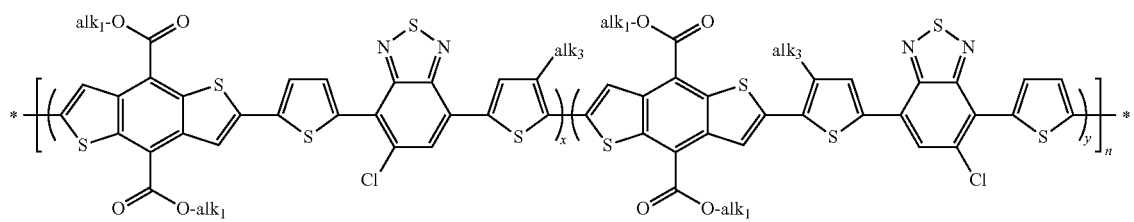

I6-1a

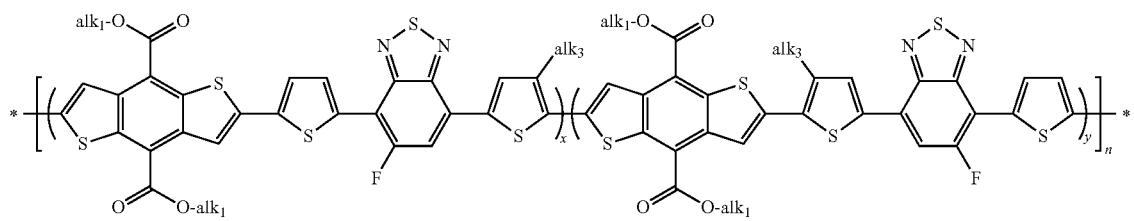

I6-2a wherein x, y and n are as defined above, "alk1", "alk2" and "alk3" denote alkyl that is straight-chain having 1 to 24 C atoms or branched having 3 to 24 C atoms, and is optionally fluorinated, "alk2" may also denote H. Therein, "alk1", and "alk2" when being different from H, are preferably selected from 2-octyldodecyl, 2-hexyldecyl, 2-butyloctyl, 1,3-dimethyloctyl or 2-ethylhexyl, and "alk3" is preferably selected from n-tetradecyl, n-dodecyl, 1,3-dimethyloctyl, 2-ethylhexyl or n-octyl, Especially preferred are polymers of formula I1-1a and I1-2a, very preferably wherein alk2 is H.

Further preferred is a polymer of formula P $$R^{31}\text{-chain-}R^{32} \quad P$$

wherein "chain" denotes a polymer chain of formula I, I1-I6 or I1a-I6a, and $R^{31}$ and $R^{32}$, independently of each other, H, $R^1$, $R^6$, F, Br, Cl, I, —$CH_2Cl$, —CHO, —CR'=CR''$_2$, —SiR'R''R''', —SiR'X'X'', —SiR'R''X''', —SnR'R''R''', —BR'R'', —B(OR')(OR''), —B(OH)$_2$, —O—SO$_2$—R', —C≡CH, —C≡C—SiR'$_3$, —ZnX' or an endcap group, X' and X'' denote halogen, R', R'' and R''' have independently of each other one of the meanings of $R^0$ given in formula I, and preferably denote alkyl with 1 to 12 C atoms, and two of R', R'' and R''' may also form a cyclosilyl, cyclostannyl, cycloborane or cycloboronate group with 2 to 20 C atoms together with the respective hetero atom to which they are attached.

Preferred endcap groups $R^{31}$ and $R^{32}$ are H, $C_{1-20}$ alkyl, or optionally substituted $C_{6-12}$ aryl or $C_{2-10}$ heteroaryl, very preferably H, phenyl or thiophene.

The invention further relates to a monomer of formula M

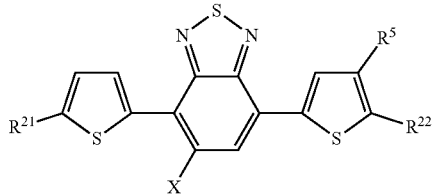

M wherein X is F or Cl, preferably Cl, $R^5$ has one of the meanings given in formula I or one of the preferred meanings given above and below, and $R^{21}$ and $R^{22}$ are independently of each other selected from the group consisting of an activated C—H bond, Cl, Br, I, O-tosylate, O-triflate, O-mesylate, O-nonaflate, —SiMe$_3$, —SiMe$_2$F, —SiMeF$_2$, —O—SO$_2Z^1$, —B(OZ$^2$)$_2$, —CZ$^3$=C(Z$^3$)$_2$, —C≡CH, —C≡CSi(Z$^1$)$_3$, —ZnX$^0$, —Mg—X$^0$ and —Sn(Z$^4$)$_3$, wherein $X^0$ is Cl, Br or I, $Z^{1-4}$ are selected from the group consisting of alkyl and aryl, preferably $C_{1-10}$ alkyl and $C_{6-12}$ aryl, each being optionally substituted, and two groups $Z^2$ may also form a cycloboronate group having 2 to 20 C atoms together with the B- and O-atoms.

Preferred polymers of formula I or P and their subformulae and monomers of formula M are selected from the following embodiments, including any combination thereof:

0.05≤x≤0.95 and 0.05≤y≤0.95, 0.25≤x≤0.75 and 0.25≤y≤0.75, 0.4≤x≤0.6 and 0.4≤y≤0.6, U is S, U is Se, U is NR$^0$, X is Cl, X is F, $R^x$ is selected from aryl, heteroaryl, arylalkyl or heteroarylalkyl, each of which has 5 to 20 ring atoms, optionally contains fused rings and is unsubstituted or substituted by one or more groups L as defined in formula I, $R^x$ is selected from alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated, $R^x$ is selected from formulae SUB1-SUB6 as defined above, $R^x$ is selected from thiophene-2-yl, phenyl, thieno[3,2-b]thiophene-2-yl and dithiophene-2-yl, which are optionally substituted by alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated, $R^x$ is selected from formulae SUB7-SUB14 as defined above, $R^x$ is selected from phenyl that is substituted, preferably in 4-position, 3-position, 2,4-positions, 3,5-positions or 3,4,5-positions, with alkyl, alkoxy or thioalkyl, all of which are straight-chain having 1 to 24 C atoms or branched having 3 to 24 C atoms, and are optionally fluorinated, $R^x$ is selected from formulae SUB7-SUB11 as defined above, $R^x$ is selected from thiophene-2-yl that is substituted, preferably in 5-position, 4,5-positions or 3,4,5-positions, with alkyl, alkoxy or thioalkyl, all of which are straight-chain having 1 to 24 C atoms or branched having 3 to 24 C atoms, and are optionally fluorinated, $R^x$ is selected from formulae SUB12-SUB14 as defined above, $R^3$ and $R^4$ denote H, $R^1$ and $R^2$ have the same meaning, $R^1$ and $R^2$ are selected from aryl, heteroaryl, arylalkyl or heteroarylalkyl, each of which has 5 to 20 ring atoms, optionally contains fused rings and is unsubstituted or substituted by one or more groups L as defined in formula I, $R^1$ and $R^2$ are selected from alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated, $R^1$ and $R^2$ are selected from formulae SUB1-SUB6 as defined above, $R^1$ and $R^2$ are selected from thiophene-2-yl, phenyl, thieno[3,2-b]thiophene-2-yl and dithiophene-2-yl, which are optionally substituted by alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated, $R^1$ and $R^2$ are selected from formulae SUB7-SUB14 as defined above, $R^1$ and $R^2$ are selected from phenyl that is substituted, preferably in 4-position, 3-position, 2,4-positions, 3,5-positions or 3,4,5-positions, with alkyl, alkoxy or thioalkyl, all of which are straight-chain having 1 to 24 C atoms or branched having 3 to 24 C atoms, and are optionally fluorinated, $R^1$ and $R^2$ are selected from formulae SUB7-SUB11 as defined above, $R^1$ and $R^2$ are selected from thiophene-2-yl that is substituted, preferably in 5-position, 4,5-positions or 3,4,5-positions, with alkyl, alkoxy or thioalkyl, all of which are straight-chain having 1 to 24 C atoms or branched having 3 to 24 C atoms, and are optionally fluorinated, $R^1$ and $R^2$ are selected from formulae SUB12-SUB14 as defined above, $R^5$ is selected from alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated, $R^5$ denotes alkyl, alkoxy or thioalkyl, all of which are straight-chain having 1 to 24 C atoms or branched having 3 to 24 C atoms, and are optionally fluorinated, $R^5$ is selected from formulae SUB1-SUB6 as defined above, $R^6$ and $R^7$ are selected from formulae SUB1-SUB6 as defined above.

$R^8$ is selected from formulae SUB1-SUB6 as defined above, $R^9$ is H, $R^9$, when being different from H, is selected from formulae SUB1-SUB6 as defined above, one, two or three of the substituents $R^{o1}$ on the same benzene ring are different from H, $R^{10}$, when being different from H, is selected from formulae SUB1-SUB6 as defined above, $R^{11}$ is H, one of the substituents $R^{11}$ on the same thiophene ring is different from H, $R^{11}$, when being different from H, is selected from formulae SUB1-SUB6 as defined above, r is 1, preferably wherein the substituent $R^6$ is in para-position, r is 2 or 3, s is 0, s is 1, "alk1", and "alk2" when being different from H, are selected from 2-octyldodecyl, 2-hexyldecyl, 2-butyloctyl, 1,3-dimethyloctyl or 2-ethylhexyl, alk2 is H, "alk3" is selected from n-tetradecyl, n-dodecyl, 1,3-dimethyloctyl, 2-ethylhexyl or n-octyl, $R^{21}$ and $R^{22}$ have the same meaning, $R^{21}$ and $R^{22}$ are selected from Br, I, $B(OZ^2)_2$ and $Sn(Z^4)_3$, wherein $Z^2$ and $Z^4$ are as defined in formula M, $R^{23}$ and $R^{24}$ have the same meaning, $R^{23}$ and $R^{24}$ are selected from Br, I, $B(OZ^2)_2$ and $Sn(Z^4)_3$, wherein $Z^2$ and $Z^4$ are as defined in formula M.

The invention further relates to a method of preparing a conjugated polymer of formula I or its subformulae, by copolymerizing a monomer of formula M with a monomer of formula MB in an aryl-aryl coupling reaction

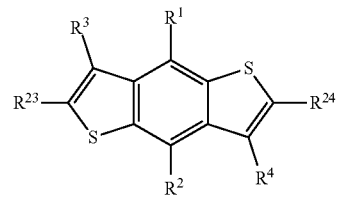

MB wherein $R^1$, $R^2$, $R^3$ and $R^4$ have the meanings given in formula I or one of the preferred meanings given above and below, and $R^{21}$ and $R^{22}$ have one of the meanings given for $R^{21}$ in formula M or one of its preferred meanings given above and below.

By appropriate choice of the reactive groups $R^{21-24}$ on the monomers of formula M and MB it can be ensured that a monomer of formula M does only react with a monomer of formula MB but not with another monomer of formula M, and a monomer of formula MB does only react with a monomer of formula M but not with another monomer of formula MB. For example, if $R^{21}$ and $R^{22}$ are selected from halide groups like Cl, Br or I, and $R^{23}$ and $R^{24}$ are selected from stannyl or boronate groups, or vice versa, the monomers of formula M and MB react with each other but not with a monomer of the same formula.

Thereby it is possible to synthesize polymers with an alternating sequence of benzodithiophene (BDT) repeat units and benzothiadiazole-dithienyl ($T^1$-BTZ-$T^2$) units.

Due to the asymmetric substitution pattern on the $T^1$-BTZ-$T^2$ units, wherein the BTZ group is monohalogenated and flanked by two thiophene rings $T^1$ and $T^2$, one of which is substituted and the other is unsubstituted, the polymer of the present invention will contain a random sequence of two different diads (BDT)-($T^1$-BTZ-$T^2$) and (BDT)-($T^2$-BTZ-$T^1$) as depicted in formula I and its subformulae, wherein a BDT group is linked to a $T^1$-BTZ-$T^2$ unit either via thiophene ring $T^1$ or via thiophene ring $T^2$.

The polymers of formula I and P can be suitably prepared for example by aryl-aryl coupling reactions, such as Yamamoto coupling, Suzuki coupling, Stille coupling, Negishi couling, C—H activation coupling. The educts can be prepared according to methods which are known to the person skilled in the art.

Preferred aryl-aryl coupling methods used in the synthesis methods as described above and below are Yamamoto coupling, Kumada coupling, Negishi coupling, Suzuki coupling, Stille coupling, Sonogashira coupling, Heck coupling, C—H activation coupling, Ullmann coupling or Buchwald coupling. Especially preferred are Suzuki coupling, Negishi coupling, Stille coupling and Yamamoto coupling. Suzuki coupling is described for example in WO 00/53656 A1. Negishi coupling is described for example in *J. Chem. Soc., Chem. Commun.*, 1977, 683-684. Yamamoto coupling is described in for example in T. Yamamoto et al., *Prog. Polym. Sci.*, 1993, 17, 1153-1205, or WO 2004/022626 A1. Stille coupling is described for example in Z. Bao et al., *J. Am. Chem. Soc.*, 1995, 117, 12426-12435 and C—H activation is described for example in M. Leclerc et al, *Angew. Chem. Int. Ed.*, 2012, 51, 2068-2071. For example, when using Yamamoto coupling, educts having two reactive halide groups are preferably used. When using Suzuki coupling, educts having two reactive boronic acid or boronic acid ester groups or two reactive halide groups are preferably used. When using Stille coupling, educts having two reactive stannane groups or two reactive halide groups are preferably used. When using Negishi coupling, educts having two reactive organozinc groups or two reactive halide groups are preferably used.

Preferred catalysts, especially for Suzuki, Negishi or Stille coupling, are selected from Pd(0) complexes or Pd(II) salts. Preferred Pd(0) complexes are those bearing at least one phosphine ligand such as Pd(Ph$_3$P)$_4$. Another preferred phosphine ligand is tris(ortho-tolyl)phosphine, i.e. Pd(o-Tol$_3$P)$_4$. Preferred Pd(II) salts include palladium acetate, i.e. Pd(OAc)$_2$. Alternatively the Pd(0) complex can be prepared by mixing a Pd(0) dibenzylideneacetone complex, for example tris(dibenzyl-ideneacetone)dipalladium(0), bis(dibenzylideneacetone)palladium(0), or Pd(II) salts e.g. palladium acetate, with a phosphine ligand, for example triphenylphosphine, tris(ortho-tolyl)phosphine or tri(tert-butyl)phosphine. Suzuki coupling is performed in the presence of a base, for example sodium carbonate, potassium carbonate, cesium carbonate, lithium hydroxide, potassium phosphate or an organic base such as tetraethylammonium carbonate or tetraethylammonium hydroxide. Yamamoto coupling employs a Ni(0) complex, for example bis(1,5-cyclooctadienyl) nickel(0).

As alternatives to halogens as described above, leaving groups of formula —O—SO$_2$Z$^0$ can be used wherein Z$^0$ is an alkyl or aryl group, preferably C$_{1-10}$ alkyl or C$_{6-12}$ aryl. Particular examples of such leaving groups are tosylate, mesylate and triflate.

The monomers of formula M and MB can be synthesized according to or in analogy to methods that are known to the skilled person and are described in the literature. Other methods of preparation can be taken from the examples.

Especially suitable and preferred synthesis methods of the monomers and polymers according to the present invention are illustrated in the synthesis schemes shown hereinafter.

The synthesis of the asymmetric T$^1$-BTZ-T$^2$ monomer is exemplarily illustrated in Scheme 1, wherein X and R$^5$ have the meanings given above.

The synthesis of the BDT monomer has been described in the literature for example in WO 2012/054910 A1, Y. Liang et al., *Journal of American Chemical Society* 2009, 131 (22), 7792-7799 and J. Hou et al., *Macromolecules* 2008, 41 (16), 6012-6018.

Scheme 1

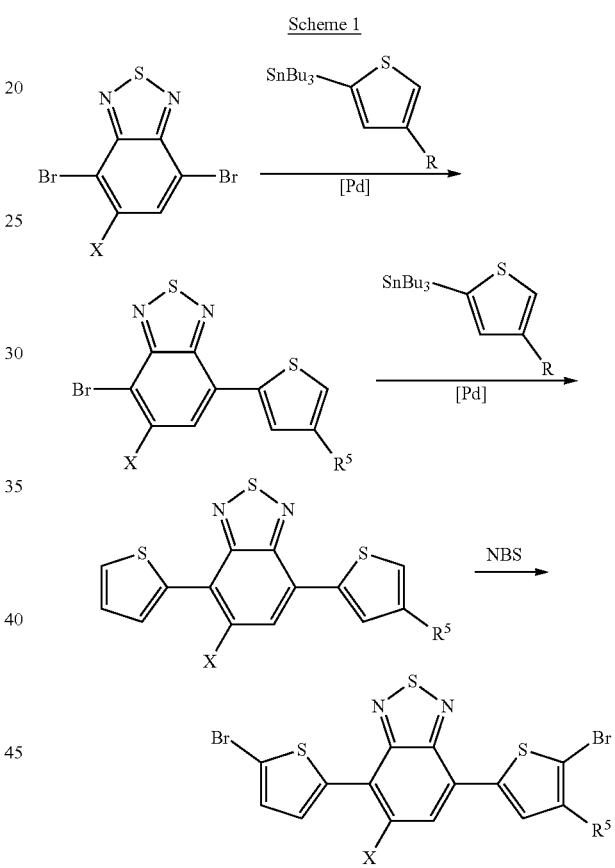

The synthesis of the polymer of formula I is exemplarily illustrated in Scheme 2, wherein X, R$^1$, R$^2$ and R$^5$ have the meanings given above and X$^1$ and X$^2$ are as defined in the Table below.

Scheme 2

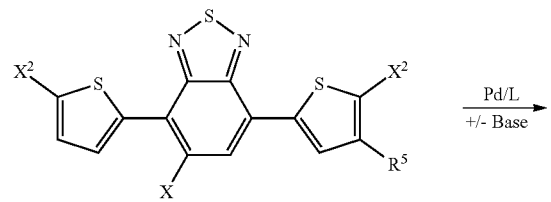

-continued

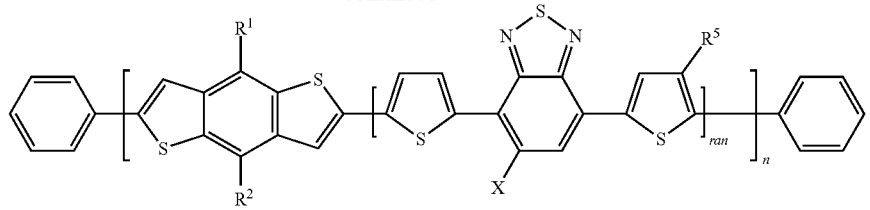

| $X^1$ | Br or I | Br or I | $SnR'_3$ | $B(OR')_2$ |
| $X^2$ | $SnR'_3$ | $B(OR')_2$ | Br or I | Br or I |

Further monomers and polymers can be synthesized in analogy to these methods.

Novel methods of preparing monomers and polymers as described above and below are another aspect of the invention.

The polymers of formula I can also be used in compositions, for example together with monomeric or polymeric compounds having charge-transport, semiconducting, electrically conducting, photo-conducting and/or light emitting semiconducting properties, or for example with compounds having hole blocking or electron blocking properties for use as interlayers or charge blocking layers in OLEDs or PSCs.

Thus, another aspect of the invention relates to a composition comprising one or more polymers of formula I and one or more small molecule compounds and/or polymers having one or more of a charge-transport, semiconducting, electrically conducting, photoconducting, hole blocking and electron blocking property.

These compositions blends can be prepared by conventional methods that are described in prior art and known to the skilled person. Typically the compounds and/or polymers are mixed with each other or dissolved in suitable solvents and the solutions combined.

Another aspect of the invention relates to a formulation comprising one or more polymers of formula I or a composition as described above and below and one or more organic solvents.

Preferred solvents are aliphatic hydrocarbons, chlorinated hydrocarbons, aromatic hydrocarbons, ketones, ethers and mixtures thereof. Additional solvents which can be used include 1,2,4-trimethylbenzene, 1,2,3,4-tetra-methyl benzene, pentylbenzene, mesitylene, cumene, cymene, cyclohexylbenzene, diethylbenzene, tetralin, decalin, 2,6-lutidine, 2-fluoro-m-xylene, 3-fluoro-o-xylene, 2-chlorobenzotrifluoride, N,N-dimethylformamide, 2-chloro-6-fluorotoluene, 2-fluoroanisole, anisole, 2,3-dimethylpyrazine, 4-fluoroanisole, 3-fluoroanisole, 3-trifluoro-methylanisole, 2-methylanisole, phenetol, 4-methylanisole, 3-methylanisole, 4-fluoro-3-methylanisole, 2-fluorobenzonitrile, 4-fluoroveratrol, 2,6-dimethylanisole, 3-fluorobenzo-nitrile, 2,5-dimethylanisole, 2,4-dimethylanisole, benzonitrile, 3,5-dimethyl-anisole, N,N-dimethylaniline, ethyl benzoate, 1-fluoro-3,5-dimethoxy-benzene, 1-methylnaphthalene, N-methylpyrrolidinone, 3-fluorobenzo-trifluoride, benzotrifluoride, dioxane, trifluoromethoxy-benzene, 4-fluorobenzotrifluoride, 3-fluoropyridine, toluene, 2-fluoro-toluene, 2-fluorobenzotrifluoride, 3-fluorotoluene, 4-isopropylbiphenyl, phenyl ether, pyridine, 4-fluorotoluene, 2,5-difluorotoluene, 1-chloro-2,4-difluorobenzene, 2-fluoropyridine, 3-chlorofluoro-benzene, 1-chloro-2,5-difluorobenzene, 4-chlorofluorobenzene, chloro-benzene, o-dichlorobenzene, 2-chlorofluorobenzene, p-xylene, m-xylene, o-xylene or mixture of o-, m-, and p-isomers. Solvents with relatively low polarity are generally preferred. For inkjet printing solvents and solvent mixtures with high boiling temperatures are preferred. For spin coating alkylated benzenes like xylene and toluene are preferred.

Examples of especially preferred solvents include, without limitation, dichloromethane, trichloromethane, chlorobenzene, o-dichlorobenzene, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and/or mixtures thereof.

The total concentration of solid compounds and polymers in the solution is preferably 0.1 to 10% by weight, more preferably 0.5 to 5% by weight. Optionally, the solution also comprises one or more binders to adjust the rheological properties, as described for example in WO 2005/055248 A1.

After the appropriate mixing and ageing, solutions are evaluated as one of the following categories: complete solution, borderline solution or insoluble. The contour line is drawn to outline the solubility parameter-hydrogen bonding limits dividing solubility and insolubility. 'Complete' solvents falling within the solubility area can be chosen from literature values such as published in "Crowley, J. D., Teague, G. S. Jr and Lowe, J. W. Jr., *Journal of Paint Technology*, 1966, 38 (496), 296". Solvent blends may also be used and can be identified as described in "Solvents, W. H. Ellis, Federation of Societies for Coatings Technology, p9-10, 1986".

Such a procedure may lead to a blend of 'non' solvents that will both dissolve the compounds of the present invention, although it is desirable to have at least one true solvent in a blend.

The polymers of formula I can also be used in patterned OSC layers in the devices as described above and below. For applications in modern microelectronics it is generally desirable to generate small structures or patterns to reduce cost (more devices/unit area), and power consumption.

Patterning of thin layers comprising a compound according to the present invention can be carried out for example by photolithography, electron beam lithography or laser patterning.

For use as thin layers in electronic or electrooptical devices the compounds, compositions or formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

Ink jet printing is particularly preferred when high resolution layers and devices needs to be prepared. Selected formulations of the present invention may be applied to prefabricated device substrates by ink jet printing or microdispensing. Preferably industrial piezoelectric print heads such as but not limited to those supplied by Aprion, Hitachi-Koki, InkJet Technology, On Target Technology, Picojet, Spectra, Trident, Xaar may be used to apply the organic semiconductor layer to a substrate. Additionally semi-industrial heads such as those manufactured by Brother, Epson, Konica, Seiko Instruments Toshiba TEC or single nozzle microdispensers such as those produced by Microdrop and Microfab may be used.

In order to be applied by ink jet printing or microdispensing, the compounds or polymers should be first dissolved in a suitable solvent. Solvents must fulfil the requirements stated above and must not have any detrimental effect on the chosen print head. Additionally, solvents should have boiling points >100° C., preferably >140° C. and more preferably >150° C. in order to prevent operability problems caused by the solution drying out inside the print head. Apart from the solvents mentioned above, suitable solvents include substituted and non-substituted xylene derivatives, di-$C_{1-2}$-alkyl formamide, substituted and non-substituted anisoles and other phenol-ether derivatives, substituted heterocycles such as substituted pyridines, pyrazines, pyrimidines, pyrrolidinones, substituted and non-substituted N,N-di-$C_{1-2}$-alkylanilines and other fluorinated or chlorinated aromatics.

A preferred solvent for depositing a polymer of formula I by ink jet printing comprises a benzene derivative which has a benzene ring substituted by one or more substituents wherein the total number of carbon atoms among the one or more substituents is at least three. For example, the benzene derivative may be substituted with a propyl group or three methyl groups, in either case there being at least three carbon atoms in total. Such a solvent enables an ink jet fluid to be formed comprising the solvent with the compound or polymer, which reduces or prevents clogging of the jets and separation of the components during spraying. The solvent (s) may include those selected from the following list of examples: dodecylbenzene, 1-methyl-4-tert-butylbenzene, terpineol, limonene, isodurene, terpinolene, cymene, diethylbenzene. The solvent may be a solvent mixture, that is a combination of two or more solvents, each solvent preferably having a boiling point >100° C., more preferably >140° C. Such solvent(s) also enhance film formation in the layer deposited and reduce defects in the layer.

The ink jet fluid (that is mixture of solvent, binder and semiconducting compound) preferably has a viscosity at 20° C. of 1-100 mPa·s, more preferably 1-50 mPa·s and most preferably 1-30 mPa·s.

The compositions and formulations according to the present invention can additionally comprise one or more further components or additives selected for example from surface-active compounds, lubricating agents, wetting agents, dispersing agents, hydrophobing agents, adhesive agents, flow improvers, defoaming agents, deaerators, diluents which may be reactive or non-reactive, auxiliaries, colourants, dyes or pigments, sensitizers, stabilizers, nanoparticles or inhibitors.

The compounds according to the present invention are useful as charge transport, semiconducting, electrically conducting, photoconducting or light emitting materials in optical, electrooptical, electronic, electroluminescent or photoluminescent components or devices. In these devices, the compounds of the present invention are typically applied as thin layers or films.

Thus, the present invention also provides the use of the semiconducting compound or composition or layer in an electronic device. The compound or composition may be used as a high mobility semiconducting material in various devices and apparatus. The compound or composition may be used, for example, in the form of a semiconducting layer or film. Accordingly, in another aspect, the present invention provides a semiconducting layer for use in an electronic device, the layer comprising a compound or composition according to the invention. The layer or film may be less than about 30 microns. For various electronic device applications, the thickness may be less than about 1 micron thick. The layer may be deposited, for example on a part of an electronic device, by any of the aforementioned solution coating or printing techniques.

The invention additionally provides an electronic device comprising compound or composition or organic semiconducting layer according to the present invention. Especially preferred devices are OFETs, TFTs, ICs, logic circuits, capacitors, RFID tags, OLEDs, OLETs, OPEDs, OPVs, PSCs, OPDs, solar cells, laser diodes, photoconductors, photodetectors, electrophotographic devices, electrophotographic recording devices, organic memory devices, sensor devices, charge injection layers, Schottky diodes, planarising layers, antistatic films, conducting substrates and conducting patterns.

Especially preferred electronic device are OFETs, OLEDs, OPV, PSC and OPD devices, in particular OPD, PSC and bulk heterojunction (BHJ) OPV devices. In an OFET, for example, the active semiconductor channel between the drain and source may comprise the compound or composition of the invention. As another example, in an OLED device, the charge (hole or electron) injection or transport layer may comprise the compound or composition of the invention.

For use in the photoactive layer of OPV or OPD devices the compounds according to the present invention are preferably used in a composition that comprises or contains, more preferably consists of, one or more p-type (electron donor) semiconductors and one or more n-type (electron acceptor) semiconductors.

The p-type semiconductor is a polymer of formula I.

The n-type semiconductor is preferably a small molecule.

The composition can also comprise a polymer of formula I as p-type semiconductor, and an n-type semiconductor which is a fullerene or substituted fullerene.

The fullerene is for example an indene-$C_{60}$-fullerene bisadduct like ICBA, or a (6,6)-phenyl-butyric acid methyl ester derivatized methano $C_{60}$ fullerene, also known as "PCBM-$C_{60}$" or "$C_{60}$PCBM", as disclosed for example in G. Yu, J. Gao, J. C. Hummelen, F. Wudl, A. J. Heeger, Science 1995, Vol. 270, p. 1789 ff and having the structure shown below, or structural analogous compounds with e.g. a $C_{61}$ fullerene group, a $C_{70}$ fullerene group, or a $C_{71}$ fullerene group, or an organic polymer (see for example Coakley, K. M. and McGehee, M. D. *Chem. Mater.* 2004, 16, 4533).

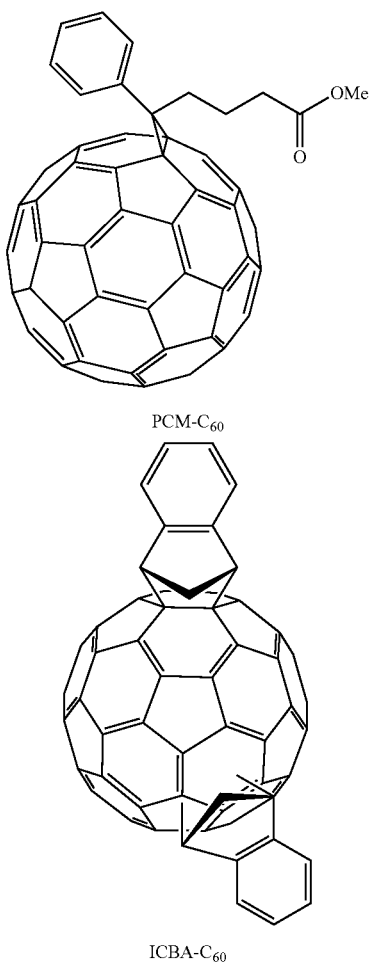

PCM-C$_{60}$

ICBA-C$_{60}$

Preferably the compound according to the present invention is blended with an additional n-type semiconductor such as a fullerene or substituted fullerene of formula Full-I to form the active layer in an OPV or OPD device

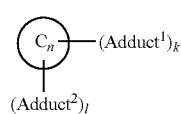  Full-I wherein

C$_n$ denotes a fullerene composed of n carbon atoms, optionally with one or more atoms trapped inside, Adduct$^1$ is a primary adduct appended to the fullerene C$_n$ with any connectivity, Adduct$^2$ is a secondary adduct, or a combination of secondary adducts, appended to the fullerene C$_n$ with any connectivity, k is an integer ≥1, and l is 0, an integer ≥1, or a non-integer >0.

In the formula Full-I and its subformulae, k preferably denotes 1, 2, 3 or, 4, very preferably 1 or 2.

The fullerene C$_n$ in formula Full-I and its subformulae may be composed of any number n of carbon atoms Preferably, in the compounds of formula Full-I and its subformulae the number of carbon atoms n of which the fullerene C$_n$ is composed is 60, 70, 76, 78, 82, 84, 90, 94 or 96, very preferably 60 or 70.

The fullerene C$_n$ in formula Full-I and its subformulae is preferably selected from carbon based fullerenes, endohedral fullerenes, or mixtures thereof, very preferably from carbon based fullerenes.

Suitable and preferred carbon based fullerenes include, without limitation, (C$_{60-Ih}$)[5,6]fullerene, (C$_{70-D5h}$)[5,6]fullerene, (C$_{76-D2*}$)[5,6]fullerene, (C$_{84-D2*}$)[5,6]fullerene, (C$_{84-D2d}$)[5,6]fullerene, or a mixture of two or more of the aforementioned carbon based fullerenes.

The endohedral fullerenes are preferably metallofullerenes. Suitable and preferred metallofullerenes include, without limitation, La@C$_{60}$, La@C$_{82}$, Y@C$_{82}$, Sc$_3$N@C$_{80}$, Y$_3$N@C$_{80}$, Sc$_3$C$_2$@C$_{80}$ or a mixture of two or more of the aforementioned metallofullerenes.

Preferably the fullerene C$_n$ is substituted at a [6,6] and/or [5,6] bond, preferably substituted on at least one [6,6] bond.

Primary and secondary adduct, named "Adduct" in formula Full-I and its subformulae, is preferably selected from the following formulae

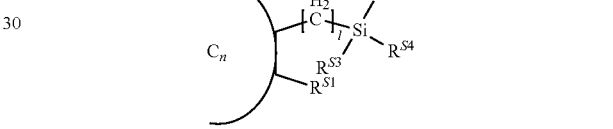  S-1

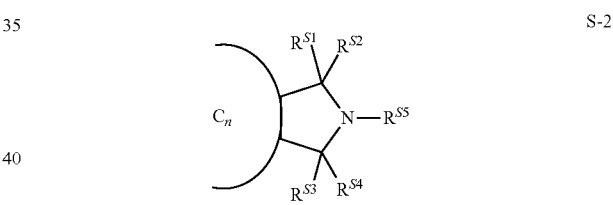  S-2

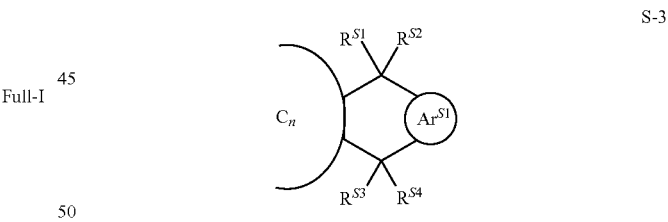  S-3

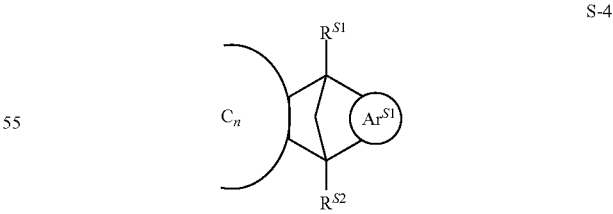  S-4

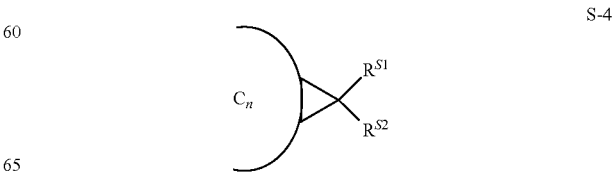  S-4

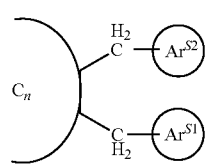
S-5

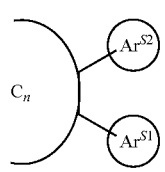
S-6

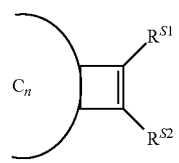
S-7

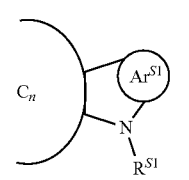
S-8

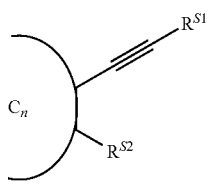
S-9

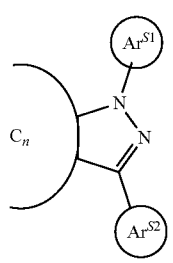
S-10

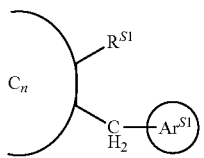
S-11

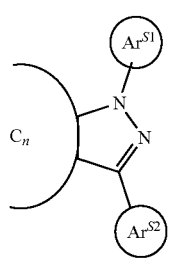
S-12

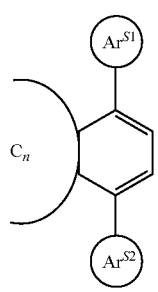
S-13

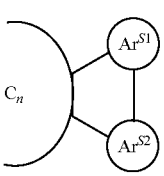
S-14 wherein $Ar^{S1}$, $Ar^{S2}$ denote, independently of each other, an aryl or heteroaryl group with 5 to 20, preferably 5 to 15, ring atoms, which is mono- or polycyclic, and which is optionally substituted by one or more identical or different substituents having one of the meanings of L as defined above and below, $R^{S1}$, $R^{S2}$, $R^{S3}$, $R^{S4}$ and $R^{S5}$ independently of each other denote H, CN or have one of the meanings of L as defined above and below.

Preferred compounds of formula Full-I are selected from the following subformulae:

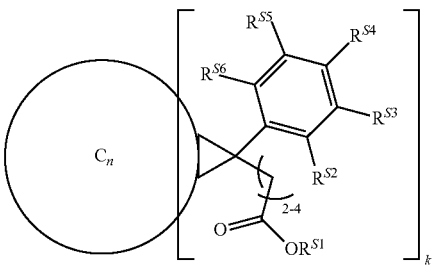
Full-Ia

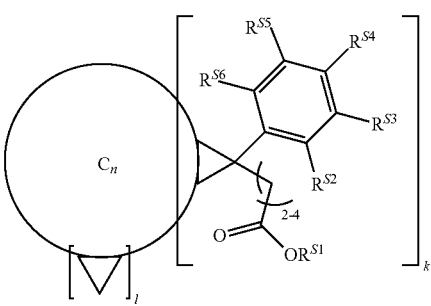
Full-Ib

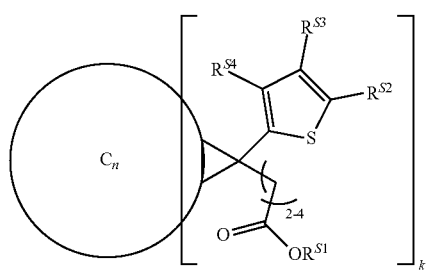

Full-Ic

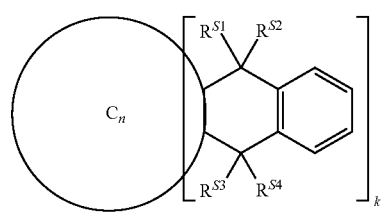

Full-Id

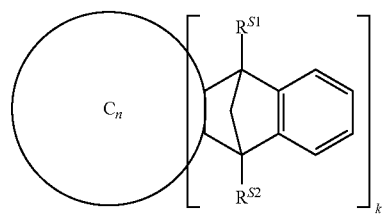

Full-Ie

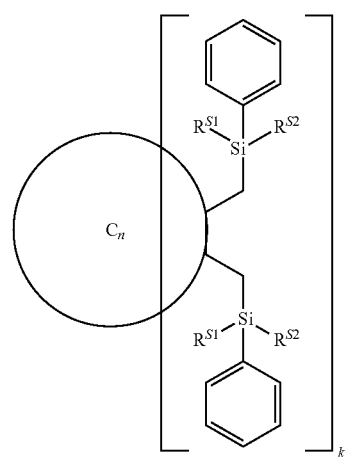

Full-If

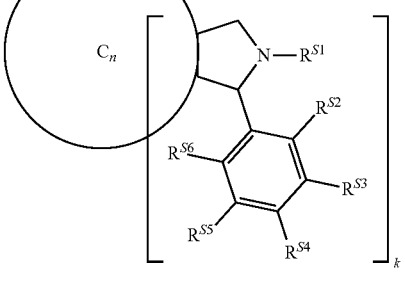

Full-Ig

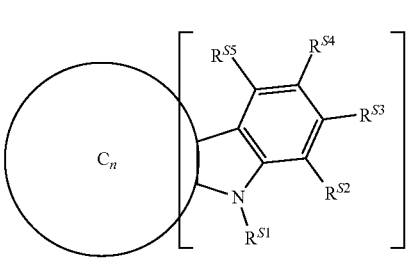

Full-Ih $R^{S1}$, $R^{S2}$, $R^{S3}$, $R^{S4}$ $R^{S5}$ and $R^{S6}$ independently of each other denote H or have one of the meanings of $R^S$ as defined above and below.

Most preferably the fullerene is PCBM-C60, PCBM-C70, bis-PCBM-C60, bis-PCBM-C70, ICMA-c60 (1',4'-dihydro-naphtho[2',3':1,2][5,6]fullerene-C60), ICBA, oQDM-C60 (1',4'-dihydro-naphtho[2',3':1,9][5,6]fullerene-C60-lh), or bis-oQDM-C60.

In another preferred embodiment, the composition according to the present invention contains a polymer of formula I as p-type semiconductor and an n-type semiconductor which is selected from small molecules that are not fullerenes or fullerene derivatives, hereinafter also referred to as "non-fullerene acceptor" or NFA.

Preferred NFAs are selected from compounds containing a polycyclic electron donating core and attached thereto two terminal electron withdrawing groups, preferably selected of formula N below

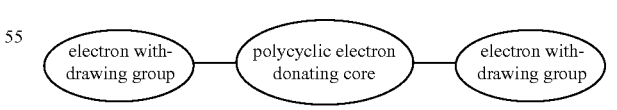

N

Examples for suitable and preferred NFAs are the compound ITIC shown below, as disclosed by Y. Lin, J. Wang, Z.-G. Zhang, H. Bai, Y. Li, D. *Zhu and X. Zhan, Adv. Mater.* 2015, 27, 1170-1174, and the compound IEIC shown below, as disclosed by H. Lin, S. Chen, Z. Li, J. Y. L. Lai, G. Yang, T. McAfee, K. Jiang, Y. Li, Y. Liu, H. Hu, J. Zhao, W. Ma, H. Ade and H. Yan, Zhan, *Adv. Mater.,* 2015, 27, 7299.

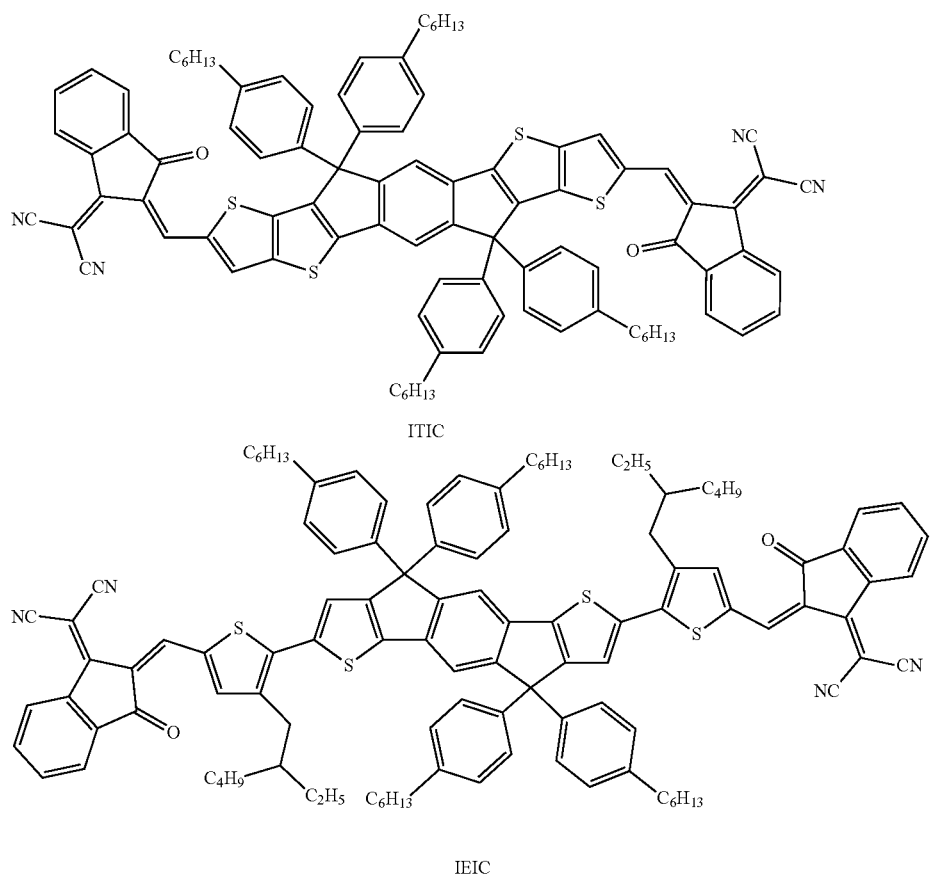

ITIC

IEIC

Further preferred NFAs are those disclosed in WO 2018/007479 A1, WO 2018/036914 A1, WO 2018/065350 A1, WO 2018/065352 A1, WO 2018/065356 A1 and EP 3306690 A1.

Further preferred NFAs are selected from naphthalene or perylene derivatives. Suitable and preferred naphthalene or perylene derivatives for use as n-type compounds are described for example in *Adv. Sci.* 2016, 3, 1600117, *Adv. Mater.* 2016, 28, 8546-8551, *J. Am. Chem. Soc.*, 2016, 138, 7248-7251 and *J. Mater. Chem. A*, 2016, 4, 17604.

The OPV or OPD device preferably further comprises a first transparent or semi-transparent electrode on a transparent or semi-transparent substrate on one side of the photoactive layer, and a second metallic or semi-transparent electrode on the other side of the photoactive layer.

Further preferably the OPV or OPD device comprises, between the photoactive layer and the first or second electrode, one or more additional buffer layers acting as hole transporting layer and/or electron blocking layer, which comprise a material such as metal oxide, like for example, ZTO, MoOx, NiOx, a conjugated polymer electrolyte, like for example PEDOT:PSS, a conjugated polymer, like for example polytriarylamine (PTAA), an insulating polymer, like for example nafion, polyethyleneimine or polystyrenesulphonate, an organic compound, like for example N,N'-diphenyl-N,N'-bis(1-naphthyl)(1,1'-biphenyl)-4,4'diamine (NPB), N,N'-diphenyl-N,N'-(3-methylphenyl)-1,1'-biphenyl-4,4'-diamine (TPD), or alternatively as hole blocking layer and/or electron transporting layer, which comprise a material such as metal oxide, like for example, $ZnO_x$, $TiO_x$, a salt, like for example LiF, NaF, CsF, a conjugated polymer electrolyte, like for example poly[3-(6-trimethylammoniumhexyl)thiophene], poly(9,9-bis(2-ethylhexyl)-fluorene]-b-poly[3-(6-trimethylammoniumhexyl)thiophene], or poly [(9,9-bis(3'-(N,N-dimethylamino)propyl)-2,7-fluorene)-alt-2,7-(9,9-dioctylfluorene)] or an organic compound, like for example tris(8-quinolinolato)-aluminium(III) ($Alq_3$), 4,7-diphenyl-1,10-phenanthroline.

In a composition according to the present invention comprising a polymer of formula I as p-type semiconductor and an n-type semiconductor, which is for example a small molecule, the ratio p-type:n-type is preferably from 5:1 to 1:5, more preferably from 1:1 to 1:3, most preferably 1:1 to 1:2 by weight.

The composition according to the present invention may also comprise a polymeric binder, preferably from 0.001 to 95% by weight. Examples of binder include polystyrene (PS), polydimethylsilane (PDMS), polypropylene (PP) and polymethylmethacrylate (PMMA).

A binder to be used in the formulation as described before, which is preferably a polymer, may comprise either an insulating binder or a semiconducting binder, or mixtures thereof, may be referred to herein as the organic binder, the polymeric binder or simply the binder.

Preferably, the polymeric binder comprises a weight average molecular weight in the range of 1000 to 5,000,000 g/mol, especially 1500 to 1,000,000 g/mol and more preferable 2000 to 500,000 g/mol. Surprising effects can be achieved with polymers having a weight average molecular weight of at least 10000 g/mol, more preferably at least 100000 g/mol.

In particular, the polymer can have a polydispersity index $M_w/M_n$ in the range of 1.0 to 10.0, more preferably in the range of 1.1 to 5.0 and most preferably in the range of 1.2 to 3.

Preferably, the inert binder is a polymer having a glass transition temperature in the range of −70 to 160° C., preferably 0 to 150° C., more preferably 50 to 140° C. and most preferably 70 to 130° C. The glass transition temperature can be determined by measuring the DSC of the polymer (DIN EN ISO 11357, heating rate 10° C. per minute).

The weight ratio of the polymeric binder to the OSC compound, like that of formula I, is preferably in the range of 30:1 to 1:30, particularly in the range of 5:1 to 1:20 and more preferably in the range of 1:2 to 1:10.

According to a preferred embodiment the binder preferably comprises repeating units derived from styrene monomers and/or olefin monomers. Preferred polymeric binders can comprise at least 80%, preferably 90% and more preferably 99% by weight of repeating units derived from styrene monomers and/or olefins.

Styrene monomers are well known in the art. These monomers include styrene, substituted styrenes with an alkyl substituent in the side chain, such as α-methylstyrene and α-ethylstyrene, substituted styrenes with an alkyl substituent on the ring such as vinyltoluene and p-methylstyrene, halogenated styrenes such as monochlorostyrenes, dichlorostyrenes, tribromostyrenes and tetrabromostyrenes.

Olefin monomers consist of hydrogen and carbon atoms. These monomers include ethylene, propylene, butylenes, isoprene and 1,3-butadiene.

According to a preferred embodiment of the present invention, the polymeric binder is polystyrene having a weight average molecular weight in the range of 50,000 to 2,000,000 g/mol, preferably 100,000 to 750,000 g/mol, more preferably in the range of 150,000 to 600,000 g/mol and most preferably in the range of 200,000 to 500,000 g/mol.

Further examples of suitable binders are disclosed for example in US 2007/0102696 A1. Especially suitable and preferred binders are described in the following.

The binder should preferably be capable of forming a film, more preferably a flexible film.

Suitable polymers as binders include poly(1,3-butadiene), polyphenylene, polystyrene, poly(α-methylstyrene), poly(α-vinylnaphtalene), poly(vinyltoluene), polyethylene, cis-polybutadiene, polypropylene, polyisoprene, poly(4-methyl-1-pentene), poly (4-methylstyrene), poly(chorotrifluoroethylene), poly(2-methyl-1,3-butadiene), poly(p-xylylene), poly(α-α-α'-α' tetrafluoro-p-xylylene), poly[1,1-(2-methyl propane)bis(4-phenyl)carbonate], poly(cyclohexyl methacrylate), poly(chlorostyrene), poly(2,6-dimethyl-1,4-phenylene ether), polyisobutylene, poly(vinyl cyclohexane), poly(vinylcinnamate), poly(4-vinylbiphenyl), 1,4-polyisoprene, polynorbornene, poly(styrene-block-butadiene); 31% wt styrene, poly(styrene-block-butadiene-block-styrene); 30% wt styrene, poly(styrene-co-maleic anhydride) (and ethylene/butylene) 1-1.7% maleic anhydride, poly(styrene-block-ethylene/butylene-block-styrene) triblock polymer 13% styrene, poly(styrene-block-ethylene-propylene-block-styrene) triblock polymer 37% wt styrene, poly(styrene-block-ethylene/butylene-block-styrene) triblock polymer 29% wt styrene, poly(1-vinylnaphthalene), poly(1-vinyl pyrrolidone-co-styrene) 64% styrene, poly(1-vinylpyrrolidone-co-vinyl acetate) 1.3:1, poly(2-chlorostyrene), poly(2-vinylnaphthalene), poly(2-vinylpyridine-co-styrene) 1:1, poly(4,5-Difluoro-2,2-bis($CF_3$)-1,3-dioxole-co-tetrafluoroethylene) Teflon, poly(4-chlorostyrene), poly(4-methyl-1-pentene), poly(4-methylstyrene), poly(4-vinylpyridine-co-styrene) 1:1, poly(alpha-methylstyrene), poly(butadiene-graft-poly(methyl acrylate-co-acrylonitrile)) 1:1:1, poly(butyl methacrylate-co-isobutyl methacrylate) 1:1, poly(butyl methacrylate-co-methyl methacrylate) 1:1, poly(cyclohexylmethacrylate), poly(ethylene-co-1-butene-co-1-hexene) 1:1:1, poly(ethylene-co-ethylacrylate-co-maleic anhydride); 2% anhydride, 32% ethyl acrylate, poly(ethylene-co-glycidyl methacrylate) 8% glycidyl methacrylate, poly(ethylene-co-methyl acrylate-co-glycidyl meth-acrylate) 8% glycidyl metha-crylate 25% methyl acrylate, poly(ethylene-co-octene) 1:1, poly(ethylene-co-propylene-co-5-methylene-2-norbornene) 50% ethylene, poly(ethylene-co-tetrafluoroethylene) 1:1, poly(isobutyl methacrylate), poly(isobutylene), poly(methyl methacrylate)-co-(fluorescein O-methacrylate) 80% methyl methacrylate, poly(methyl methacrylate-co-butyl methacrylate) 85% methyl methacrylate, poly(methyl methacrylate-co-ethyl acrylate) 5% ethyl acrylate, poly(propylene-co-butene) 12% 1-butene, poly(styrene-co-allyl alcohol) 40% allyl alcohol, poly(styrene-co-maleic anhydride) 7% maleic anhydride, poly(styrene-co-maleic anhydride) cumene terminated (1.3:1), poly(styrene-co-methyl methacrylate) 40% styrene, poly(vinyltoluene-co-alpha-methylstyrene) 1:1, poly-2-vinylpyridine, poly-4-vinylpyridine, poly-alpha-pinene, polymethylmethacrylate, polybenzylmethacrylate, polyethylmethacrylate, polyethylene, polyethylene terephthalate, polyethylene-co-ethylacrylate 18% ethyl acrylate, polyethylene-co-vinylacetate 12% vinyl acetate, polyethylene-graft-maleic anhydride 0.5% maleic anhydride, polypropylene, polypropylene-graft-maleic anhydride 8-10% maleic anhydride, polystyrene poly(styrene-block-ethylene/butylene-block-styrene) graft maleic anhydride 2% maleic anhydride 1:1:1 others, poly(styrene-block-butadiene) branched 1:1, poly(styrene-block-butadiene-block-styrene), 30% styrene, poly(styrene-block-isoprene) 10% wt styrene, poly(styrene-block-isoprene-block-styrene) 17% wt styrene, poly(styrene-co-4-chloromethylstyrene-co-4-methoxymethylstyrene 2:1:1, polystyrene-co-acrylonitrile 25% acrylonitrile, polystyrene-co-alpha-methylstyrene 1:1, polystyrene-co-butadiene 4% butadiene, polystyrene-co-butadiene 45% styrene, polystyrene-co-chloromethylstyrene 1:1, polyvinylchloride, polyvinylcinnamate, polyvinylcyclohexane, polyvinylidenefluoride, polyvinylidenefluoride-co-hexafluoropropylene assume 1:1, poly(styrene-block-ethylene/propylene-block-styrene) 30% styrene, poly(styrene-block-ethylene/propylene-block-styrene) 18% styrene, poly(styrene-block-ethylene/propylene-block-styrene) 13% styrene, poly(styrene-block ethylene block-ethylene/propylene-block styrene) 32% styrene, poly(styrene-block ethylene block-ethylene/propylene-block styrene) 30% styrene, poly(styrene-block-ethylene/butylene-block-styrene) 31% styrene, poly(styrene-block-ethylene/butylene-block-styrene) 34% styrene, poly(styrene-block-ethylene/butylene-block-styrene) 30% styrene, poly(styrene-block-ethylene/butylene-block-styrene) 60%, styrene, branched or nonbranched polystyrene-block-polybutadiene, polystyrene-block(polyethylene-ran-butylene)-block-polystyrene, polystyrene-block-polybutadiene-block-polystyrene, polystyrene-(ethylene-propylene)-diblock-copolymers (e.g. KRATON®-G1701E, Shell), poly(propylene-co-ethylene) and poly(styrene-co-methylmethacrylate).

Preferred insulating binders to be used in the formulations as described before are polystryrene, poly(α-methylstyrene), polyvinylcinnamate, poly(4-vinylbiphenyl), poly(4- methylstyrene), and polymethyl methacrylate. Most preferred insulating binders are polystyrene and polymethyl methacrylate.

The binder can also be selected from crosslinkable binders, like e.g. acrylates, epoxies, vinylethers, thiolenes etc. The binder can also be mesogenic or liquid crystalline.

The organic binder may itself be a semiconductor, in which case it will be referred to herein as a semiconducting binder. The semiconducting binder is still preferably a binder of low permittivity as herein defined. Semiconducting binders for use in the present invention preferably have a number average molecular weight ($M_n$) of at least 1500-2000, more preferably at least 3000, even more preferably at least 4000 and most preferably at least 5000. The semiconducting binder preferably has a charge carrier mobility of at least $10^{-5}$ cm$^2$V$^{-1}$s$^{-1}$, more preferably at least $10^{-4}$ cm$^2$V$^{-1}$s$^{-1}$.

A preferred semiconducting binder comprises a homopolymer or copolymer (including block-copolymer) containing arylamine (preferably triarylamine).

To produce thin layers in BHJ OPV devices the compounds, compositions and formulations of the present invention may be deposited by any suitable method. Liquid coating of devices is more desirable than vacuum deposition techniques. Solution deposition methods are especially preferred. The formulations of the present invention enable the use of a number of liquid coating techniques. Preferred deposition techniques include, without limitation, dip coating, spin coating, ink jet printing, nozzle printing, letterpress printing, screen printing, gravure printing, doctor blade coating, roller printing, reverse-roller printing, offset lithography printing, dry offset lithography printing, flexographic printing, web printing, spray coating, curtain coating, brush coating, slot dye coating or pad printing.

For the fabrication of OPV devices and modules area printing method compatible with flexible substrates are preferred, for example slot dye coating, spray coating and the like.

Suitable solutions or formulations containing the mixture of a polymer of formula I and an n-type semiconductor must be prepared. In the preparation of formulations, suitable solvent must be selected to ensure full dissolution of both component, p-type and n-type and take into account the boundary conditions (for example rheological properties) introduced by the chosen printing method.

Organic solvent are generally used for this purpose. Typical solvents can be aromatic solvents, halogenated solvents or chlorinated solvents, including chlorinated aromatic solvents. Examples include, but are not limited to chlorobenzene, 1,2-dichlorobenzene, chloroform, 1,2-dichloroethane, dichloromethane, carbon tetrachloride, toluene, cyclohexanone, ethylacetate, tetrahydrofuran, anisole, 2,4-dimethylanisole, 1-methylnaphthalene, morpholine, toluene, o-xylene, m-xylene, p-xylene, 1,4-dioxane, acetone, methylethylketone, 1,2-dichloroethane, 1,1,1-trichloroethane, 1,1,2,2-tetrachloroethane, ethyl acetate, n-butyl acetate, N,N-dimethylformamide, dimethylacetamide, dimethylsulfoxide, 1,5-dimethyltetraline, propiophenone, acetophenone, tetraline, 2-methylthiophene, 3-methylthiophene, decaline, indane, methyl benzoate, ethyl benzoate, mesitylene and combinations thereof.

The OPV device can for example be of any type known from the literature (see e.g. Waldauf et al., *Appl. Phys. Lett.,* 2006, 89, 233517).

A first preferred OPV device according to the invention comprises the following layers (in the sequence from bottom to top):

optionally a substrate,
a high work function electrode, preferably comprising a metal oxide, like for example ITO, serving as anode,
an optional conducting polymer layer or hole transport layer, preferably comprising an organic polymer or polymer blend, for example of PEDOT:PSS (poly(3,4-ethylenedioxythiophene): poly(styrene-sulfonate), or TBD (N,N'-dyphenyl-N—N'-bis(3-methylphenyl)-1,1'biphenyl-4,4'-diamine) or NBD (N,N'-dyphenyl-N—N'-bis(1-napthylphenyl)-1,1'biphenyl-4,4'-diamine),
a layer, also referred to as "photoactive layer", comprising a p-type and an n-type organic semiconductor, which can exist for example as a p-type/n-type bilayer or as distinct p-type and n-type layers, or as blend or p-type and n-type semiconductor, forming a BHJ,
optionally a layer having electron transport properties, for example comprising LiF or PFN,
a low work function electrode, preferably comprising a metal like for example aluminium, serving as cathode,
wherein at least one of the electrodes, preferably the anode, is transparent to visible light, and
wherein the p-type semiconductor is a polymer of formula I.

A second preferred OPV device according to the invention is an inverted OPV device and comprises the following layers (in the sequence from bottom to top):

optionally a substrate,
a high work function metal or metal oxide electrode, comprising for example ITO, serving as cathode,
a layer having hole blocking properties, preferably comprising a metal oxide like $TiO_x$ or $Zn_x$, or a poly(ethyleneimine),
a photoactive layer comprising a p-type and an n-type organic semiconductor, situated between the electrodes, which can exist for example as a p-type/n-type bilayer or as distinct p-type and n-type layers, or as blend or p-type and n-type semiconductor, forming a BHJ,
an optional conducting polymer layer or hole transport layer, preferably comprising an organic polymer or polymer blend, for example of PEDOT:PSS, nafion or a substituted triaryl amine derivative like for example TBD or NBD,
an electrode comprising a high work function metal like for example silver, serving as anode,
wherein at least one of the electrodes, preferably the cathode, is transparent to visible light, and
wherein the n-type semiconductor is a polymer of formula I.

In the OPV devices of the present invention the p-type and n-type semiconductor materials are preferably selected from the materials, like the compound/polymer/fullerene systems, as described above When the photoactive layer is deposited on the substrate, it forms a BHJ that phase separates at nanoscale level. For discussion on nanoscale phase separation see Dennler et al, *Proceedings of the IEEE,* 2005, 93 (8), 1429 or Hoppe et al, *Adv. Func. Mater,* 2004, 14(10), 1005. An optional annealing step may be then necessary to optimize blend morphology and consequently OPV device performance.

Another method to optimize device performance is to prepare formulations for the fabrication of OPV(BHJ) devices that may include high boiling point additives to promote phase separation in the right way. 1,8-Octanedithiol, 1,8-diiodooctane, nitrobenzene, chloronaphthalene, and other additives have been used to obtain high-efficiency solar cells. Examples are disclosed in J. Peet, et al, *Nat. Mater.*, 2007, 6, 497 or Frechet et al. *J. Am. Chem. Soc.*, 2010, 132, 7595-7597.

Another preferred embodiment of the present invention relates to the use of a compound or composition according to the present invention as dye, hole transport layer, hole blocking layer, electron transport layer and/or electron blocking layer in a DSSC or PSC, and to a DSSC or PSC comprising a compound composition or polymer blend according to the present invention.

DSSCs and PSCs can be manufactured as described in the literature, for example in Chem. Rev. 2010, 110, 6595-6663, Angew. Chem. Int. Ed. 2014, 53, 2-15 or in WO2013171520A1.

A preferred OE device according to the invention is a solar cell, preferably a PSC, comprising a light absorber which is at least in part inorganic as described below.

In a solar cell comprising the light absorber according to the invention there are no restrictions per se with respect to the choice of the light absorber material which is at least in part inorganic.

The term "at least in part inorganic" means that the light absorber material may be selected from metalorganic complexes or materials which are substantially inorganic and possess preferably a crystalline structure where single positions in the crystalline structure may be allocated by organic ions.

Preferably, the light absorber comprised in the solar cell according to the invention has an optical band-gap ≤2.8 eV and ≥0.8 eV.

Very preferably, the light absorber in the solar cell according to the invention has an optical band-gap ≤2.2 eV and ≥1.0 eV.

The light absorber used in the solar cell according to the invention does preferably not contain a fullerene. The chemistry of fullerenes belongs to the field of organic chemistry. Therefore fullerenes do not fulfil the definition of being "at least in part inorganic" according to the invention.

Preferably, the light absorber which is at least in part inorganic is a material having perovskite structure or a material having 2D crystalline perovskite structure.

The term "perovskite" as used above and below denotes generally a material having a perovskite crystalline structure or a 2D crystalline perovskite structure.

The term perovskite solar cell (PSC) means a solar cell comprising a light absorber which is a material having perovskite structure or a material having 2D crystalline perovskite structure.

The light absorber which is at least in part inorganic is without limitation composed of a material having perovskite crystalline structure, a material having 2D crystalline perovskite structure (e.g. CrystEngComm, 2010,12, 2646-2662), $Sb_2S_3$ (stibnite), $Sb_2(S_xSe_{(x-1)})_3$, $PbS_xSe_{(x-1)}$, $CdS_xSe_{(x-1)}$, ZnTe, CdTe, $ZnS_xSe_{(x-1)}$, InP, FeS, $FeS_2$, $Fe_2S_3$, $Fe_2SiS_4$, $Fe_2GeS_4$, $Cu_2S$, CuInGa, $CuIn(Se_xS_{(1-x)})_2$, $Cu_3Sb_xBi_{(x-1)}$, $(S_ySe_{(y-1)})_3$, $Cu_2SnS_3$, $SnS_xSe_{(x-1)}$, $Ag_2S$, $AgBiS_2$, BiSI, BiSeI, $Bi_2(S_xSe_{(x-1)})_3$, $BiS_{(1-x)}Se_xI$, $WSe_2$, AlSb, metal halides (e.g. $BiI_3$, $Cs_2SnI_6$), chalcopyrite (e.g. $CuIn_xGa_{(1-x)}(S_ySe_{(1-y)})_2$), kesterite (e.g. $Cu_2ZnSnS_4$, $Cu_2ZnSn(Se_xS_{(1-x)})_4$, $Cu_2Zn(Sn_{1-x}Ge_x)S_4$) and metal oxide (e.g. CuO, $Cu_2O$) or a mixture thereof.

Preferably, the light absorber which is at least in part inorganic is a perovskite.

In the above definition for light absorber, x and y are each independently defined as follows: (0≤x≤1) and (0≤y≤1).

Very preferably, the light absorber is a special perovskite namely a metal halide perovskite as described in detail above and below. Most preferably, the light absorber is an organic-inorganic hybrid metal halide perovskite contained in the perovskite solar cell (PSC).

In one particularly preferred embodiment of the invention, the perovskite denotes a metal halide perovskite with the formula $ABX_3$, where A is a monovalent organic cation, a metal cation or a mixture of two or more of these cations B is a divalent cation and X is F, Cl, Br, I, $BF_4$ or a combination thereof.

Preferably, the monovalent organic cation of the perovskite is selected from alkylammonium, wherein the alkyl group is straight chain or branched having 1 to 6 C atoms, formamidinium or guanidinium or wherein the metal cation is selected from $K^+$, $Cs^+$ or $Rb^+$.

Suitable and preferred divalent cations B are $Ge^{2+}$, $Sn^{2+}$ or $Pb^{2+}$. Suitable and preferred perovskite materials are $CsSnI_3$, $CH_3NH_3Pb(I_{1-x}Cl_x)_3$, $CH_3NH_3PbI_3$, $CH_3NH_3Pb(I_{1-x}Br_x)_3$, $CH_3NH_3Pb(I_{1-x}(BF_4)x)_3$, $CH_3NH_3Sn(I_{1-x}Cl_x)_3$, $CH_3NH_3SnI_3$ or $CH_3NH_3Sn(I_{1-x}Br_x)_3$ wherein x is each independently defined as follows: (0<x≤1).

Further suitable and preferred perovskites may comprise two halides corresponding to formula $Xa_{(3-x)}Xb_{(x)}$, wherein Xa and Xb are each independently selected from Cl, Br, or I, and x is greater than 0 and less than 3.

Suitable and preferred perovskites are also disclosed in WO 2013/171517, claims 52 to 71 and claims 72 to 79, which is entirely incorporated herein by reference. The materials are defined as mixed-anion perovskites comprising two or more different anions selected from halide anions and chalcogenide anions. Preferred perovskites are disclosed on page 18, lines 5 to 17. As described, the perovskite is usually selected from $CH_3NH_3PbBrI_2$, $CH_3NH_3PbBrCl_2$, $CH_3NH_3PbIBr_2$, $CH_3NH_3PbICl_2$, $CH_3NH_3SnF_2Br$, $CH_3NH_3SnF_2I$ and $(H_2N=CH-NH_2)PbI_{3z}Br_{3(1-z)}$, wherein z is greater than 0 and less than 1.

The invention further relates to a solar cell comprising the light absorber, preferably a PSC, as described above and below, wherein the polymer of formula I is employed as a layer between one electrode and the light absorber layer.

The invention further relates to a solar cell comprising the light absorber, preferably a PSC, as described above and below, wherein the polymer of formula I is comprised in an electron-selective layer.

The electron selective layer is defined as a layer providing a high electron conductivity and a low hole conductivity favoring electron-charge transport.

The invention further relates to a solar cell comprising the light absorber, preferably a PSC, as described above and below, wherein the polymer of formula I is employed as electron transport material (ETM) or as hole blocking material as part of the electron selective layer.

Preferably, the polymer of formula I is employed as hole transport material (ETM).

In an alternative preferred embodiment, the polymer of formula I is employed as electron blocking material.

The device architecture of a PSC device according to the invention can be of any type known from the literature.

A first preferred device architecture of a PSC device according to the invention comprises the following layers (in the sequence from bottom to top):

optionally a substrate which, in any combination, can be
flexible or rigid and transparent, semi-transparent or non-transparent and electrically conductive or non-conductive;

a high work function electrode, preferably comprising a doped metal oxide, for example fluorine-doped tin oxide (FTO), tin-doped indium oxide (ITO), or aluminium-doped zinc oxide;

an electron-selective layer which comprises one or more electron-transporting materials, at least one of which is a polymer of formula I, and which, in some cases, can also be a dense layer and/or be composed of nanoparticles, and which preferably comprises a metal oxide such as $TiO_2$, $ZnO_2$, $SnO_2$, $Y_2O_5$, $Ga_2O_3$, $SrTiO_3$, $BaTiO_3$ or combinations thereof;

optionally a porous scaffold which can be conducting, semi-conducting or insulating, and which preferably comprises a metal oxide such as $TiO_2$, $ZnO_2$, $SnO_2$, $Y_2O_5$, $Ga_2O_3$, $SrTiO_3$, $BaTiO_3$, $Al_2O_3$, $ZrO_2$, $SiO_2$ or combinations thereof, and which is preferably composed of nanoparticles, nanorods, nanoflakes, nanotubes or nanocolumns;

a layer comprising a light absorber which is at least in part inorganic, particularly preferably a metal halide perovskite as described above which, in some cases, can also be a dense or porous layer and which optionally partly or fully infiltrates into the underlying layer;

optionally a hole selective layer, which comprises one or more hole-transporting materials, and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;

and a back electrode which can be metallic, for example made of Au, Ag, Al, Cu, Ca, Ni or combinations thereof, or non-metallic and transparent, semi-transparent or non-transparent.

A second preferred device architecture of a PSC device according to the invention comprises the following layers (in the sequence from bottom to top):

optionally a substrate which, in any combination, can be flexible or rigid and transparent, semi-transparent or non-transparent and electrically conductive or non-conductive;

a high work function electrode, preferably comprising a doped metal oxide, for example fluorine-doped tin oxide (FTO), tin-doped indium oxide (ITO), or aluminium-doped zinc oxide;

optionally a hole injection layer which, for example, changes the work function of the underlying electrode, and/or modifies the surface of the underlying layer and/or helps to planarize the rough surface of the underlying layer and which, in some cases, can also be a monolayer;

optionally a hole selective layer, which comprises one or more hole-transporting materials and which, in some cases, can also comprise additives such as lithium salts, for example LiY, where Y is a monovalent organic anion, preferably bis(trifluoromethylsulfonyl)imide, tertiary amines such as 4-tert-butylpyridine, or any other covalent or ionic compounds, for example tris(2-(1H-pyrazol-1-yl)-4-tert-butylpyridine)-cobalt(III) tris(bis(trifluoromethylsulfonyl)imide)), which can enhance the properties of the hole selective layer, for example the electrical conductivity, and/or facilitate its processing;

a layer comprising a light absorber which is at least in part inorganic, particularly preferably a metal halide perovskite as described or preferably described above;

an electron-selective layer, which comprises one or more electron-transporting materials, at least one of which is a polymer of formula I and which, in some cases, can also be a dense layer and/or be composed of nanoparticles, and which, for example, can comprise a metal oxide such as $TiO_2$, $ZnO_2$, $SnO_2$, $Y_2O_5$, $Ga_2O_3$, $SrTiO_3$, $BaTiO_3$ or combinations thereof, and/or which can comprise a substituted fullerene, for example [6,6]-phenyl $C_{61}$-butyric acid methyl ester, and/or which can comprise a molecular, oligomeric or polymeric electron-transport material, for example 2,9-Dimethyl-4,7-diphenyl-1,10-phenanthroline, or a mixture thereof;

and a back electrode which can be metallic, for example made of Au, Ag, Al, Cu, Ca, Ni or combinations thereof, or non-metallic and transparent, semi-transparent or non-transparent.

To produce electron selective layers in PSC devices according to the invention, the compounds of formula I, optionally together with other compounds or additives in the form of blends or mixtures, may be deposited by any suitable method. Liquid coating of devices is more desirable than vacuum deposition techniques. Solution deposition methods are especially preferred. Formulations comprising the compounds of formula I enable the use of a number of liquid coating techniques. Preferred deposition techniques include, without limitation, dip coating, spin coating, ink jet printing, nozzle printing, letter-press printing, screen printing, gravure printing, doctor blade coating, roller printing, reverse-roller printing, offset lithography printing, dry offset lithography printing, flexographic printing, web printing, spray coating, curtain coating, brush coating, slot die coating or pad printing. For the fabrication of PSC devices and modules, deposition techniques for large area coating are preferred, for example slot die coating or spray coating.

Formulations that can be used to produce electron selective layers in optoelectronic devices according to the invention, preferably in PSC devices comprise one or more compounds of formula I or preferred embodiments as described above in the form of blends or mixtures optionally together with one or more further electron transport materials and/or hole blocking materials and/or binders and/or other additives as described above and below, and one or more solvents.

The formulation may include or comprise, essentially consist of or consist of the said necessary or optional constituents as described above or below. All compounds or components which can be used in the formulations are either known or commercially available, or can be synthesised by known processes.

The formulation as described before may be prepared by a process which comprises:

(i) first mixing a polymer of formula I, optionally a binder or a precursor of a binder as described before, optionally a further electron transport material, optionally one or more further additives as described above and below and a solvent or solvent mixture as described above and below and (ii) applying such mixture to a substrate; and optionally evaporating the solvent(s) to form an electron selective layer according to the present invention.

In step (i) the solvent may be a single solvent for the polymer of formula I and the organic binder and/or further electron transport material may each be dissolved in a separate solvent followed by mixing the resultant solutions to mix the compounds.

Alternatively, the binder may be formed in situ by mixing or dissolving a polymer of formula I in a precursor of a binder, for example a liquid monomer, oligomer or crosslinkable polymer, optionally in the presence of a solvent, and depositing the mixture or solution, for example by dipping, spraying, painting or printing it, on a substrate to form a liquid layer and then curing the liquid monomer, oligomer or crosslinkable polymer, for example by exposure to radiation, heat or electron beams, to produce a solid layer. If a preformed binder is used it may be dissolved together with the compound formula I in a suitable solvent as described before, and the solution deposited for example by dipping, spraying, painting or printing it on a substrate to form a liquid layer and then removing the solvent to leave a solid layer. It will be appreciated that solvents are chosen which are able to dissolve all ingredients of the formulation, and which upon evaporation from the solution blend give a coherent defect free layer.

Besides the said components, the formulation as described before may comprise further additives and processing assistants. These include, inter alia, surface-active substances (surfactants), lubricants and greases, additives which modify the viscosity, additives which increase the conductivity, dispersants, hydrophobicising agents, adhesion promoters, flow improvers, antifoams, deaerating agents, diluents, which may be reactive or unreactive, fillers, assistants, processing assistants, dyes, pigments, stabilisers, sensitisers, nanoparticles and inhibitors.

Additives can be used to enhance the properties of the electron selective layer and/or the properties of any of the neighbouring layers and/or the performance of the optoelectronic device according to the invention.

Additives can also be used to facilitate the deposition, the processing or the formation of the electron selective layer and/or the deposition, the processing or the formation of any of the neighbouring layers. Preferably, one or more additives are used which enhance the electrical conductivity of the electron selective layer and/or passivate the surface of any of the neighbouring layers.

Suitable methods to incorporate one or more additives include, for example exposure to a vapor of the additive at atmospheric pressure or at reduced pressure, mixing a solution or solid containing one or more additives and a material or a formulation as described or preferably described before, bringing one or more additives into contact with a material or a formulation as described before, by thermal diffusion of one or more additives into a material or a formulation as described before, or by ion-implantantion of one or more additives into a material or a formulation as described before.

Additives used for this purpose can be organic, inorganic, metallic or hybrid materials. Additives can be molecular compounds, for example organic molecules, salts, ionic liquids, coordination complexes or organometallic compounds, polymers or mixtures thereof. Additives can also be particles, for example hybrid or inorganic particles, preferably nanoparticles, or carbon based materials such as fullerenes, carbon nanotubes or graphene flakes.

Examples for additives that can enhance the electrical conductivity are for example halogens (e.g. $I_2$, $Cl_2$, $Br_2$, ICl, $ICl_3$, IBr and IF), Lewis acids (e.g. $PF_5$, $AsF_5$, $SbF_5$, $BF_3$, $BCl_3$, $SbCl_5$, $BBr_3$ and $SO_3$), protonic acids, organic acids, or amino acids (e.g. HF, HCl, $HNO_3$, $H_2SO_4$, $HClO_4$, $FSO_3H$ and $ClSO_3H$), transition metal compounds (e.g. $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbC_{15}$, $TaCl_{15}$, $MoF_5$, $MoCs_5$, $WF_5$, $WCl_6$, $UF_6$ and $LnCl_3$ (wherein Ln is a lanthanoid)), anions (e.g. $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3$—), cations (e.g. $H^+$, $Li^+$, $Na^+$, $K^+$, $Rb^+$, $Cs^+$, $Co^{3+}$ and $Fe^{3+}$), $O_2$, redox active salts (e.g. $XeOF_4$, $(NO_2^+)(SbF_6^-)$, $(NO_2^+)(SbCl_6^-)$, $(NO_2^+)(BF_4^-)$, $NOBF_4$, $NOPF_6$, $AgClO_4$, $H_2IrCl_6$ and $La(NO_3)_3 \cdot 6H_2O$), strongly electron-accepting organic molecules (e.g. 2,3,5,6-tetrafluoro-7,7,8,8-tetracyanoquinodimethane ($F_4$-TCNQ)), transition metal oxides (e.g. $WO_3$, $Re_2O_7$ and $MoO_3$), metal-organic complexes of cobalt, iron, bismuth and molybdenum, $(p-BrC_6H_4)_3NSbCl_6$, bismuth (III) tris(trifluoroacetate), $FSO_2OOSO_2F$, acetylcholine, $R_4N^+$, (R is an alkyl group), $R_4P^+$ (R is a straight-chain or branched alkyl group 1 to 20), $R_6As^+$ (R is an alkyl group), $R_3S^+$ (R is an alkyl group) and ionic liquids (e.g. 1-Ethyl-3-methylimidazolium bis(trifluoromethylsulfonyl)imide). Suitable cobalt complexes beside of tris(2-(1H-pyrazol-1-yl)-4-tert-butylpyridine)-cobalt(III) tris(bis(trifluoromethylsulfonyl)imide)) are cobalt complex salts as described in WO 2012/114315, WO 2012/114316, WO 2014/082706, WO 2014/082704, EP 2883881 or JP 2013-131477.

Suitable lithium salts are beside of lithium bis(trifluoromethylsulfonyl)imide, lithium tris(pentafluoroethyl)trifluorophosphate, lithium dicyanamide, lithium methylsulfate, lithium trifluormethanesulfonate, lithium tetracyanoborate, lithium dicyanamide, lithium tricyanomethide, lithium thiocyanate, lithium chloride, lithium bromide, lithium iodide, lithium hexafluoroposphate, lithium tetrafluoroborate, lithium perchlorate, lithium hexafluoroantimonate, lithium hexafluoroarsenate or a combination of two or more. A preferred lithium salt is lithium bis(trifluoromethylsulfonyl) imide.

Preferably, the formulation comprises from 0.1 mM to 50 mM, preferably from 5 to 20 mM of the lithium salt.

Suitable device structures for PSCs comprising a compound formula I and a mixed halide perovskite are described in WO 2013/171517, claims 52 to 71 and claims 72 to 79, which is entirely incorporated herein by reference.

Suitable device structures for PSCs comprising a compound formula and a dielectric scaffold together with a perovskite are described in WO 2013/171518, claims 1 to 90 or WO 2013/171520, claims 1 to 94 which are entirely incorporated herein by reference.

Suitable device structures for PSCs comprising a polymer of formula I, a semiconductor and a perovskite are described in WO 2014/020499, claims 1 and 3 to 14, which is entirely incorporated herein by reference The surface-increasing scaffold structure described therein comprises nanoparticles which are applied and/or fixed on a support layer, e.g. porous $TiO_2$.

Suitable device structures for PSCs comprising a compounds of formula and comprising a planar heterojunction are described in WO 2014/045021, claims 1 to 39, which is entirely incorporated herein by reference. Such a device is characterized in having a thin film of a light-absorbing or light-emitting perovskite disposed between n-type (electron conducting) and p-type (hole-conducting) layers. Preferably, the thin film is a compact thin film.

The invention further relates to a method of preparing a PSC as described above or below, the method comprising the steps of:

providing a first and a second electrode;
providing an electron selective layer comprising a polymer of formula I.

The invention relates furthermore to a tandem device comprising at least one device according to the invention as described above and below. Preferably, the tandem device is a tandem solar cell.

The tandem device or tandem solar cell according to the invention may have two semi-cells wherein one of the semi cells comprises the compounds, oligomers or polymers in the active layer as described or preferably described above. There exists no restriction for the choice of the other type of semi cell which may be any other type of device or solar cell known in the art.

There are two different types of tandem solar cells known in the art. The so called 2-terminal or monolithic tandem solar cells have only two connections. The two subcells (or synonymously semi cells) are connected in series. Therefore, the current generated in both subcells is identical (current matching). The gain in power conversion efficiency is due to an increase in voltage as the voltages of the two subcells add up.

The other type of tandem solar cells is the so called 4-terminal or stacked tandem solar cell. In this case, both subcells are operated independently.

Therefore, both subcells can be operated at different voltages and can also generate different currents. The power conversion efficiency of the tandem solar cell is the sum of the power conversion efficiencies of the two subcells.

The invention furthermore relates to a module comprising a device according to the invention as described above.

The compounds and compositions of the present invention can also be used as dye or pigment in other applications, for example as an ink dye, laser dye, fluorescent marker, solvent dye, food dye, contrast dye or pigment in coloring paints, inks, plastics, fabrics, cosmetics, food and other materials.

The compounds and compositions of the present invention are also suitable for use in the semiconducting channel of an OFET. Accordingly, the invention also provides an OFET comprising a gate electrode, an insulating (or gate insulator) layer, a source electrode, a drain electrode and an organic semiconducting channel connecting the source and drain electrodes, wherein the organic semiconducting channel comprises a compound and compositions according to the present invention. Other features of the OFET are well known to those skilled in the art.

OFETs where an OSC material is arranged as a thin film between a gate dielectric and a drain and a source electrode, are generally known, and are described for example in U.S. Pat. Nos. 5,892,244, 5,998,804, 6,723,394 and in the references cited in the background section. Due to the advantages, like low cost production using the solubility properties of the compounds according to the invention and thus the processibility of large surfaces, preferred applications of these OFETs are such as integrated circuitry, TFT displays and security applications.

The gate, source and drain electrodes and the insulating and semiconducting layer in the OFET device may be arranged in any sequence, provided that the source and drain electrode are separated from the gate electrode by the insulating layer, the gate electrode and the semiconductor layer both contact the insulating layer, and the source electrode and the drain electrode both contact the semiconducting layer.

An OFET device according to the present invention preferably comprises:

a source electrode,
a drain electrode,
a gate electrode,
a semiconducting layer,
one or more gate insulator layers,
optionally a substrate,
wherein the semiconductor layer preferably comprises a polymer of formula I.

The OFET device can be a top gate device or a bottom gate device. Suitable structures and manufacturing methods of an OFET device are known to the skilled in the art and are described in the literature, for example in US 2007/0102696 A1.

The gate insulator layer preferably comprises a fluoropolymer, like e.g. the commercially available Cytop 809M® or Cytop 107M® (from Asahi Glass). Preferably the gate insulator layer is deposited, e.g. by spin-coating, doctor blading, wire bar coating, spray or dip coating or other known methods, from a formulation comprising an insulator material and one or more solvents with one or more fluoro atoms (fluorosolvents), preferably a perfluorosolvent. A suitable perfluorosolvent is e.g. FC75® (available from Acros, catalogue number 12380). Other suitable fluoropolymers and fluorosolvents are known in prior art, like for example the perfluoropolymers Teflon AF® 1600 or 2400 (from DuPont) or Fluoropel® (from Cytonix) or the perfluorosolvent FC 43® (Acros, No. 12377). Especially preferred are organic dielectric materials having a low permittivity (or dielectric contant) from 1.0 to 5.0, very preferably from 1.8 to 4.0 ("low k materials"), as disclosed for example in US 2007/0102696 A1 or U.S. Pat. No. 7,095,044.

In security applications, OFETs and other devices with semiconducting materials according to the present invention, like transistors or diodes, can be used for RFID tags or security markings to authenticate and prevent counterfeiting of documents of value like banknotes, credit cards or ID cards, national ID documents, licenses or any product with monetary value, like stamps, tickets, shares, cheques etc.

Alternatively, the compounds and compositions (hereinafter referred to as "materials") according to the present invention can be used in OLEDs, e.g. as the active display material in a flat panel display applications, or as backlight of a flat panel display like e.g. a liquid crystal display. Common OLEDs are realized using multilayer structures. An emission layer is generally sandwiched between one or more electron-transport and/or hole-transport layers. By applying an electric voltage electrons and holes as charge carriers move towards the emission layer where their recombination leads to the excitation and hence luminescence of the lumophor units contained in the emission layer. The materials according to the present invention may be employed in one or more of the charge transport layers and/or in the emission layer, corresponding to their electrical and/or optical properties. Furthermore their use within the emission layer is especially advantageous, if the materials according to the present invention show electroluminescent properties themselves or comprise electroluminescent groups or compounds. The selection, characterization as well as the processing of suitable monomeric, oligomeric and polymeric compounds or materials for the use in OLEDs is generally known by a person skilled in the art, see, e.g., Miller et al, *Synth. Metals,* 2000, 111-112, 31-34, Alcala, *J. Appl. Phys.,* 2000, 88, 7124-7128 and the literature cited therein.

According to another use, the materials according to the present invention, especially those showing photoluminescent properties, may be employed as materials of light sources, e.g. in display devices, as described in EP 0 889 350 A1 or by C. Weder et al., Science, 1998, 279, 835-837.

A further aspect of the invention relates to both the oxidised and reduced form of the materials according to the present invention. Either loss or gain of electrons results in formation of a highly delocalised ionic form, which is of high conductivity. This can occur on exposure to common dopants. Suitable dopants and methods of doping are known to those skilled in the art, e.g. from EP 0 528 662, U.S. Pat. No. 5,198,153 or WO 96/21659.

The doping process typically implies treatment of the semiconductor material with an oxidating or reducing agent in a redox reaction to form delocalised ionic centres in the material, with the corresponding counterions derived from the applied dopants. Suitable doping methods comprise for example exposure to a doping vapor in the atmospheric pressure or at a reduced pressure, electrochemical doping in a solution containing a dopant, bringing a dopant into contact with the semiconductor material to be thermally diffused, and ion-implantantion of the dopant into the semiconductor material.

When electrons are used as carriers, suitable dopants are for example halogens (e.g., $I_2$, $Cl_2$, $Br_2$, ICl, $ICl_{13}$, IBr and IF), Lewis acids (e.g., $PF_5$, $AsF_5$, $SbF_5$, $BF_3$, $BCl_3$, $SbCl_5$, $BBr_3$ and $SO_3$), protonic acids, organic acids, or amino acids (e.g., HF, HCl, $HNO_3$, $H_2SO_4$, $HClO_4$, $FSO_3H$ and $ClSO_3H$), transition metal compounds (e.g., $FeCl_3$, FeOCl, $Fe(ClO_4)_3$, $Fe(4-CH_3C_6H_4SO_3)_3$, $TiCl_4$, $ZrCl_4$, $HfCl_4$, $NbF_5$, $NbCl_5$, $TaCl_5$, $MoF_5$, $MoCl_5$, $WF_5$, $WCl_6$, $UF_6$ and $LnCl_3$ (wherein Ln is a lanthanoid), anions (e.g., $Cl^-$, $Br^-$, $I^-$, $I_3^-$, $HSO_4^-$, $SO_4^{2-}$, $NO_3^-$, $ClO_4^-$, $BF_4^-$, $PF_6^-$, $AsF_6^-$, $SbF_6^-$, $FeCl_4^-$, $Fe(CN)_6^{3-}$, and anions of various sulfonic acids, such as aryl-$SO_3^-$). When holes are used as carriers, examples of dopants are cations (e.g., $H^+$, $Li^+$, $Na^+$, $K^+$, $Rb^+$ and $Cs^+$), alkali metals (e.g., Li, Na, K, Rb, and Cs), alkaline-earth metals (e.g., Ca, Sr, and Ba), $O_2$, $XeOF_4$, $(NO_2^+)(SbF_6^-)$, $(NO_2^+)(SbCl_6^-)$, $(NO_2^+)(BF_4^-)$, $AgClO_4$, $H_2IrCl_6$, $La(NO_3)_3 \cdot 6H_2O$, $FSO_2OOSO_2F$, Eu, acetylcholine, $R_4N^+$, (R is an alkyl group), $R_4P^+$ (R is an alkyl group), $R_6As^+$ (R is an alkyl group), and $R_3S^+$ (R is an alkyl group).

The conducting form of the materials according to the present invention can be used as an organic "metal" in applications including, but not limited to, charge injection layers and ITO planarising layers in OLED applications, films for flat panel displays and touch screens, antistatic films, printed conductive substrates, patterns or tracts in electronic applications such as printed circuit boards and condensers.

The materials according to the present invention may also be suitable for use in organic plasmon-emitting diodes (OPEDs), as described for example in Koller et al., Nat. Photonics, 2008, 2, 684.

According to another use, the materials according to the present invention can be used alone or together with other materials in or as alignment layers in LCD or OLED devices, as described for example in US 2003/0021913. The use of charge transport compounds according to the present invention can increase the electrical conductivity of the alignment layer. When used in an LCD, this increased electrical conductivity can reduce adverse residual dc effects in the switchable LCD cell and suppress image sticking or, for example in ferroelectric LCDs, reduce the residual charge produced by the switching of the spontaneous polarisation charge of the ferroelectric LCs. When used in an OLED device comprising a light emitting material provided onto the alignment layer, this increased electrical conductivity can enhance the electroluminescence of the light emitting material.

The materials according to the present invention having mesogenic or liquid crystalline properties can form oriented anisotropic films as described above, which are especially useful as alignment layers to induce or enhance alignment in a liquid crystal medium provided onto said anisotropic film.

According to another use, the materials according to the present invention are suitable for use in liquid crystal (LC) windows, also known as smart windows.

The materials according to the present invention may also be combined with photoisomerisable compounds and/or chromophores for use in or as photoalignment layers, as described in US 2003/0021913 A1.

According to another use, the materials according to the present invention, especially their water-soluble derivatives (for example with polar or ionic side groups) or ionically doped forms, can be employed as chemical sensors or materials for detecting and discriminating DNA sequences. Such uses are described for example in L. Chen, D. W. McBranch, H. Wang, R. Helgeson, F. Wudl and D. G. Whitten, Proc. Natl. Acad. Sci. U.S.A., 1999, 96, 12287; D. Wang, X. Gong, P. S. Heeger, F. Rininsland, G. C. Bazan and A. J. Heeger, Proc. Natl. Acad. Sci. U.S.A., 2002, 99, 49; N. DiCesare, M. R. Pinot, K. S. Schanze and J. R. Lakowicz, Langmuir, 2002, 18, 7785; D. T. McQuade, A. E. Pullen, T. M. Swager, Chem. Rev., 2000, 100, 2537.

Unless the context clearly indicates otherwise, as used herein plural forms of the terms herein are to be construed as including the singular form and vice versa.

Throughout the description and claims of this specification, the words "comprise" and "contain" and variations of the words, for example "comprising" and "comprises", mean "including but not limited to", and are not intended to (and do not) exclude other components.

It will be appreciated that variations to the foregoing embodiments of the invention can be made while still falling within the scope of the invention.

Each feature disclosed in this specification, unless stated otherwise, may be replaced by alternative features serving the same, equivalent or similar purpose. Thus, unless stated otherwise, each feature disclosed is one example only of a generic series of equivalent or similar features.

All of the features disclosed in this specification may be combined in any combination, except combinations where at least some of such features and/or steps are mutually exclusive. In particular, the preferred features of the invention are applicable to all aspects of the invention and may be used in any combination. Likewise, features described in non-essential combinations may be used separately (not in combination).

Above and below, unless stated otherwise percentages are percent by weight and temperatures are given in degrees Celsius.

The invention will now be described in more detail by reference to the following examples, which are illustrative only and do not limit the scope of the invention.

Example 1

Polymer P1 was prepared as follows.

4-Bromo-5-chloro-7-(4-dodecyl-thiophen-2-yl)-benzo[1,2,5]thiadiazole

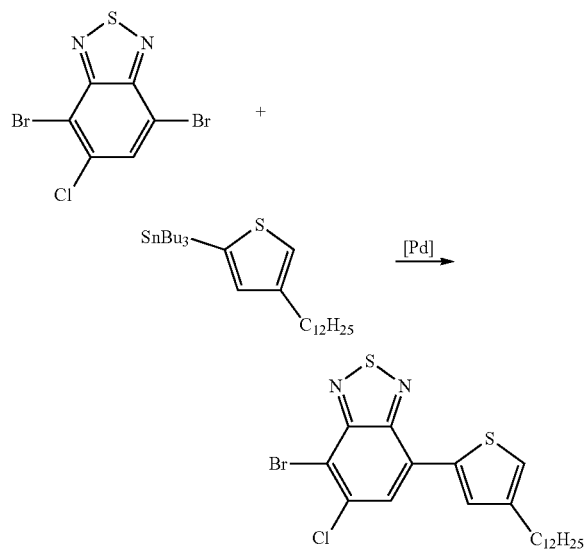

4,7-Dibromo-5-chloro-benzo[1,2,5]thiadiazole (3.00 g; 9.13 mmol; 1.00 eq.), tributyl-(4-dodecyl-thiophen-2-yl)-stannane (4.50 cm³; 9.13 mmol; 1.00 eq.) and tetrakis(triphenylphosphine)palladium(0) (0.32 g; 0.27 mmol; 0.03 eq.) are dissolved in a mixture of toluene (120.00 cm³) and dimethylformamide (30.00 cm³). The reaction mixture is degassed for 10 minutes before it is stirred at 120° C. for 12 hours. The solvent is removed in vacuo and the residue is dissolved in chloroform (30 cm³) at 50° C. The solution is triturated with methanol (150 cm³). The formed crystals are filtered off to afford orange solid (2.67 g, 58%).

¹H NMR (400 MHz, Chloroform-d) δ7.95 (d, J=1.3 Hz, 1H), 7.87 (s, 1H), 7.11 (d, J=1.3 Hz, 1H), 2.68 (t, J=7.7 Hz, 2H), 1.69 (quin, J=7.5 Hz, 2H), 1.44-1.16 (m, 21H), 0.92-0.81 (m, 3H).

5-Chloro-7-(4-dodecyl-thiophen-2-yl)-4-thiophen-2-yl-benzo[1,2,5]thiadiazole

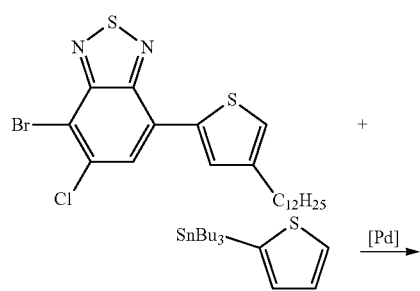

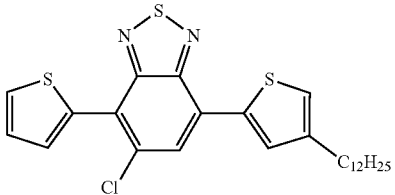

To a dry flask is added 4-bromo-5-chloro-7-(4-dodecyl-thiophen-2-yl)benzo[1,2,5]thiadiazole (2.50 g; 5.00 mmol; 1.00 eq.), tributyl-thiophen-2-yl-stannane (1.59 cm³; 5.00 mmol; 1.00 eq.) and tetrakis(triphenylphosphine)palladium (0) (0.17 g; 0.15 mmol; 0.03 eq.). The flask is evacuated and nitrogen purged before toluene (120.00 cm³) and N,N-dimethylformamide (30.00 cm³) are added. The reaction mixture is degassed for 10 minutes before it is stirred at 120° C. for 12 hours. Upon cooling to room temperature, the reaction mixture is concentrated in vacuo, The crude product is filtered off and the residue is washed with methanol (50 cm³) and 2-propanol (50 cm³). The product is recrystallized from hot 2-propanol.

1H NMR (400 MHz, Chloroform-d) δ7.99 (d, J=1.4 Hz, 1H), 7.94 (s, 1H), 7.76 (dd, J=3.7, 1.2 Hz, 1H), 7.60 (dd, J=5.1, 1.2 Hz, 1H), 7.25-7.23 (m, 1H), 7.11 (s, 1H), 1.75-1.65 (m, 2H), 1.26 (s, 20H), 0.87 (m, 3H).

7-(5-Bromo-4-dodecyl-thiophen-2-yl)-4-(5-bromo-thiophen-2-yl)-5-chloro-benzo[1,2,5]thiadiazole

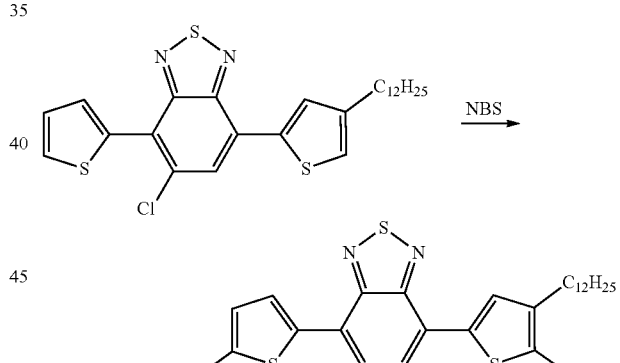

5-Chloro-7-(4-dodecyl-thiophen-2-yl)-4-thiophen-2-yl-benzo[1,2,5]thiadiazole (0.80 g; 1.59 mmol; 1.00 eq) is dissolved in mixture of trichloromethane (52.67 cm³) and acetic acid (4.86 cm³) at 0° C. To this mixture, 1-bromo-pyrrolidine-2,5-dione (0.91 g, 5.09 mmol, 3.20 eq) is added portion wise. The cooling bath is removed and reaction mixture is stirred at 23° C. for 12 hours. The reaction mixture is concentrated in vacou and crude product is purified by flash chromatography using petroleum ether (80-100° C.):dichloromethane mixture 9:1. The pure product is isolated in 36% yield (0.40 g)

¹H NMR (400 MHz, Chloroform-d) δ7.84 (s, 1H), 7.76 (s, 1H), 7.64 (d, J=4.0 Hz, 1H), 7.19 (d, J=4.0 Hz, 1H) 2.64 (t, J=7.8 Hz, 2H), 1.69 (quin, J=7.5 Hz, 2H), 1.44-1.16 (m, 21H), 0.92-0.81 (m, 3H).

Poly-(7-(4-dodecyl-thiophen-2-yl)-4-(thiophen-2-yl)-5-chloro-benzo[1,2,5]thiadiazole)-alt-ran-(4,8-bis(5-(2-hexyldecyl)-thiophene-2-yl)-benzodithiophene) (P1)

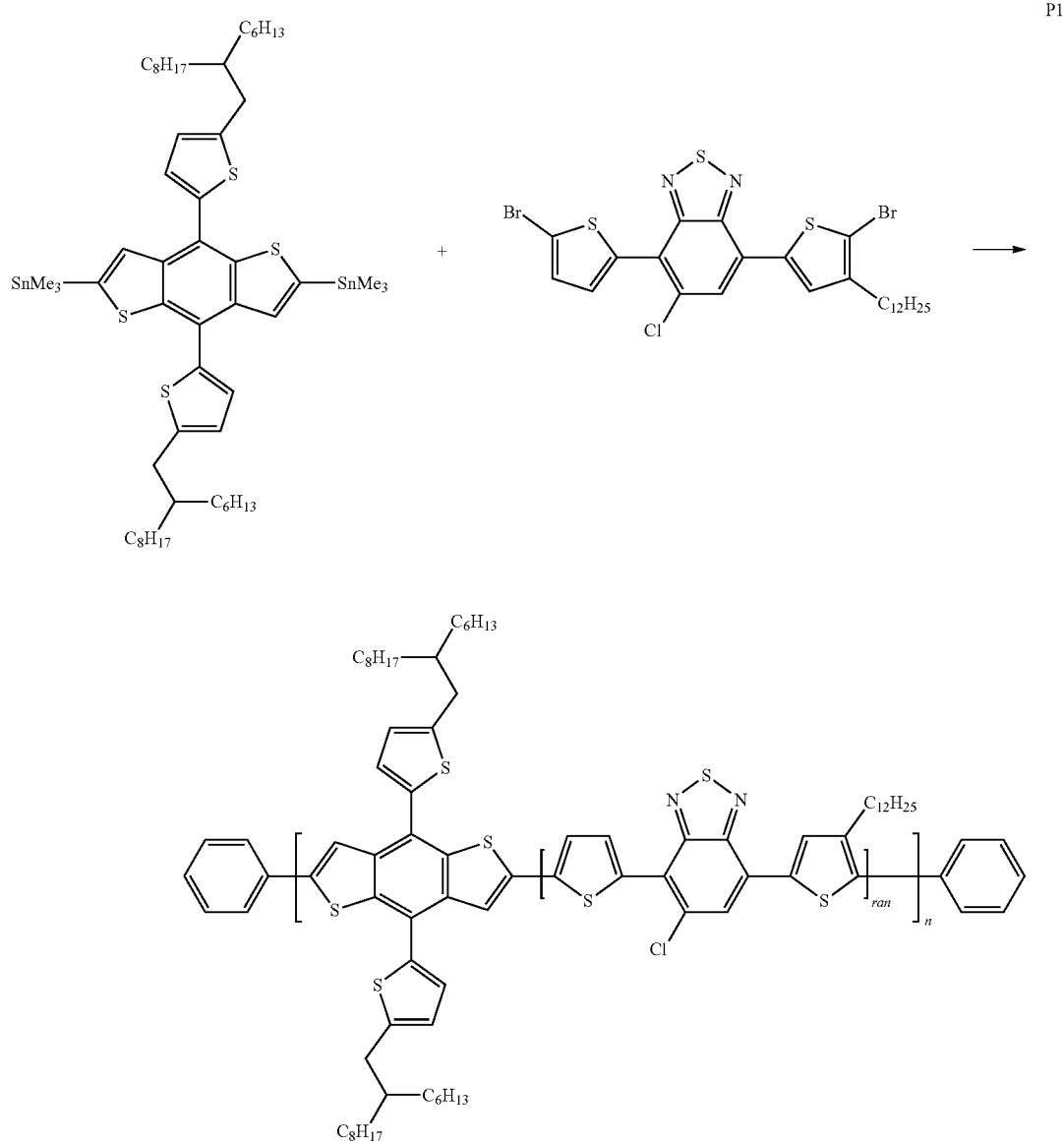

7-(5-Bromo-4-dodecyl-thiophen-2-yl)-4-(5-bromo-thiophen-2-yl)-5-chloro-benzo[1,2,5]-thiadiazole (218.4 mg; 0.33 mmol; 1.00 eq.), 4,8-bis-[5-(2-hexyl-decyl)-thiophen-2-yl]-2,6-bis-trimethylstannanol-benzo[1,2-b;4,5-b']dithiophene (373.0 mg; 0.33 mmol; 1.00 eq.), tris(dibenzylideneacetone)dipalladium(0) (12.1 mg; 0.01 mmol; 0.04 eq.) and tri(o-tolyl)phosphine (12.1 mg; 0.04 mmol; 0.12 eq.) are placed in a flask under nitrogen. Degassed chlorobenzene (25.00 cm³) is added and the mixture is degassed for 10 minutes. The reaction mixture is heated to 120° C. and stirred at this temperature for 5 hours. Tributyl-phenyl-stannane (0.32 cm³; 0.99 mmol; 3.00 eq.) is then added and mixture is stirred for an additional hour at 120° C. Next bromobenzene (0.35 cm³; 3.30 mmol; 10.00 eq.) is added and mixture is stirred for an additional hour. The reaction mixture is allowed to cool to 65° C. and precipitated into stirred methanol (250 cm³). The polymer is collected by filtration and washed with methanol (2×10 cm³) to give a solid. The polymer is subjected to sequential Soxhlet extraction with acetone, petroleum ether (40-60° C.), cyclohexane, chloroform. The chloroform fraction is concentrated in vacuo to 20 cm³, precipitated into stirred methanol (150 cm³) and collected by filtration to give a black solid (317 mg, Yield: 74%). GPC (50° C., chlorobenzene) $M_n$=23.0 kg mol$^{-1}$; $M_w$=68.6 kg mol-1; PDI=3.0.

Example 2

Polymer P2 was prepared as follows.

4-Bromo-5-chloro-7-(4-(2-ethylhexyl)-thiophen-2-yl)-benzo[1,2,5]thiadiazole

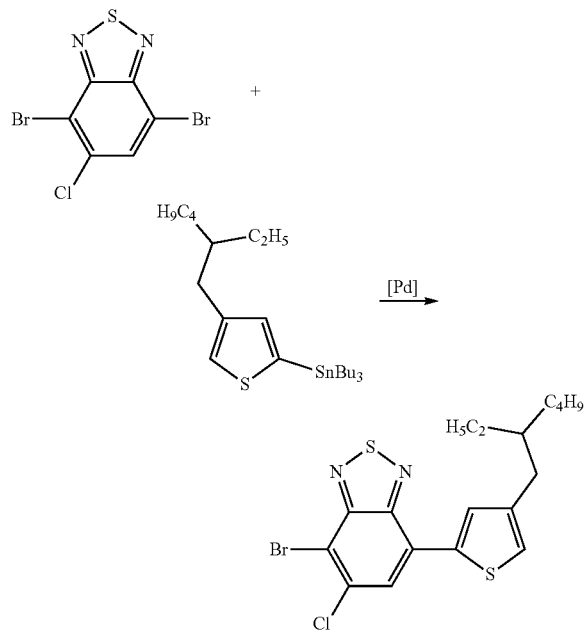

4,7-Dibromo-5-chloro-benzo[1,2,5]thiadiazole (2.50 g; 7.61 mmol; 1.00 eq.), tributyl-(4-(2-ethylhexyl)-thiophen-2-yl)-stannane (3.70 g; 7.61 mmol; 1.00 eq.) and tetrakis (triphenylphosphine)palladium(0) (0.26 g; 0.23 mmol; 0.03 eq.) are dissolved in a mixture of toluene (90.00 cm³) and N,N-dimethylformamide (20.00 cm³). The reaction mixture is degassed for 10 minutes before it is stirred at 120° C. for 12 hours. The solvent is removed in vacuo resulting in a yellow oil. The crude product is purified on column chromatography using a mixture of petrol ether (40-60) and dichloromethane to afford product in 62% yield (2.1 g).

$^1$H NMR (400 MHz, Chloroform-d) δ7.92 (d, J=1.4 Hz, 1H), 7.86 (s, 1H), 7.08 (d, J=1.3 Hz, 1H), 2.62 (d, J=6.9 Hz, 2H), 1.64 (quin, J=7.5 Hz, 1H), 1.39-1.24 (m, 8H), 0.93-0.86 (m, 6H).

5-Chloro-7-(4-(2-ethylhexyl)-thiophen-2-yl)-4-thiophen-2-yl-benzo[1,2,5]thiadiazole

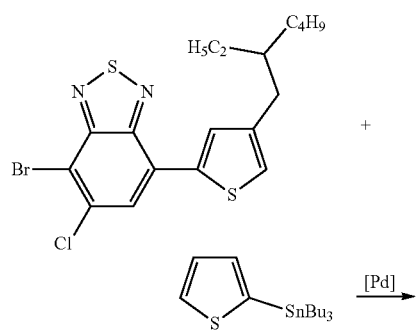

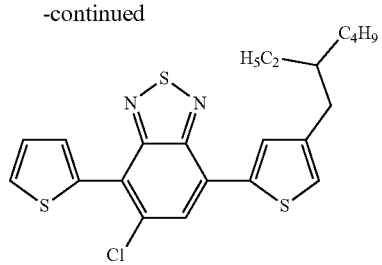

To a dry flask is added 4-bromo-5-chloro-7-(4-(2-ethylhexyl)-thiophen-2-yl)benzo[1,2,5]thiadiazole (2.10 g; 4.73 mmol; 1.00 eq.), tributyl-thiophen-2-yl-stannane (1.50 cm³; 4.73 mmol; 1.00 eq.) and tetrakis(triphenylphosphine)palladium(0) (0.16 g; 0.14 mmol; 0.03 eq.). The flask is evacuated and nitrogen purged before toluene (90.00 cm³) and N,N-dimethylformamide (20.00 cm³) are added. The reaction mixture is degassed for 10 minutes before it is stirred at 120° C. for 12 hours. Upon cooling to 23° C., the reaction mixture is concentrated in vacuo. The crude product is used for the next synthetic step without further purification.

7-(5-Bromo-4-(2-ethylhexyl)-thiophen-2-yl)-4-(5-bromo-thiophen-2-yl)-5-chloro-benzo[1,2,5]thiadiazole

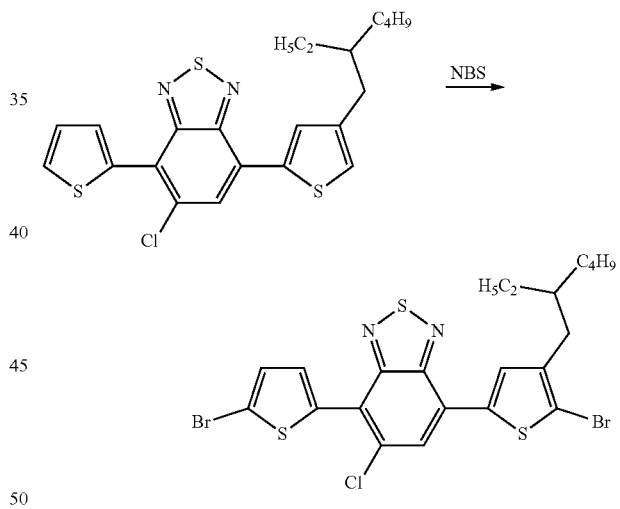

5-Chloro-7-(4-(2-ethylhexyl)-thiophen-2-yl)-4-thiophen-2-yl-benzo[1,2,5]thiadiazole (1.28 g; 2.86 mmol; 1.00 eq) is dissolved in mixture of trichloromethane (50.00 cm³) and acetic acid (10.0 cm³) at 0° C. To this mixture, 1-bromo-pyrrolidine-2,5-dione (1.12 g, 6.30 mmol, 2.20 eq) is added portion wise. The cooling bath is removed and the reaction mixture is stirred at 23° C. for 12 hours. The reaction mixture is concentrated in vacuo and the crude product is purified by flash chromatography using petroleum ether (80-100° C.):dichloromethane mixture. The pure product is isolated in 54% yield (0.94 g)

$^1$H NMR (400 MHz, Chloroform-d) 7.83 (s, 1H), 7.72 (s, 1H), 7.63 (d, k=4.0 Hz, 1H), 7.19 (d, J=4.0 Hz, 1H), 2.57 (d, J=7.2 Hz, 2H), 1.69 (quin, J=5.8 Hz, 1H), 1.41-1.24 (m, 8H), 0.95-0.86 (m, 6H).

Poly-(7-(4-(2-ethylhexyl)thiophen-2-yl)-4-(thiophen-2-yl)-5-chloro-benzo[1,2,5]thiadiazole)-alt-ran-(4,8-bis(5-(2-hexyldecyl)-thiophene-2-yl)-benzodithiophene) (P2)

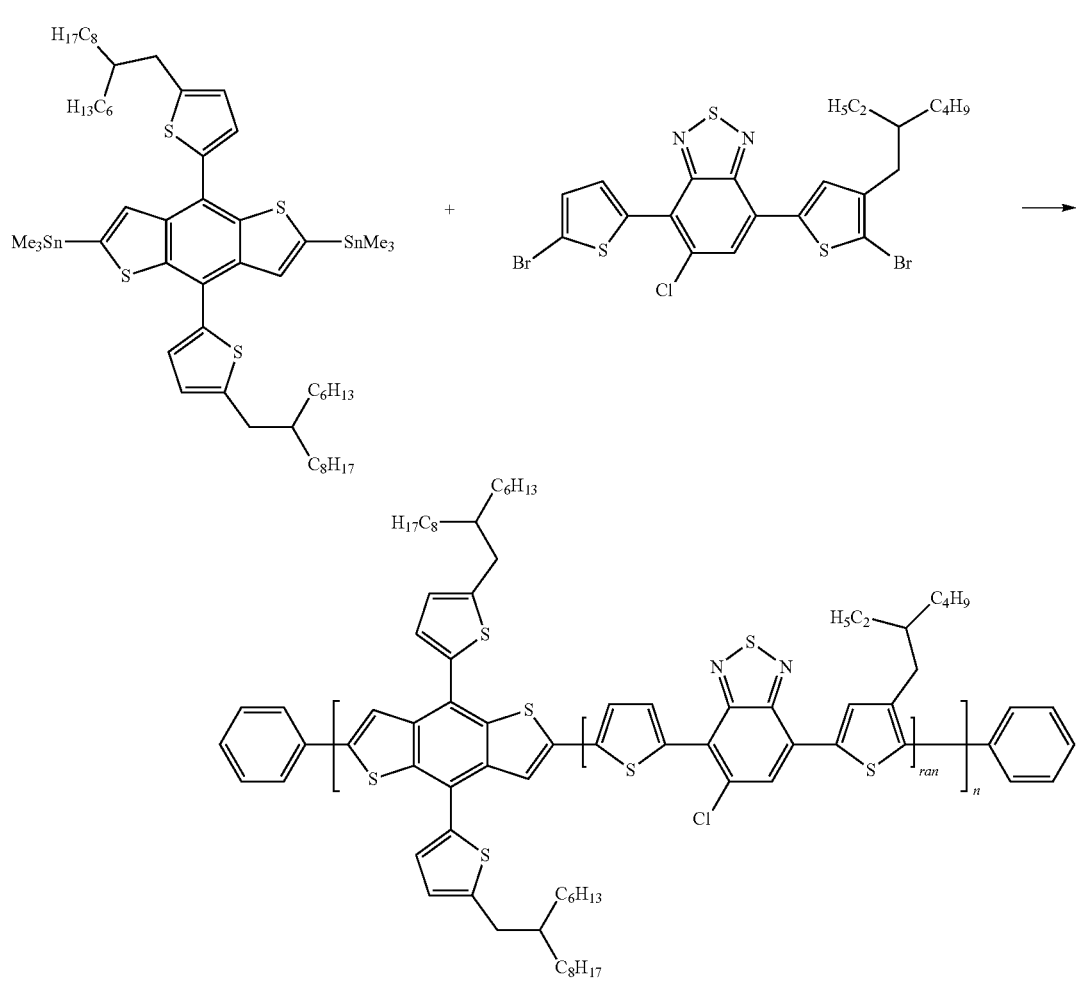

7-(5-Bromo-4-(2-ethylhexyl)-thiophen-2-yl)-4-(5-bromo-thiophen-2-yl)-5-chloro-benzo[1,2,5]-thiadiazole (292.8 mg; 0.48 mmol; 1.00 eq.), 4,8-bis-[5-(2-hexyldecyl)-thiophen-2-yl]-2,6-bis-trimethylstannanyl-benzo[1,2-b;4,5-b']dithiophene (546.5 mg; 0.48 mmol; 1.00 eq.), tris(dibenzylideneacetone)dipalladium(0) (4.43 mg; 0.01 mmol; 0.01 eq.) and tri(o-tolyl)phosphine (11.8 mg; 0.04 mmol; 0.08 eq.) are placed in a flask under nitrogen. Degassed toluene (15.00 cm³) is added and the mixture is degassed for 10 minutes. The reaction mixture is heated to 120° C. and stirred at this temperature for 3 hours.

Tributyl-phenyl-stannane (0.47 cm³; 1.45 mmol; 3.00 eq.) is then added and mixture is stirred for an additional hour at 120° C. Next bromobenzene (0.51 cm³; 4.84 mmol; 10.00 eq.) is added and mixture is stirred for an additional hour. The reaction mixture is allowed to cool to 65° C. and precipitated into stirred methanol (150 cm³). The polymer is collected by filtration and washed with methanol (2×10 cm³) to give a solid. The polymer is subjected to sequential Soxhlet extraction with acetone, petroleum ether (40-60° C.) and cyclohexane. The cyclohexane fraction is concentrated in vacuo to 20 cm³, precipitated into stirred methanol (150 cm³) and collected by filtration to give a black solid (529 mg, Yield: 87%). GPC (50° C., chlorobenzene) $M_n$=14.5 kg mol⁻¹; $M_w$=35.0 kg mol-1; PDI=2.4.

Example 3

Polymer P3 was prepared as follows.

4-Bromo-5-fluoro-7-(4-dodecyl-thiophen-2-yl)-benzo[1,2,5]thiadiazole

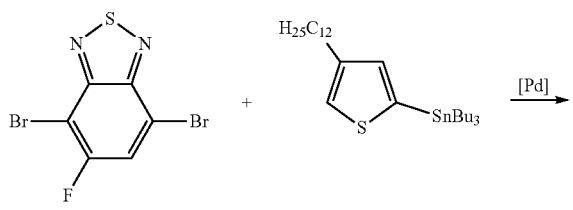

-continued

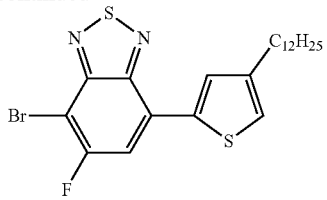

4,7-Dibromo-5-fluoro-benzo[1,2,5]thiadiazole (3.00 g; 9.62 mmol; 1.00 eq.), tributyl-(4-dodecyl-thiophen-2-yl)-stannane (5.21 g; 9.62 mmol; 1.00 eq.) and tetrakis(triphenylphosphine)palladium(0) (0.33 g; 0.29 mmol; 0.03 eq.) are dissolved in a mixture of toluene (120.00 cm$^3$) and dimethylformamide (30.00 cm$^3$). The reaction mixture is degassed for 10 minutes before it is stirred at 120° C. for overnight, then cooled to 23° C. The solvent is removed in vacuo. The crude product is dissolved in dichloromethane, precipitated by addition of methanol and filtered off. The product is purified on silica using a mixture of petrol ether (40-60) and dichloromethane. The product was isolated in 69% yield (3.23 g).

$^1$H NMR (400 MHz, Chloroform-d) δ7.91 (d, J=1.3 Hz, 1H), 7.62 (d, J=10.1 Hz, 1H), 7.05 (d, J=1.3 Hz, 1H), 2.62 (t, J=7.7 Hz, 2H), 1.62 (quin, J=7.4 Hz, 2H), 1.42-1.17 (m, 18H), 0.80 (t, J=6.9 Hz, 3H).

7-(4-Dodecyl-thiophen-2-yl)-5-fluoro-4-thiophen-2-yl-benzo[1,2,5]thiadiazole

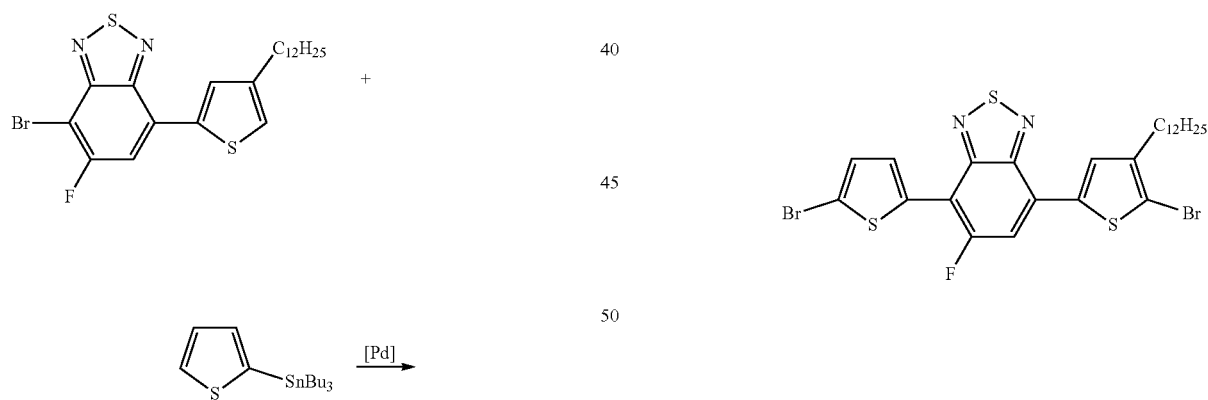

4-Bromo-5-fluoro-7-(4-dodecyl-thiophen-2-yl)benzo[1,2,5]thiadiazole (3.23 g; 6.68 mmol; 1.00 eq.), tributyl-thiophen-2-yl-stannane (2.12 cm$^3$; 6.68 mmol; 1.00 eq.) and tetrakis(triphenylphosphine)palladium(0) (0.23 g; 0.20 mmol; 0.03 eq.) are placed in a flask. The flask is evacuated and nitrogen purged before toluene (90.00 cm$^3$) and N,N-dimethylformamide (20.00 cm$^3$) are added. The reaction mixture is degassed for 10 minutes before it is stirred at 120° C. overnight. Upon cooling to 23° C., the reaction mixture is concentrated in vacuo, The crude product dissolved in dichloromethane (20 cm$^3$) and precipitated by addition of methanol. The product is suction filtered off and recrystallized from hot 2-propanol (100 ml). The product is isolated in 85% yield (2.78 g)

1H NMR (400 MHz, Methylene Chloride-d$_2$) δ8.26 (d, J=3.7 Hz, 1H), 7.98 (s, 1H), 7.74 (d, J=13.1 Hz, 1H), 7.57 (d, J=5.0 Hz, 1H), 7.24 (t, J=4.5 Hz, 1H), 7.12 (s, 1H), 2.68 (t, J=7.8 Hz, 2H), 1.69 (quin, J=7.5 Hz, 2H), 1.46-1.17 (m, 18H), 0.88 (t, J=6.6 Hz, 3H).

7-(5-Bromo-4-dodecyl-thiophen-2-yl)-4-(5-bromo-thiophen-2-yl)-5-fluoro-benzo[1,2,5]thiadiazole 7-(4-Dodecyl-thiophen-2-yl)-5-fluoro-4-thiophen-2-yl-benzo[1,2,5]thiadiazole (2.60 g; 5.34 mmol; 1.00 eq) is dissolved in mixture of trichloromethane (150.00 cm$^3$) and acetic acid (20.00 cm$^3$) at 0° C. To this mixture, 1-bromo-pyrrolidine-2,5-dione (2.09 g, 11.75 mmol, 2.20 eq) is added portion wise. The cooling bath is removed and the reaction mixture is stirred at room temperature for overnight. The reaction mixture is concentrated in vacuo and the crude product is recrystallized from hot 2-propanol (600 ml). Yield: 2.42 g 70%).

¹H NMR (400 MHz, Methylene Chloride-d₂) δ8.03 (d, J=4.1 Hz, 1H), 7.78 (s, 1H), 7.69 (d, J=13.1 Hz, 1H), 7.20 (d, J=1.3 Hz, 1H), 2.64 (t, J=7.7 Hz, 2H), 1.67 (quin, J=7.3 Hz, 2H), 1.44-1.19 (m, 18H), 0.87 (t, J=6.8 Hz, 3H).

Poly-(7-(4-dodecyl-thiophen-2-yl)-4-(thiophen-2-yl)-5-chloro-benzo[1,2,5]thiadiazole)-alt-ran-(4,8-bis(5-(2-hexyldecyl)-thiophene-2-yl)-benzodithiophene) (P3)

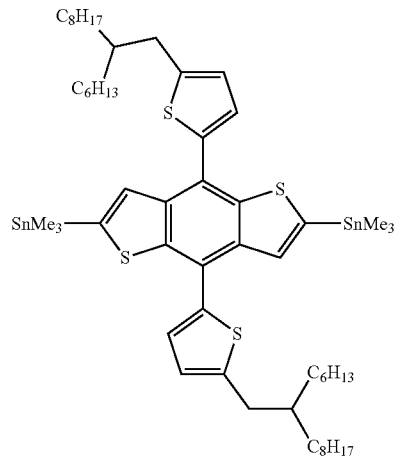

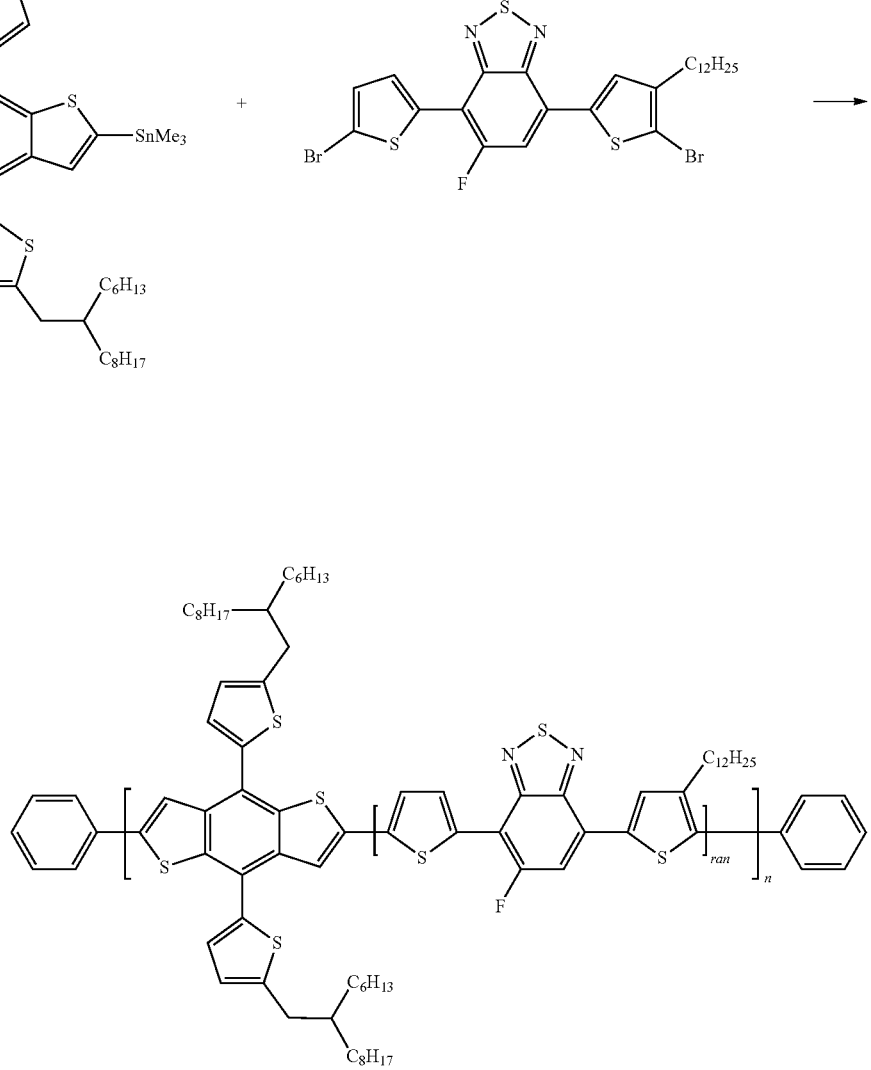

7-(5-Bromo-4-dodecyl-thiophen-2-yl)-4-(5-bromo-thiophen-2-yl)-5-fluoro-benzo[1,2,5]-thiadiazole (414.2 mg; 0.64 mmol; 1.00 eq.), 4,8-bis-[5-(2-hexyl-decyl)-thiophen-2-yl]-2,6-bis-trimethylstannanyl-benzo[1,2-b;4,5-b']dithiophene (725.5 mg; 0.64 mmol; 1.00 eq.), tris(dibenzylidene-acetone)dipalladium(0) (5.88 mg; 0.01 mmol; 0.01 eq.) and tri(o-tolyl) phosphine (15.6 mg; 0.05 mmol; 0.08 eq.) are placed in a flask under nitrogen. Degassed chlorobenzene (20.00 cm³) is added and the mixture is degassed for 10 minutes. The reaction mixture is heated to 120° C. and stirred at this temperature for 3 hours.

Tributyl-phenyl-stannane (0.21 cm³; 0.64 mmol; 1.00 eq.) is then added and mixture is stirred for an additional hour at 120° C. Next bromobenzene (0.67 cm³; 6.43 mmol; 10.00 eq.) is added and mixture is stirred for additional 2 hours. The reaction mixture cooled to rt and precipitated into stirred methanol (250 cm³). The polymer is collected by filtration and washed with methanol (2×10 cm³) to give a solid. The polymer is sequentially extracted using a Soxhlet apparatus with acetone, petroleum ether (40-60° C.), cyclohexane and chloroform. The chloroform fraction is concentrated in vacuo to 30 cm³, precipitated into stirred methanol (150 cm³) and collected by filtration to give a black solid (657 mg, Yield: 76%). GPC (50° C., chlorobenzene) $M_n$=43.2 kg mol⁻¹; $M_w$=162.4 kg mol⁻¹; PDI=3.76.

Example 4

Polymer P4 was prepared as follows.

Poly-(7-(4-dodecyl-thiophen-2-yl)-4-(thiophen-2-yl)-5-chloro-benzo[1,2,5]thiadiazole)-alt-ran-(4,8-bis(4,5-dioctyl-thiophene-2-yl)-benzodithiophene) (P4)

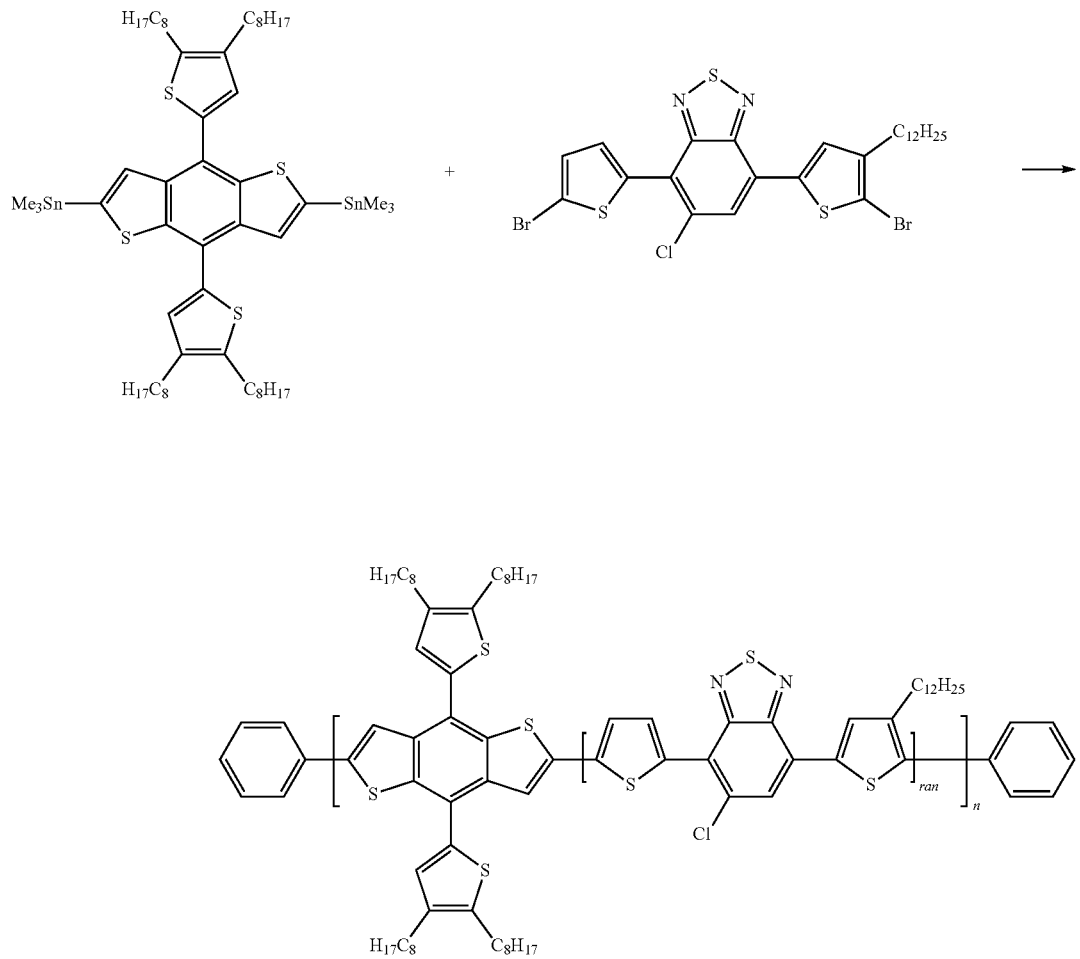

7-(5-Bromo-4-dodecyl-thiophen-2-yl)-4-(5-bromo-thiophen-2-yl)-5-chloro-benzo[1,2,5]-thiadiazole (210.0 mg; 0.32 mmol; 1.00 eq.), 4,8-Bis-(4,5-dioctyl-thiophen-2-yl)-2,6-bis-trimethylstannanyl-benzo[1,2-b;4,5-b']dithiophene (358.7 mg; 0.32 mmol; 1.00 eq.), tris(dibenzylideneacetone)dipalladium(0) (5.8 mg; 0.005 mmol; 0.02 eq.) and tri(o-tolyl)phosphine (11.6 mg; 0.04 mmol; 0.12 eq.) are placed in a flask under nitrogen. Degassed chlorobenzene (25.00 cm$^3$) is added and the mixture is degassed for 10 minutes. The reaction mixture is heated to 120° C. and stirred at this temperature for 5 hours.

Tributyl-phenyl-stannane (0.31 cm$^3$; 0.95 mmol; 3.00 eq.) is then added and mixture is stirred for an additional hour at 120° C. Next bromobenzene (0.35 cm$^3$; 3.30 mmol; 10.00 eq.) is added and mixture is stirred for an additional hour. The reaction mixture is allowed to cool to 65° C. and precipitated into stirred methanol (250 cm$^3$). The polymer is collected by filtration and washed with methanol (2×10 cm$^3$) to give a solid. The polymer is subjected to sequential Soxhlet extraction with acetone, petroleum ether (40-60° C.), cyclohexane. The cyclohexane fraction is concentrated in vacuo to 20 cm$^3$, precipitated into stirred methanol (150 cm$^3$) and collected by filtration to give a black solid (394 mg, Yield: 93%). GPC (50° C., chlorobenzene) $M_n$=26.8 kg mol$^{-1}$; $M_w$=55.2 kg mol$^{-1}$; PDI=2.1.

Comparison Example 1

Polymer C1 (Poly-(4-(4-dodecyl-thiophen-2-yl)-7-(thiophen-2-yl)-5-chloro-benzo[1,2,5]thiadiazole)-alt-ran-(4,8-bis(5-(2-hexyldecyl)-thiophene-2-yl)-benzodithiophene)) was synthesized in analogy to the procedure as described in D. Mo et al., *Chem. Mater.* 2017, 29, 2819.

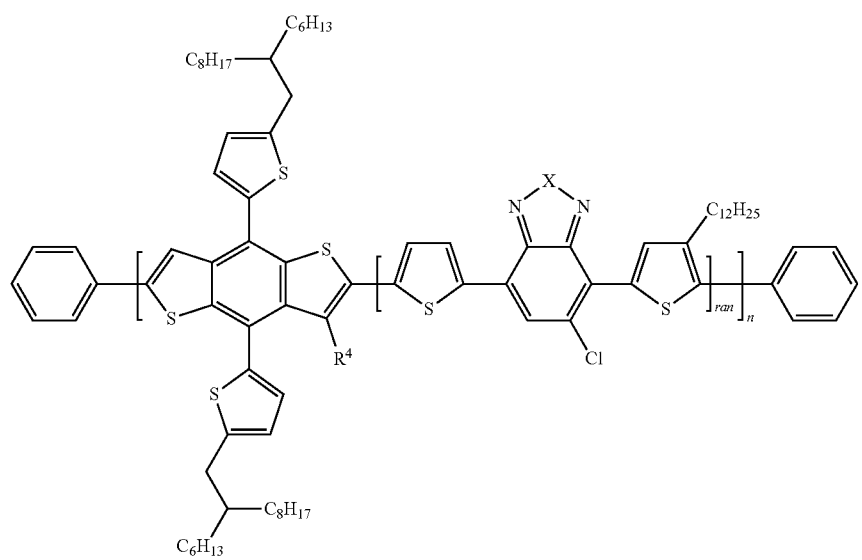

C1

Use Example A

A1: Inverted Bulk Heterojunction Organic Photovoltaic Devices

Organic photovoltaic (OPV) devices are fabricated on pre-patterned ITO-glass substrates (13Ω/sq.). Substrates are cleaned using common solvents (acetone, iso-propanol, deionized-water) in an ultrasonic bath. A layer of commercially available aluminium zinc oxide (AlZnO, Nanograde) was applied as a uniform coating by doctor blade at 40° C. The AlZnO films are then annealed at 100° C. for 10 minutes in air. Active material solutions (i.e. polymer+acceptor) are prepared to fully dissolve the solutes at a 23 mg·cm$^{-3}$ or 25 mg·cm$^{-3}$ solution concentration. Thin films are blade-coated in air atmosphere to achieve active layer thicknesses between 50 and 800 nm as measured using a profilometer. A short drying period follows to ensure removal of any residual solvent.

Typically, blade-coated films are dried at 60° C. for 2 minutes on a hotplate. On top of the active layer 0.1 mL of a conducting polymer poly(ethylene dioxythiophene) doped with poly(styrene sulfonic acid) [PEDOT:PSS HTL 4083 (Heraeus)] was spread and uniformly coated by doctor blade at 70° C. Afterwards Ag (100 nm) cathodes are thermally evaporated through a shadow mask to define the cells.

Table 1 shows structures of non-fullerene acceptors used in the following examples. Preparation of NFA1-NFA7 is disclosed in WO2018065350. ITIC was published by Y. Lin, J. Wang, Z.-G. Zhang, H. Bai, Y. Li, D. Zhu and X. Zhan, *Adv. Mater.* 2015, 27, 1170-1174

TABLE 1

Structures of non-fullerene acceptors

| # | Structure |
|---|---|
| NFA1 | 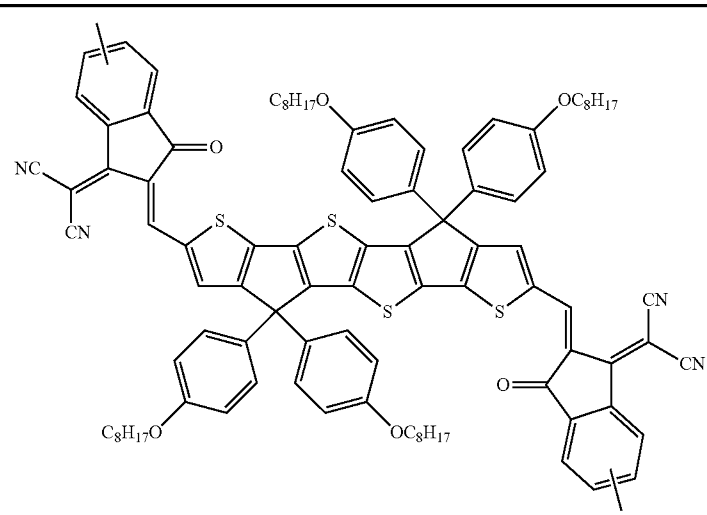 |

TABLE 1-continued

Structures of non-fullerene acceptors

| # | Structure |
| --- | --- |
| NFA2 | 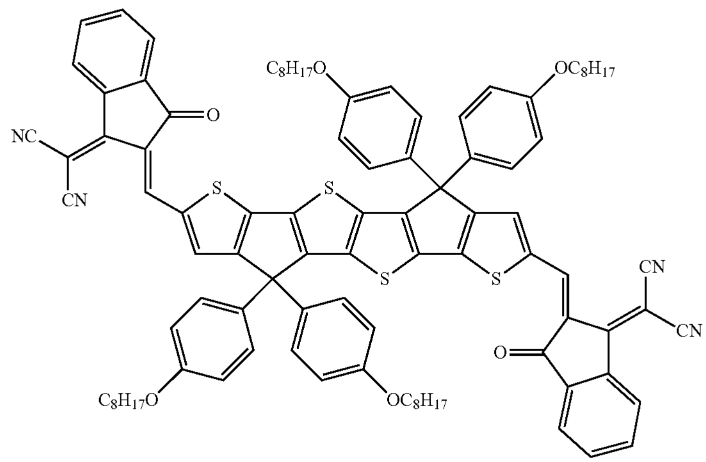 |
| NFA3 | 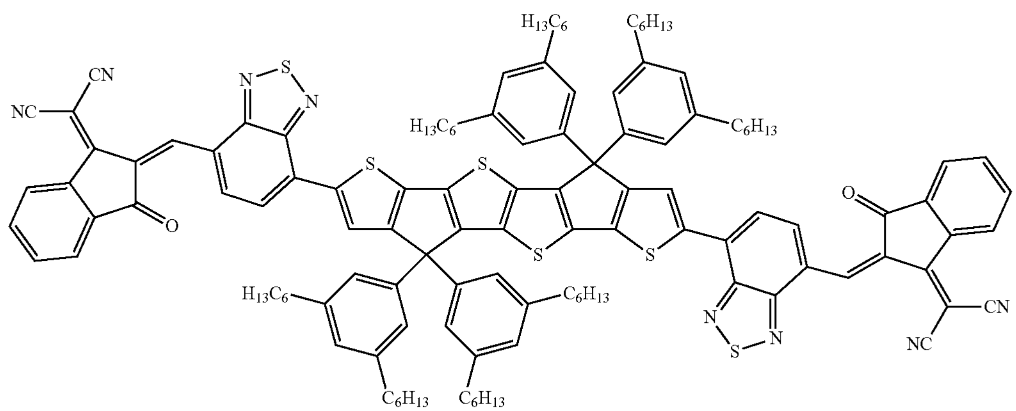 |
| NFA4 | 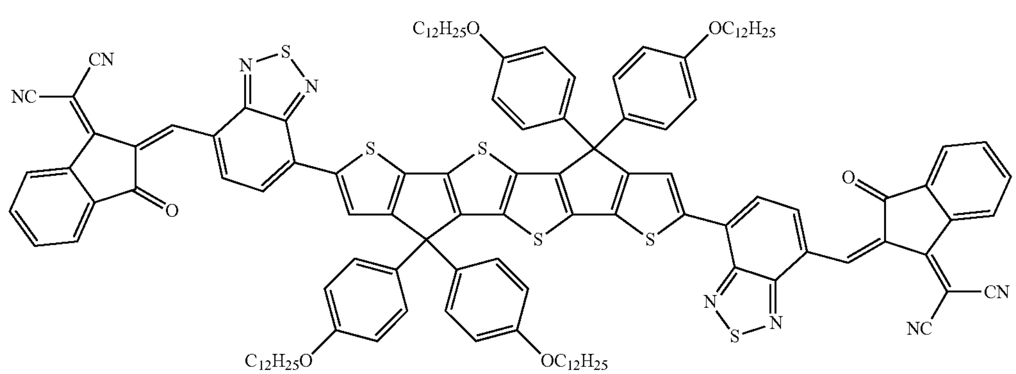 |

TABLE 1-continued

Structures of non-fullerene acceptors

| # | Structure |
|---|---|
| NFA5 | 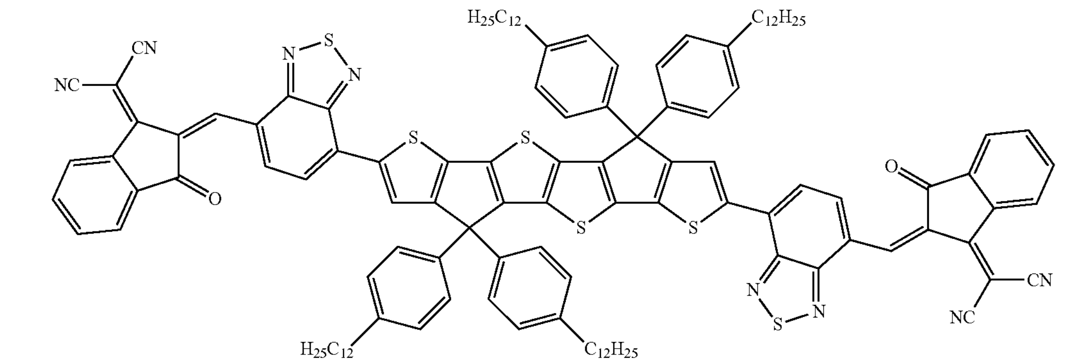 |
| NFA6 | 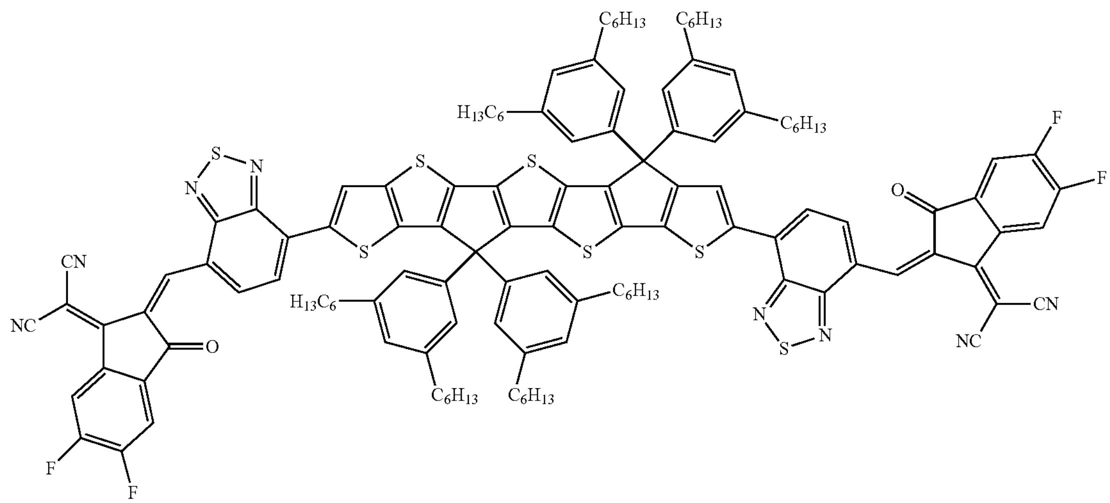 |
| NFA7 | 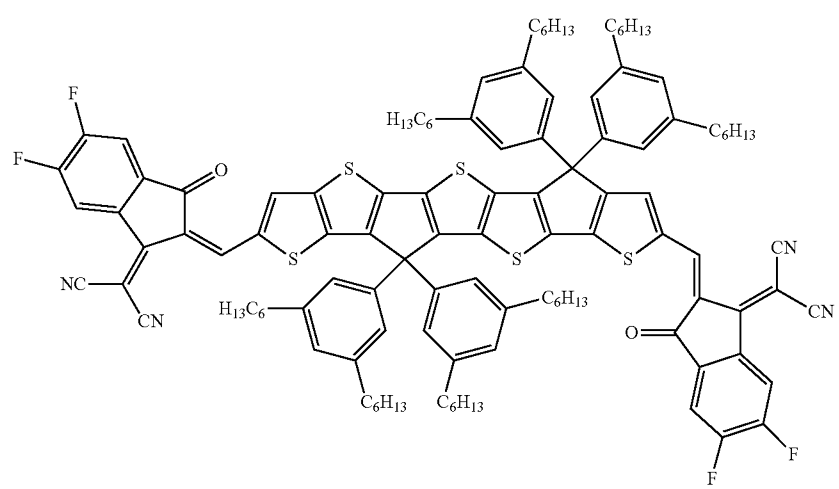 |

TABLE 1-continued

Structures of non-fullerene acceptors

| # | Structure |
|---|---|
| ITIC | (structure shown) |

Table 2 shows the formulation characteristics of the individual photoactive material solutions, comprising polymer P1, P2, P3, P4 or C1, respectively, as electron donor component, and fullerene PCBM-C60 or acceptor NFA1, NFA2 or ITIC as electron acceptor component. The solvent is either o-xylene, or a mixture of o-xylene with 2,4-dimethylanisole in 80:20 ratio (v/v).

TABLE 2

Formulation characteristics

| No. | Polymer | Acceptor | Ratio Polymer:Acceptor | Concentration g/L | Solvent |
|---|---|---|---|---|---|
| 1 | C1 | PCBM-C60 | 1:1.5 | 25 mg/ml | o-xylene |
| 2 | P1 | PCBM-C60 | 1:1.5 | 25 mg/ml | o-xylene/DMA |
| 3 | P2 | PCBM-C60 | 1:1.5 | 25 mg/ml | o-xylene/DMA |
| 4 | P3 | PCBM-C60 | 1:1.5 | 25 mg/ml | o-xylene/DMA |
| 5 | P4 | PCBM-C60 | 1:1.5 | 25 mg/ml | o-xylene/DMA |
| 6 | P1 | ITIC | 1:1.3 | 23 mg/ml | o-xylene |
| 7 | P1 | NFA1 | 1:1.3 | 23 mg/ml | o-xylene |
| 8 | P1 | NFA2 | 1:1.3 | 23 mg/ml | o-xylene |

A2: Inverted Device Properties

Current-voltage characteristics are measured using a Keithley 2400 SMU while the solar cells are illuminated by a Newport Solar Simulator at 100 mW-cm$^{-2}$ white light. The solar simulator is equipped with AM1.5G filters. The illumination intensity is calibrated using a Si photodiode. All the device characterization is done in a dry-nitrogen atmosphere.

Power conversion efficiency is calculated using the following expression $$\eta = \frac{V_{oc} \times J_{sc} \times FF}{P_{in}}$$

where FF is defined as $$FF = \frac{V_{max} \times J_{max}}{V_{oc} \times J_{sc}}$$

OPV device characteristics were measured for a blend which contains either Polymer P1 of the present invention or reference Polymer C1 and PCBM-C60 as an acceptor, and is coated from an organic solution. Details of the solution composition are shown in Table 2.

Table 3 shows the device characteristics for the individual OPV devices comprising a photoactive layer with a BHJ formed from the active material (acceptor/polymer) solutions of Table 2.

TABLE 3

Photovoltaic cell characteristics under simulated solar irradiation at 1 sun (AM1.5G).

| | | | Average Performance | | | |
|---|---|---|---|---|---|---|
| No. | Polymer | Acceptor | Voc mV | Jsc mA·cm$^{-2}$ | FF % | PCE % |
| 1 | C1 | PCBM-C60 | 758 | 10.7 | 45 | 3.6 |
| 2 | P1 | PCBM-C60 | 758 | 13.3 | 67 | 6.7 |
| 3 | P2 | PCBM-C60 | 808 | 9.3 | 44 | 3.4 |
| 4 | P3 | PCBM-C60 | 745 | 11.7 | 63 | 5.5 |
| 5 | P4 | PCBM-C60 | 803 | 3.9 | 30 | 1.0 |
| 6 | P1 | ITIC | 800 | 13.4 | 47 | 5.0 |
| 7 | P1 | NFA1 | 750 | 15.3 | 49 | 5.6 |
| 8 | P1 | NFA2 | 720 | 17.2 | 59 | 7.3 |

Table 3 shows that the fill factor (FF) and power conversion efficiency (PCE) are significantly increased when using polymer P1 compared to polymer C1, which is an advantage for module production.

Table 4 shows the evolution of power conversion efficiency (PCE) of encapsulated photovoltaic cells, under constant 1 Sun illumination, using an Atlas Solar Simulator at 50° C.

TABLE 4

Stability of photovoltaic cells under constant illumination

| No. | Polymer | Acceptor | Initial PCE % | PCE after 200 h % | Relative loss |
|---|---|---|---|---|---|
| 1 | P1 | PCBM-060 | 6.9 | 4.0 | −42% |
| 6 | P1 | NFA1 | 6.4 | 4.8 | −25% |

Table 4 shows that stability of a photovoltaic cell comprising P1 and NFA1 is significantly improved in comparison to a photovoltaic cell comprising P1 and PCBM-C60.

Use Example B

B1: Bulk Heterojunction Organic Photodetector Devices (OPDs)

Devices are fabricated onto glass substrates with six pre-patterned ITO dots of 5 mm diameter to provide the bottom electrode. The ITO substrates are cleaned using a standard process of ultrasonication in Decon90 solution (30 minutes) followed by washing with de-ionized water (×3) and ultrasonication in de-ionized water (30 minutes). The ZnO ETL layer is deposited by spin coating a ZnO nanoparticle dispersion onto the substrate and drying on a hotplate for 10 minutes at a temperature between 100 and 140° C. A formulation of P1 and an acceptor is prepared at a ratio of 1:1 in o-xylene at a concentration of 20 mg/ml, and stirred for 17 hours at a temperature of between 23° C. and 60° C. The active layer is deposited using blade coating (K101 Control Coater System from RK). The stage temperature is set to between 20-60° C., the blade gap set between 2 and 200 μm and the speed set between 2 and 8 m/min, targeting a final dry film thickness of 500-1000 nm. Following coating the active layer is annealed at 100° C. for 10 minutes. The $MoO_3$ HTL layer is deposited by E-beam vacuum deposition from $MoO_3$ pellets at a rate of 1 Å/s, targeting 15 nm thickness. Finally, the top silver electrode is deposited by thermal evaporation through a shadow mask, to achieve Ag thickness between 30 and 80 nm.

The J-V curves are measured using a Keithley 4200 system under light and dark conditions at a bias from +5 to −5 V. The light source is a 580 nm LED with power 0.5 $mW/cm^2$.

The EQE of OPD devices are characterized between 400 and 1100 nm under −2V bias, using an External Quantum Efficiency (EQE) Measurement System from LOT-QuantumDesign Europe.

Table 5 shows the characteristics of the individual formulations.

TABLE 5

Formulation characteristics

| No. | Acceptor | Polymer |
|---|---|---|
| 1 | NFA3 | P1 |
| 2 | NFA4 | P1 |
| 3 | NFA5 | P1 |
| 4 | NFA6 | P1 |
| 5 | NFA7 | P1 |

Table 6 shows the EQE values for the individual OPD devices comprising a photoactive layer with a BHJ formed from the photoactive acceptor/polymer formulations of Table 5.

TABLE 6

EQEs for the devices

| | EQE % | | |
|---|---|---|---|
| No. | 650 nm | 850 nm | 940 nm |
| 1 | 40 | 28 | 26 |
| 2 | 36 | 28 | 21 |
| 3 | 42 | 31 | 26 |
| 4 | 64 | 60 | 26 |
| 5 | 53 | 38 | 36 |

The invention claimed is:

1. A method comprising including a polymer and a non-fullerene acceptor in an electronic or optoelectronic device, or in a component of such a device or in an assembly comprising such a device, wherein the polymer has the structure of formula I

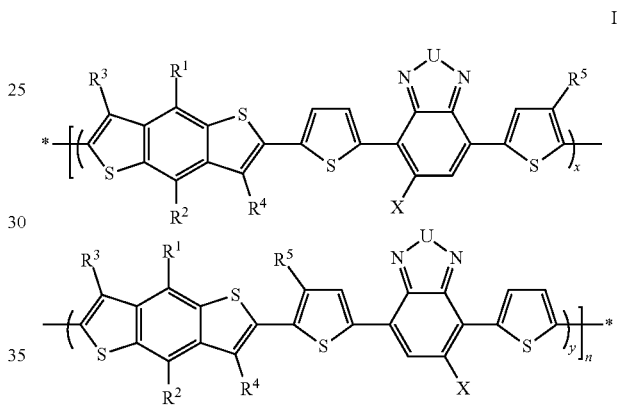

I wherein the individual radicals, independently of each other and on each occurrence identically or differently, have the following meanings U S, Se or $NR^0$, X F, Cl or CN, $R^1$, $R^2$ H, F, $R^x$, —$OR^x$, —$SR^x$, —C(=O)$R^x$ or —C(=O)—$OR^x$, —S(=O)$_2R^x$, $R^3$, $R^4$ H, F, Cl, CN, $R^x$, —$OR^x$, —$SR^x$, —C(=O)$R^x$, —C(=O)—$OR^x$ or —S(=O)$_2R^x$, $R^5$ straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F, Cl, Br, I or CN, $R^x$ straight-chain, branched or cyclic alkyl with 1 to 30 C atoms, in which one or more $CH_2$ groups are optionally replaced by —O—, —S—, —C(=O)—, —C(=S)—, —C(=O)—O—, —O—C(=O)—, —$NR^0$—, —$SiR^0R^{00}$—, —$CF_2$—, —$CR^0$=$CR^{00}$—, —$CY^1$=$CY^2$— or —C≡C— in such a manner that O and/or S atoms are not linked directly to one another, and in which one or more H atoms are optionally replaced by F or CN, or aryl, heteroaryl, arylalkyl or heteroarylalkyl, wherein each of the aforementioned cyclic groups has 5 to 20 ring atoms, is mono- or polycyclic, does optionally contain fused rings, and is unsubstituted or substituted by one or more identical or different groups L, L F, Cl, —NO$_2$, —CN, —NC, —NCO, —NCS, —OCN, —SCN, R$^0$, OR$^0$, SR$^0$, —C(=O)X$^0$, —C(=O)R$^0$, —C(=O)—OR$^0$, —O—C(=O)—R$^0$, —NH$_2$, —NHR$^0$, —NR$^0$R$^{00}$, —C(=O)NHR$^0$, —C(=O)NR$^0$R$^{00}$, —SO$_3$R$^0$, —SO$_2$R$^0$, —OH, —NO$_2$, —CF$_3$, —SF$_5$, or optionally substituted silyl, or carbyl or hydrocarbyl with 1 to 40 atoms that is optionally substituted and optionally comprises one or more hetero atoms, Y$^1$, Y$^2$ H, F, Cl or CN, R$^0$, R$^{00}$ H or straight-chain or branched alkyl with 1 to 30 C atoms that is optionally fluorinated, X$^0$ halogen, x, y real numbers representing mole fractions, wherein 0<x<1 and 0<y<1 and x+y=1, n an integer >1, and wherein the non-fullerene acceptor is selected from the following subformulae

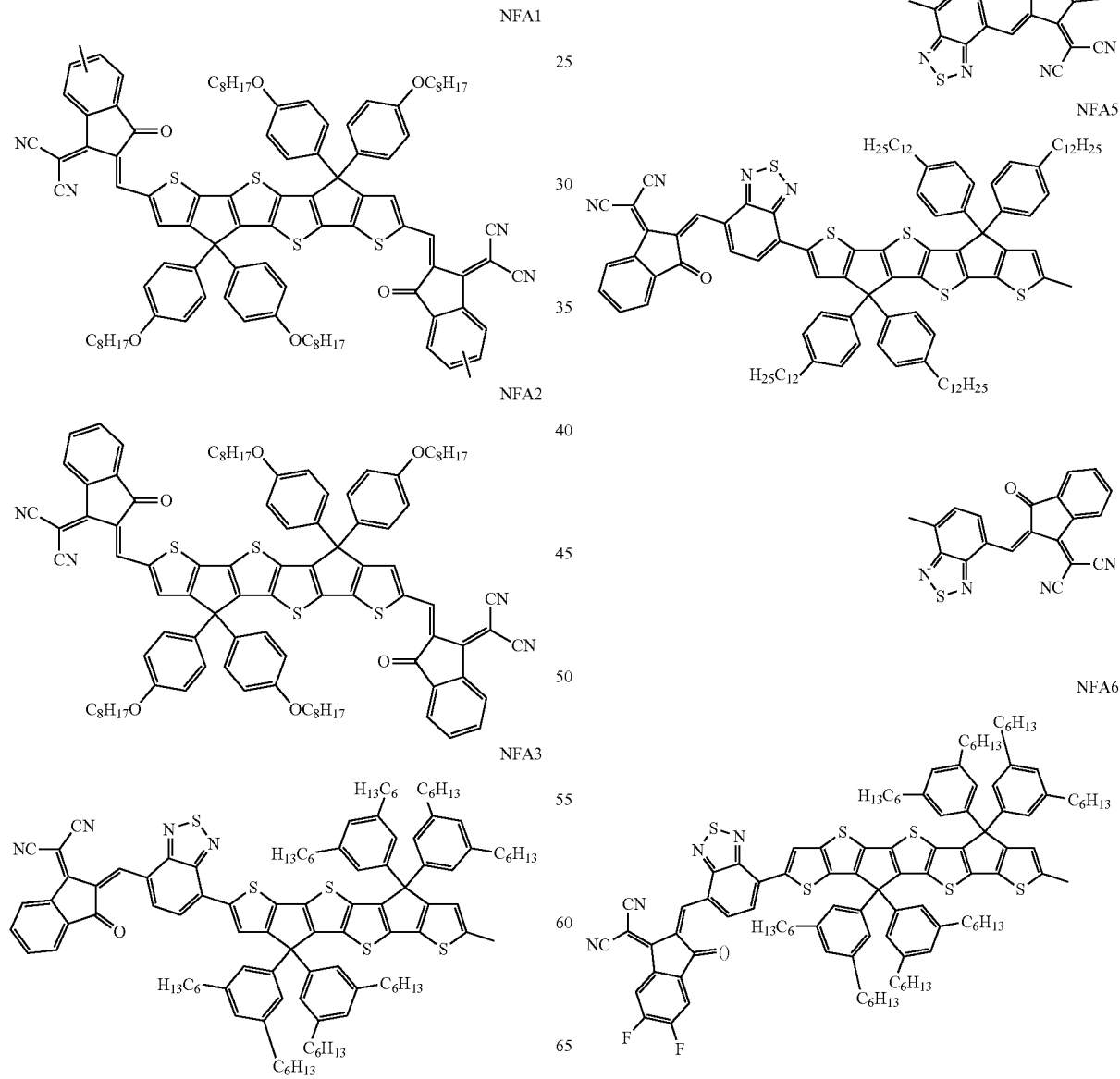

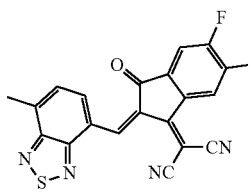

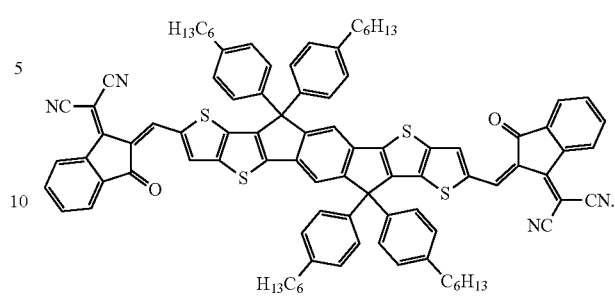

ITIC

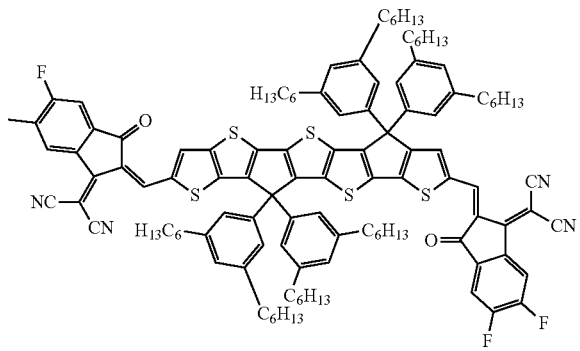

NFA7

2. The method of claim 1, characterized in that $R^3$ and $R^4$ of the polymer denote H.

3. The method of claim 1, characterized in that $R^1$ and $R^2$ of the polymer are selected from aryl, heteroaryl, arylalkyl or heteroarylalkyl, each of which has 5 to 20 ring atoms, optionally contains fused rings and is unsubstituted or substituted by one or more groups L as defined in claim 1, or $R^1$ and $R^2$ are selected from alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated.

4. The method according to claim 1, characterized in that $R^5$ of the polymer is selected from alkyl, alkoxy, oxaalkyl, thioalkyl, alkylcarbonyl or alkoxycarbonyl, all of which are straight-chain having 1 to 24 C atoms or branched having 3 to 24 C atoms, and are optionally fluorinated.

5. The method according to claim 1, characterized in that the polymer is selected from the following subformulae

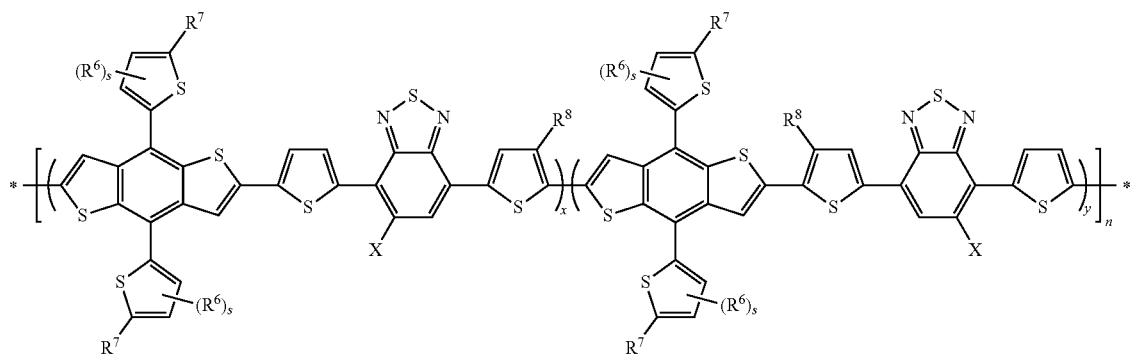

I1

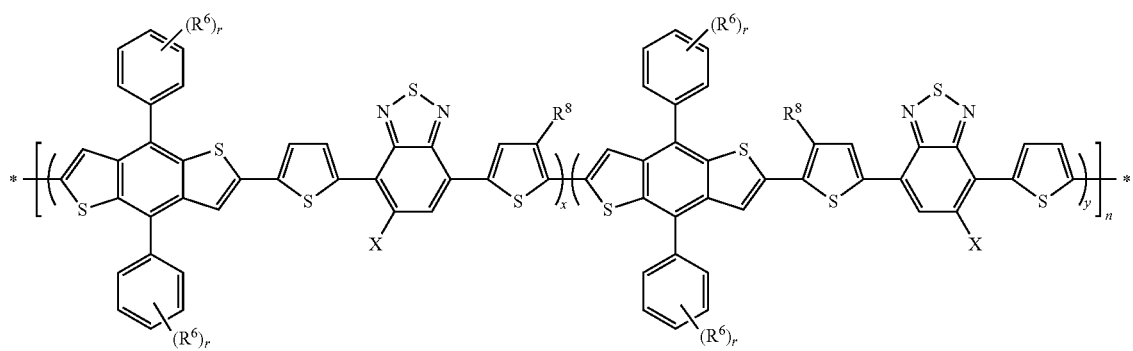

I2

-continued
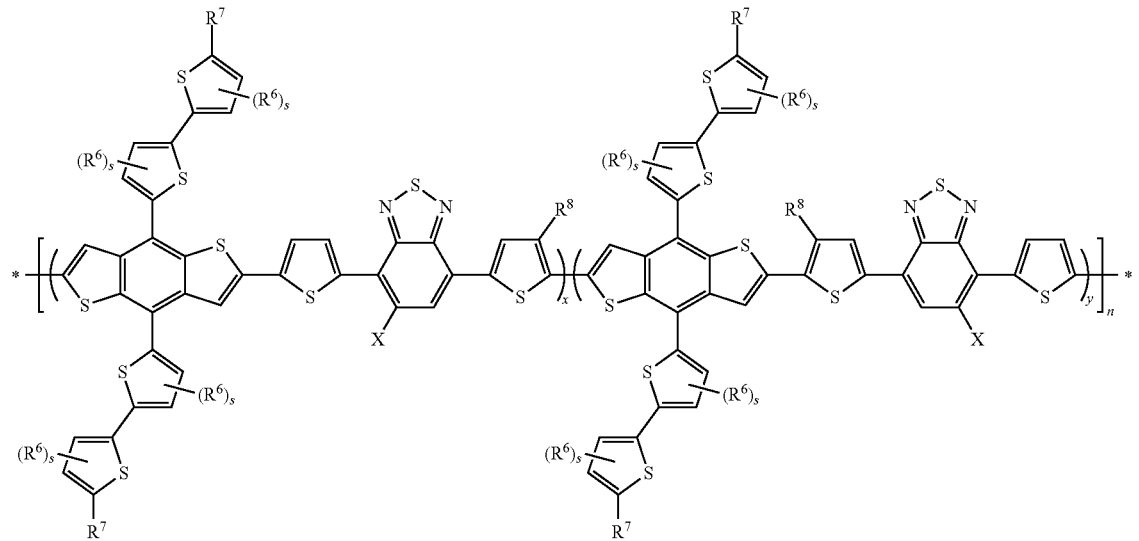
I3
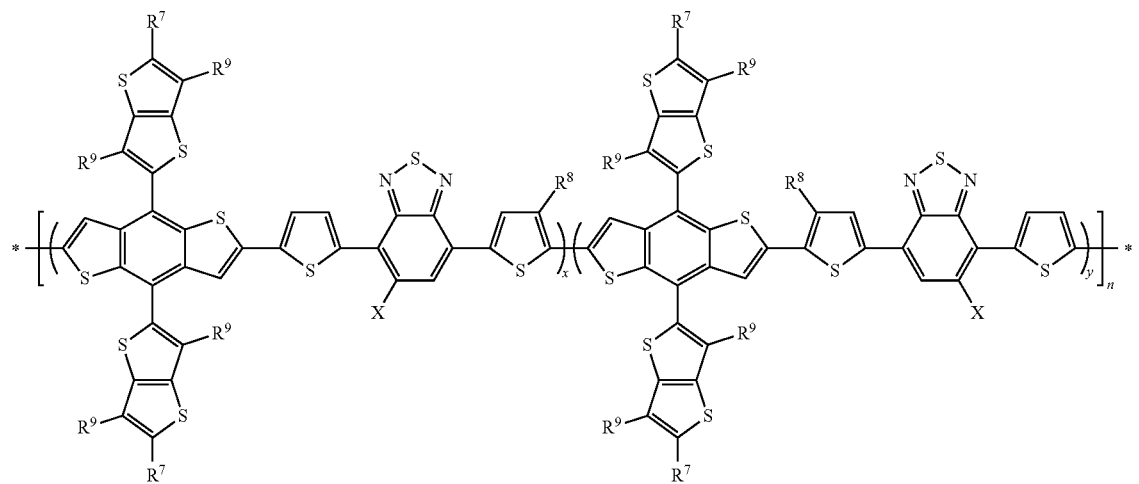
I4
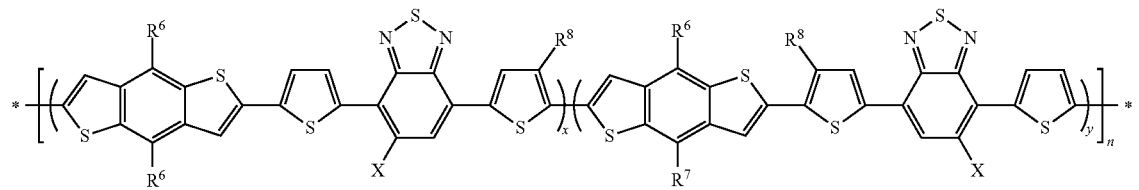
I5
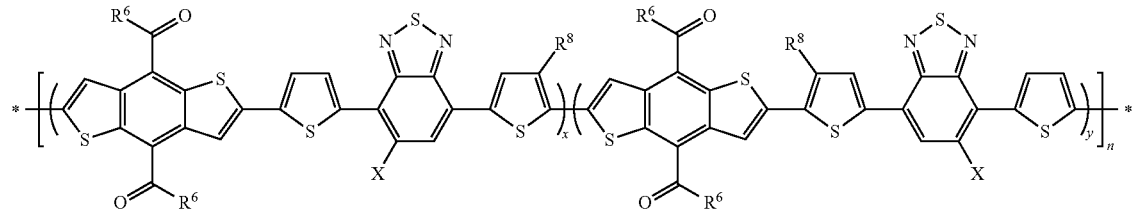
I6 wherein X, x, y and n are as defined in claim 1, $R^6$, $R^7$ and $R^8$, independently of each other and on each occurrence identically or differently, denote alkyl, alkoxy or thioalkyl all of which are straight-chain having 1 to 24 C atoms or branched having 3 to 24 C atoms, and are optionally fluorinated, $R^9$ is H or has one of the meanings given for $R^6$, r is 0, 1, 2 or 3, and s is 0, 1 or 2.

6. The method according to claim 5, characterized in that the polymer is selected from the following subformulae

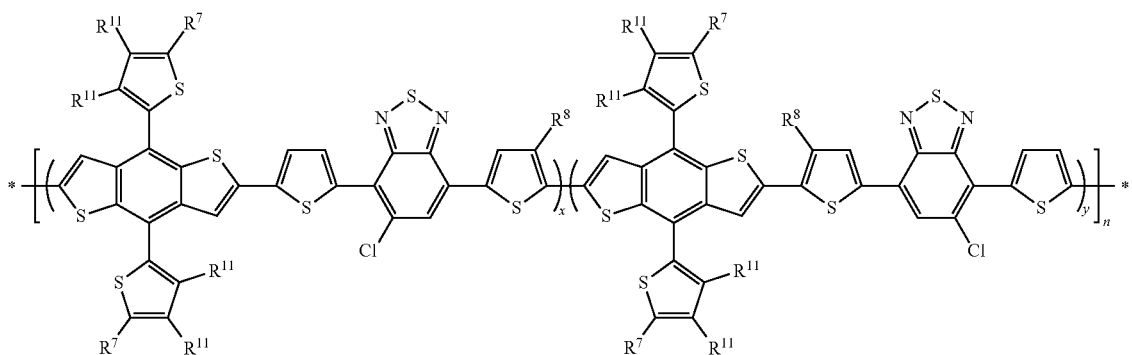

I1-1

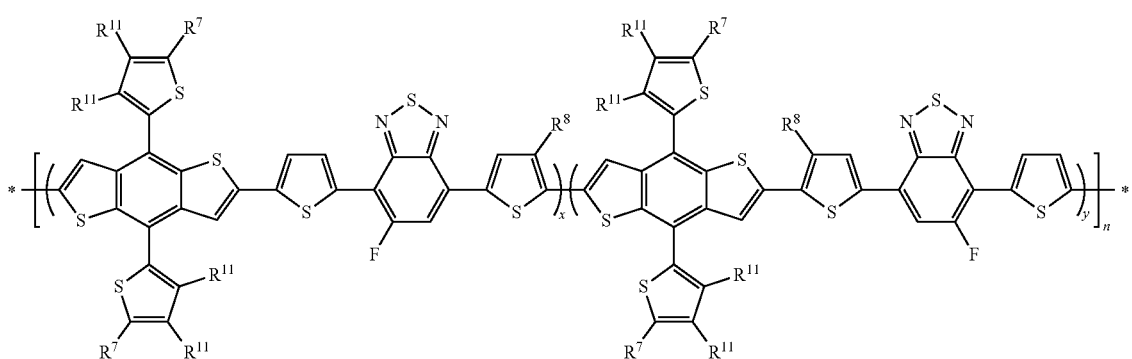

I1-2

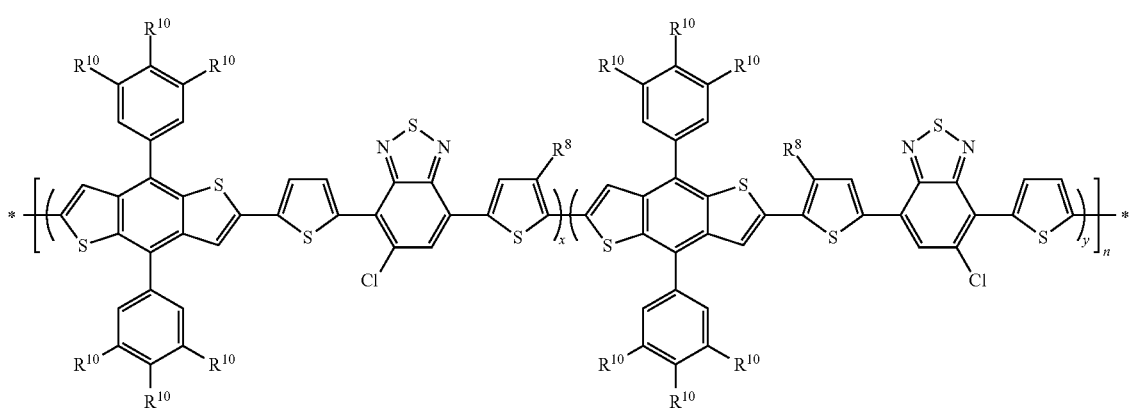

I2-1

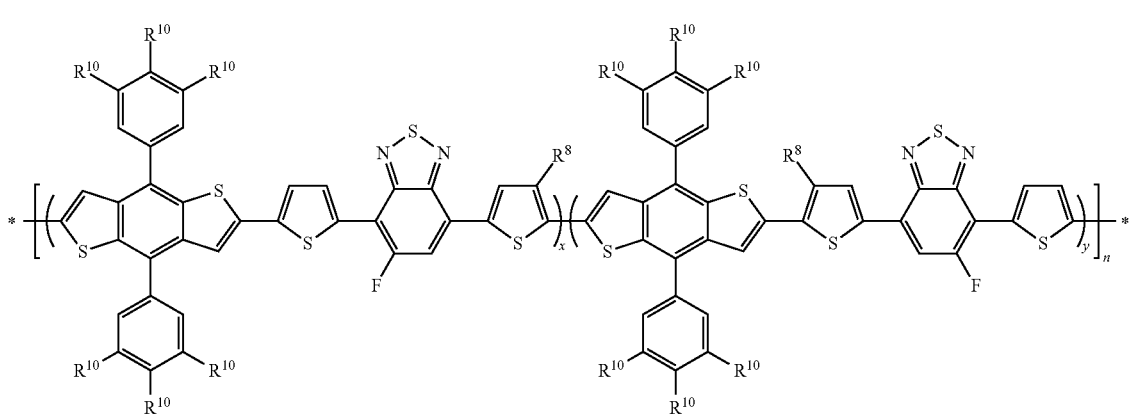

I2-2

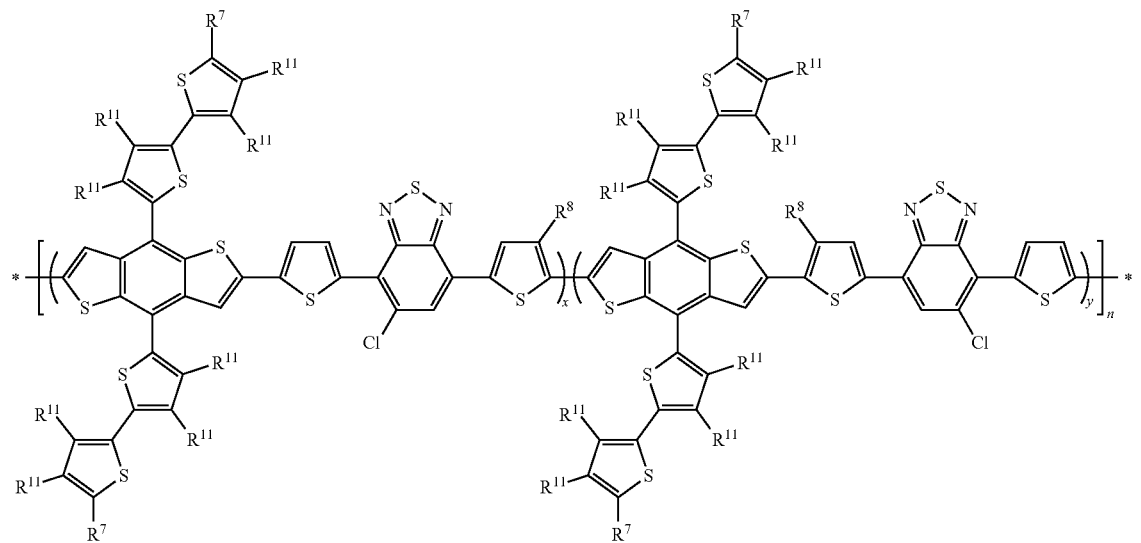
I3-1
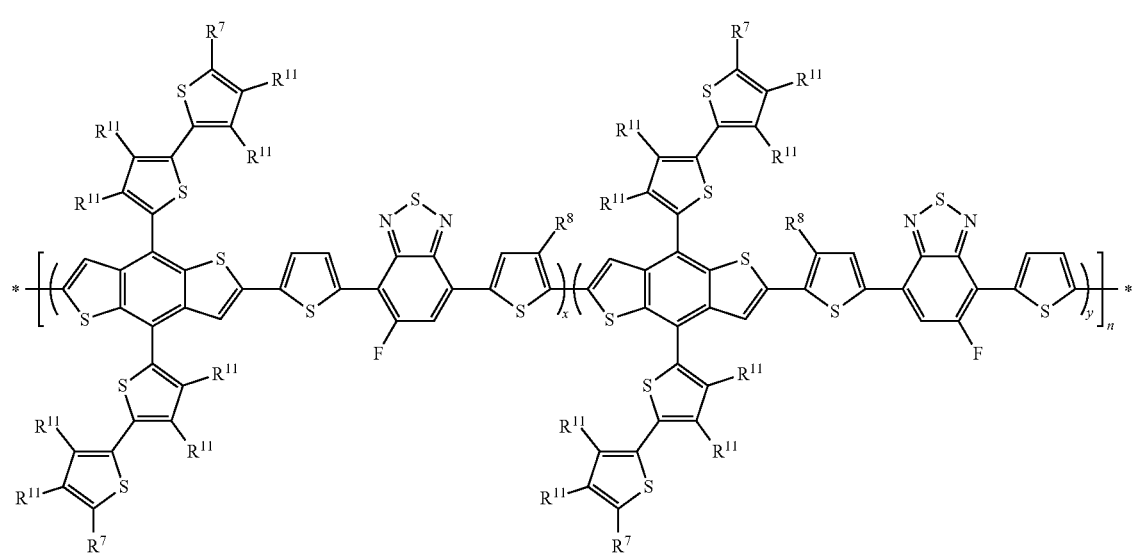
I3-2
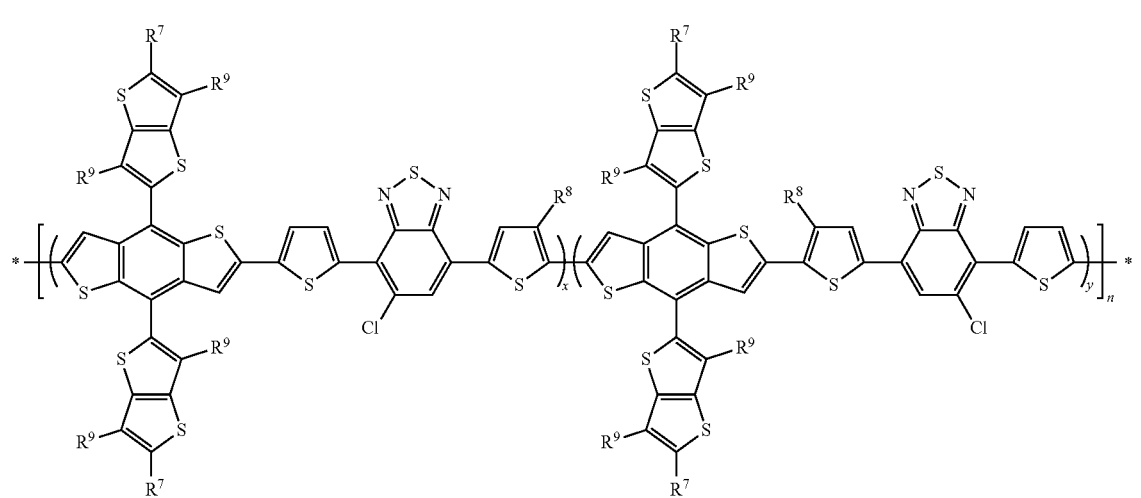
I4-1

-continued
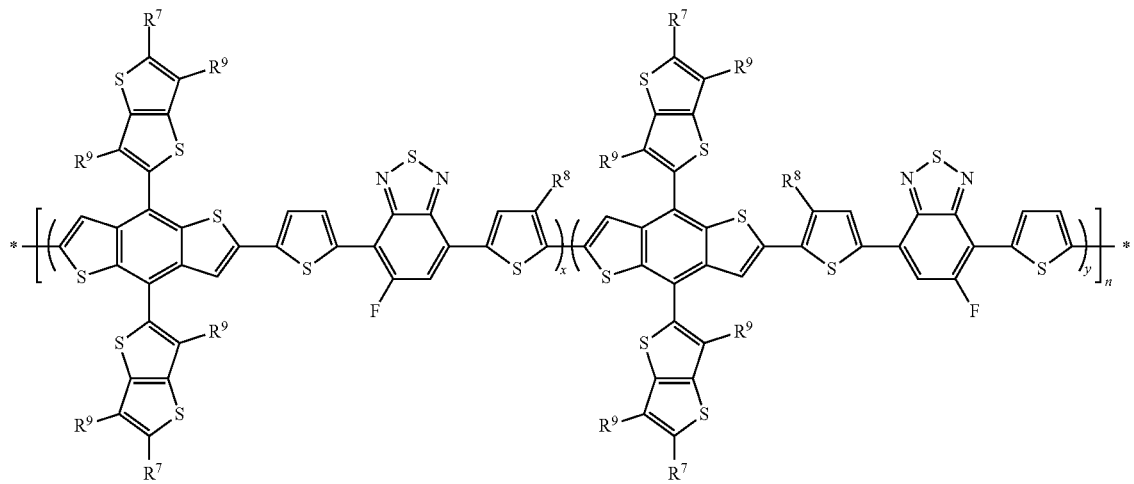
I4-2
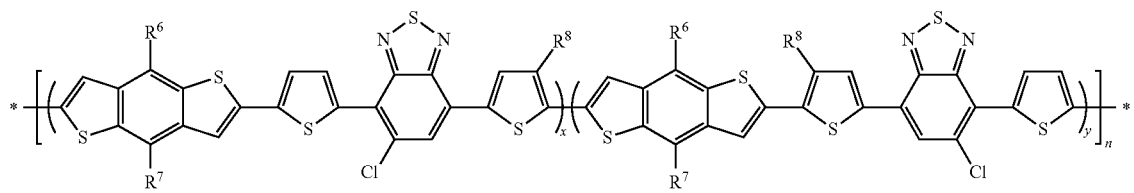
I5-1
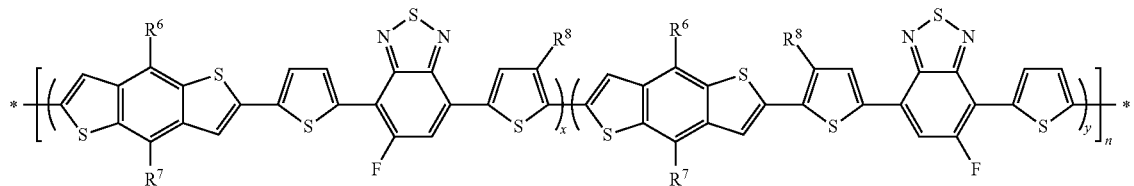
I5-2
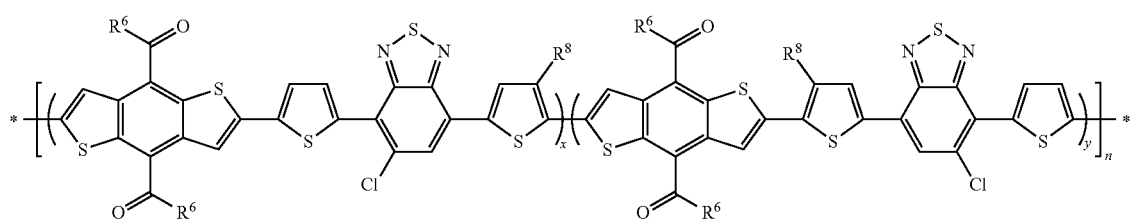
I6-1
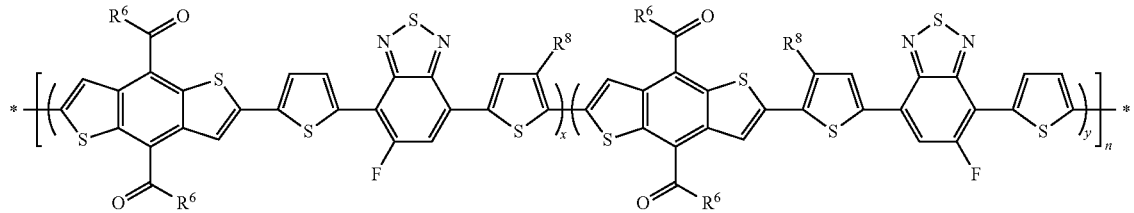
I6-2
wherein x, y, n, $R^6$, $R^7$, $R^8$, $R^9$, r and s are as defined in claim 5, and $R^{10}$ and $R^{11}$ have one of the meanings given for $R^6$ or denote H.
7. The method according to claim 1, characterized in that is selected from the following subformulae

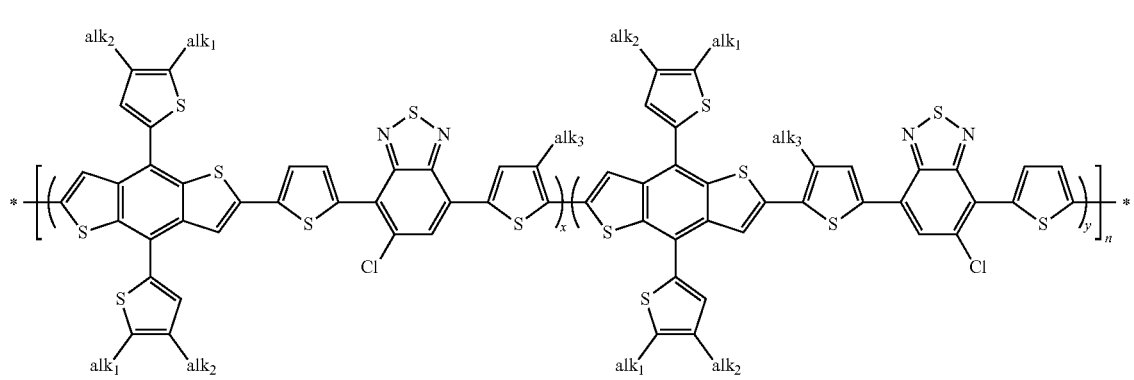
I1-1a
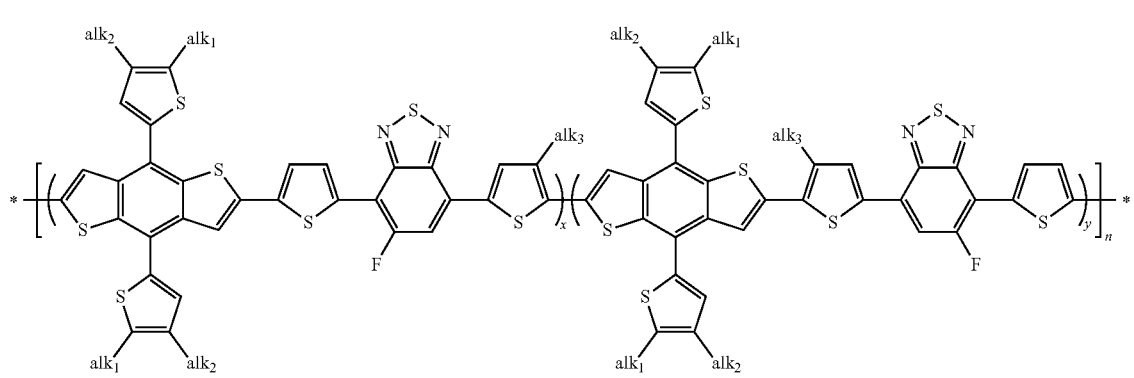
I1-2a
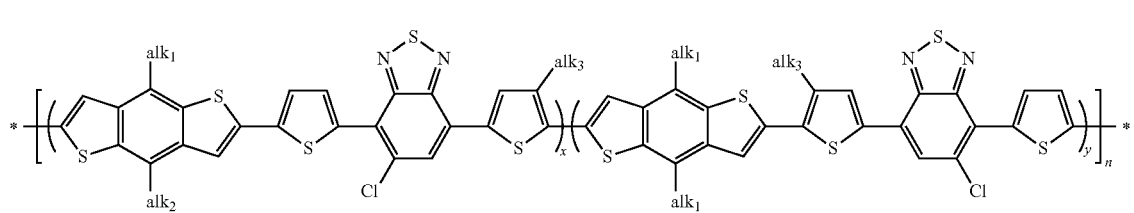
I5-1a
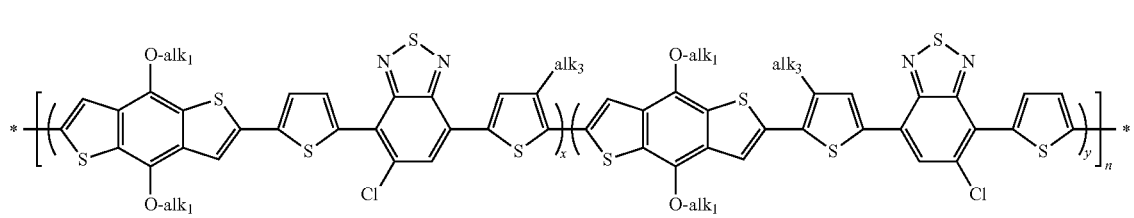
I5-1b
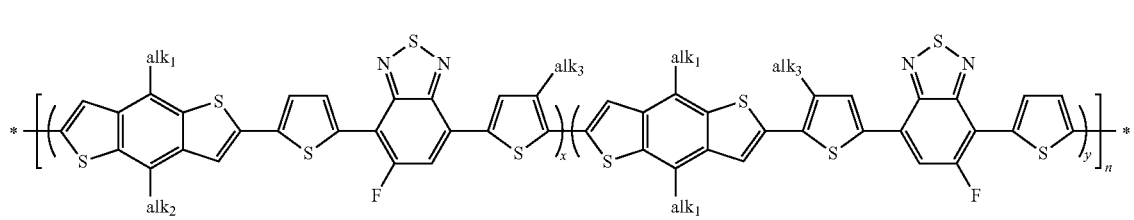
I5-2a
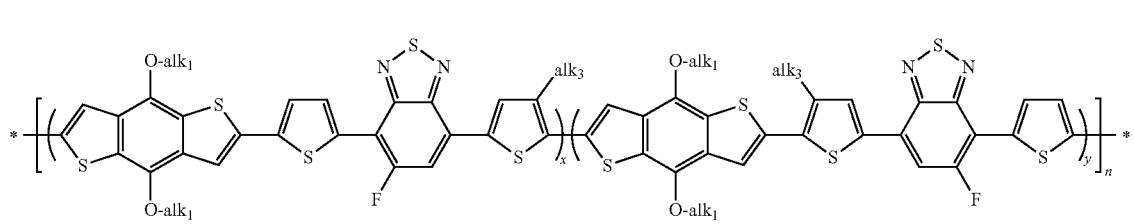
I5-2b -continued

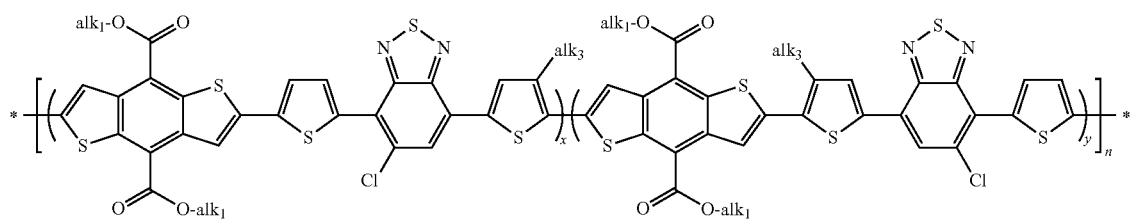

I6-1a

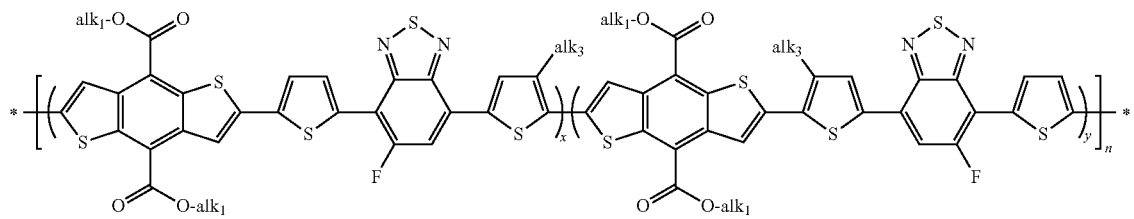

I6-2a wherein x, y and n are as defined in claim 1, "alk$_1$", "alk$_2$" and "alk$_3$" denote alkyl that is straight-chain having 1 to 24 C atoms or branched having 3 to 24 C atoms, and is optionally fluorinated, and "alk$_2$" may also denote H.

8. The electronic or optoelectronic device made by the method according to claim 1, which is selected from organic field effect transistors (OFET), organic thin film transistors (OTFT), organic light emitting electro-chemical cells (OLEC), organic photodetectors (OPD), organic solar cells, dye-sensitized solar cells (DSSC), perovskite-based solar cells (PSC), organic photoelectrochemical cells (OPEC), laser diodes, Schottky diodes, photoconductors, photodetectors, thermoelectric devices and LC windows.

9. The component made by the method according to claim 1, which is selected from charge injection layers, charge transport layers, interlayers, planarising layers, antistatic films, printed polarizers, polymer electrolyte membranes (PEM), conducting substrates and conducting patterns.

10. The assembly made by the method according to claim 1, which is selected from integrated circuits (IC), radio frequency identification (RFID) tags, security markings, security devices, flat panel displays, backlights of flat panel displays, electrophotographic devices, electrophotographic recording devices, organic memory devices, sensor devices, biosensors and biochips.

* * * * *